United States Patent [19]
Fang et al.

[11] Patent Number: 5,854,045
[45] Date of Patent: Dec. 29, 1998

[54] TRANSMEMBRANE TYROSINE PHOSPHATASE AND METHODS OF USE THEREOF

[75] Inventors: Kathy S. Fang, Berkeley, Calif.; Hidesaburo Hanafusa, New York, N.Y.

[73] Assignee: The Rockefeller University

[21] Appl. No.: 850,917

[22] Filed: May 2, 1997

Related U.S. Application Data

[62] Division of Ser. No. 241,853, May 12, 1994, Pat. No. 5,693,488.

[51] Int. Cl.$^6$ .............................. C12N 9/16; C07K 14/00; C07K 14/705
[52] U.S. Cl. ...................... 435/196; 530/300; 530/326; 536/23.2; 435/69.1
[58] Field of Search .................................. 435/196, 69.1; 530/350, 300, 326; 536/23.2

[56] References Cited

PUBLICATIONS

Brady–Kalnay et al. (1993) *J. Cell Biol.* 122, 961–972.
Levy et al. (1993) *J. Biol. Chem.* 268, 10573–10581.
Charbonneau and Tonks. (1992) *Annu. Rev. Cell Biol.* 8, 463–493.
Flickinger et al. (1992) *Mol. Cell. Biol.* 12, 883–893.
Krueger and Saito. (1992) *Proc. Natl. Acad. Sci. USA* 89, 7417–7421.
Mosinger et al. (1992) *Proc. Natl. Acad. Sci. USA* 89, 499–503.
Bishop. (1991) *Cell* 64, 235–248.
Fischer et al. (1991) *Science* 253, 401–406.
Fukui et al. (1991) *Oncogene* 6, 407–411.
Krueger et al. (1990) *EMBO J.* 9, 3241–3252.
Winkelmann et al. (1990) *J. Biol. Chem.* 265, 11827–11832.
Streuli et al. (1989) *Proc. Natl. Acad. Sci. USA* 86, 8698–8702.
Thomas. (1989) *Ann. Rev. Immunol.* 7, 339–369.
Davison and Critchley. (1988) *Cell* 52, 159–160.
Baron et al. (1987) *J. Biol. Chem.* 262, 17623–17629.
Boyd et al. (1987) *Proc. Natl. Acad. Sci. USA* 84, 8525–8529.
Rosen. (1987) *Science* 237, 1452–1458.
Marchesi. (1985) *Ann. Rev. Cell Biol.* 1, 531–561.
Bajwa et al. (1984) *Nucleic Acid Res.* 12, 7721–7739.

*Primary Examiner*—Sally P. Teng
*Attorney, Agent, or Firm*—Klauber & Jackson

[57] ABSTRACT

The present invention relates to regulation and control of cellular processes by transmembrane protein tyrosine phosphatases, and to ligands that agonize or antagonize tyrosine phosphorylation mediated by such tyrosine phosphatases. This invention further relates to diagnosis and therapy based on the activity of such ligands. In particular, the invention provides a novel transmembrane protein tyrosine phosphatase-λ (PTPλ), nucleic acids encoding the same, antibodies to the PTPλ, and methods for identifying ligands to the PTPλ of the invention. A specific Example describes the isolation and characterization of the first chicken transmembrane PTP, called ChPTPλ. It has a unique extracellular domain containing a Ser/Thr/Pro-rich region, spectrin-like repeats, a fibronectin III domain, and an alternatively spliced N-terminus. The expression of ChPTPλ in various tissues and cells was also examined. ChPTPλ was shown to have a tyrosine-specific phosphatase activity, and the basic characteristics of this enzyme were studied.

5 Claims, 11 Drawing Sheets

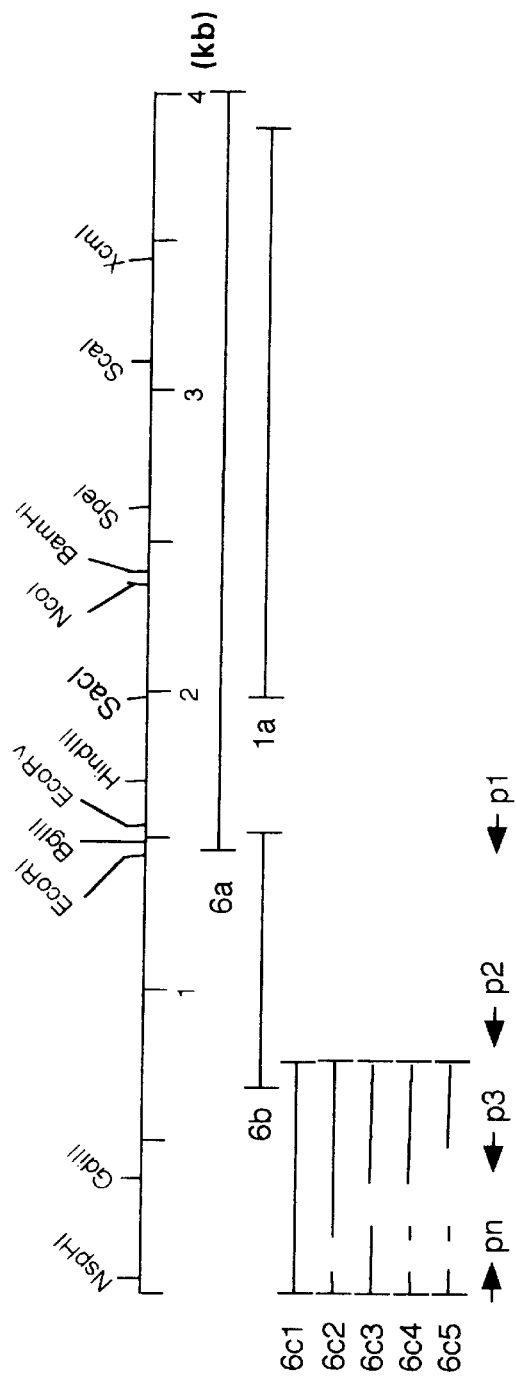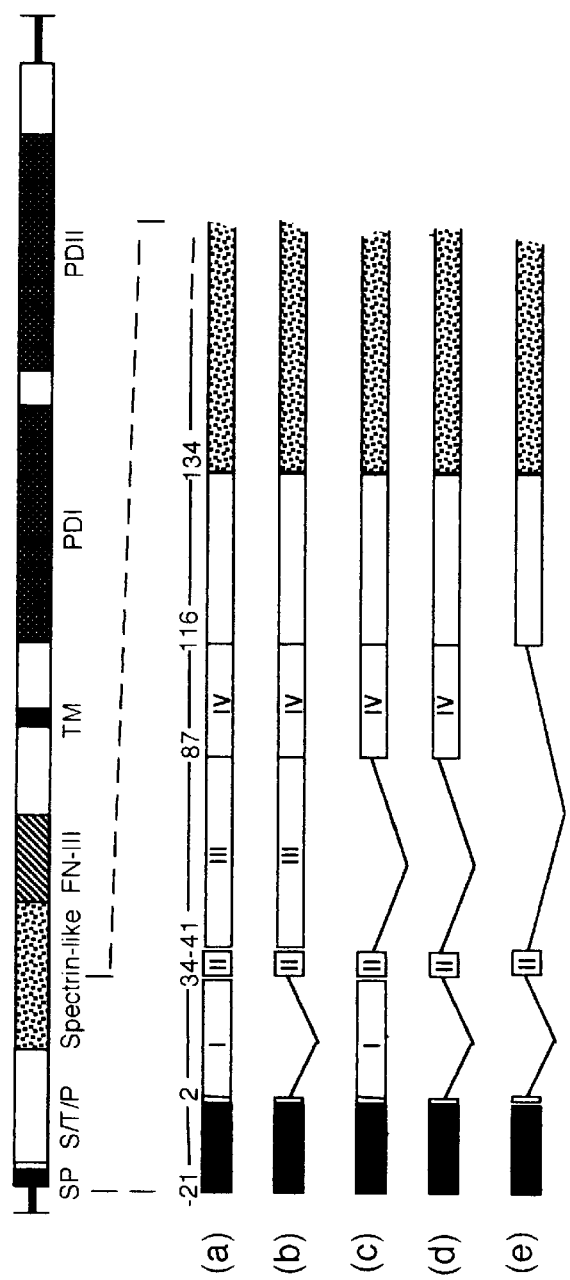
FIG.1A
FIG.1B

```
              2430                              2460                              2490                              2520
GTGAATGCTCTCAGCAACTTTTTAGTGGCCCAATAGTGGTTCATTGCAGTGCTGGAGTGGGCGCACTGGGACCTATATTGAATTGACGCTATGTTGAGGGCTGATGCAGAGGGC              789
 V  N  A  L  S  N  F  F  S  G  P  I  V  Y H C  S  A  G  V  G  R T G T  Y  I  G I  D  A  M  L  E  G  L  D  A  E  G
                             2550                              2580                              2610                              2640
AGAGTGGATGTTTATGGCTACGTTGTGAAGCTGCGCGGGCAGCGCCTCATGTTCAAGTAGAGTCACAGTACATCCTTATCCATCAAGCACTAGTGAATACCATCAGTATGGGAA              829
 R  V  D  V  Y  G  Y  V  V  K  L  R  R  Q  R  C  L  M  V  Q  V  E  S  Q  Y  I  L  I  H  Q  A  L  V  E  Y  H  Q  Y  G  E
                             2670                              2700                              2730                              2760
ACAGGTCAGCCTCTCAGAACTACATTCCTATCTGAAGACAATCTTAACAATTCCGAGCCTTCTCTGCTGAGGCGAAATTCAGAGACTGCCTCCTACAAGGGATGG              869
 T  E  V  S  L  S  E  L  H  S  Y  L  N  N  L  K  R  K  D  P  P  S  E  P  S  L  L  E] A  K  F  Q  R  L  P  S  Y  K  G  W
                             2790                              2820                              2850                              2880
CGGACAGAACACTGGGAATCGAGAGGAAATAAGAACAAAATAGGAGTGCCAACAATTCCGTATGACTTTAACCGAGTGCCGATCAGGAGTGAAGAGGAACAAAGTAAGGAGGGT              909
 R  T  Q  N  T  G  N  R  E  E [N  K  N  K  N  R  S  A  N  T  I  P  Y  D  F  N  R  V  P  I  R  S  E  E  E  Q  S  K  E  G
                             2910                              2940                              2970                              3000
GAACATGATTCAGAGGACTCATCAGATGAGGACAGTGACTGTGAAGAATCAAGCAGATAGATTCATAACTGGTTACTGGGGTCCAAAAGCCATGATTGCAACACAAGA              949
 E  H  D  S  E  D  S  S  D  E  D  S  D  C  E  E  S  S  R  Y  I  N  A  S  F  I  T  G  Y  W  G  P  K  A  M  I  A  T  Q  G
                             3030                              3060                              3090                              3120
CCACTGCAGGAAACTATCTCTGACTTTCTGGCAAATGGTATTCCAAAGAAAGTCAAGTCATTGTTATGCTGACAGAGCTGAAAGAAGGGATCAGGAGAACTCTGCACAGTACTGGGAG              989
 P  L  Q  E  T  I  S  D  F  W  Q  M  V  F  Q  R  K  V  K  V  I  V  M  L  T  E  L  K  E  G  D  Q  E  L  C  A  Q  Y  W  G
                             3150                              3180                              3210                              3240
GAAGGAAGACAAACATATGATGATGACATAGAAGTTCAAGTTCATAACTGCTGTCCGATGTGCATTGATGCCACACATCGTCACACATCGTGAAGAGAAAGAAACACAGAAGTA              1029
 E  G  R  Q  T  Y  D  D  D  I  E  V  Q  V  H  N  C  C  P  S  Y  T  I  R  A  F  D  V  T  H  L  K  R  K  E  T  Q  K  V
                             3270                              3300                              3330                              3360
TATCAGTATCAATATCACAAGTGGAATGGATTGGATGTTCCAGAGACCCCAAAGATTTAGTCGATATGATCCTAAACAAAAAGTGCCATCCAGACCCAGCCTCTGAGGACAGC              1069
 Y  Q  Y  Q  Y  H  K  W  N  G  L  D  V  P  E  E  D  P  P  K  D  L  V  D  M  I  L  S  L  K  Q  K  V  P  S  R  P  A  S  E  D  S
                             3390                              3420                              3450                              3480
AGGAACAGCCGCAGCGTCCCATTGTCATCCACTGCTGTGATGGATCGGACAGCCTGGTGTGTTTGTGCTTGATGACCCTCTGGAAAGTGCAGAAAGTGAGAAGTAATAGATGTT              1109
 R  N  S  R  S  V  P  F  V  I H C  C  D  G  S  Q  Q T W  C  V  L  C  L  M  T  L  L  E  S  A  E  T  E  E  V  I  D  V
                             3510                              3540                              3570                              3600
TTCCAAGTAGTAAAAGCTCTTCGTCGGACAGGCTGGAGTGGTCTCCCACCTTTGAACAATACCAATTTCTATATGACACCATGCCTGCCCAGAATGACAATATAAG              1149
 F  Q  V  V  K  A  L  R  R  S  R  L  G  V  V  S  T  F  E  Q  Y  Q  F  L  Y  D  T  I  A  R  T  Y  P  A  Q  N  G  Q  I ]K
                             3630                              3660                              3690                              3720
AACATCCATCAGGAAGATAAGGTTGAATTTGCAACGAAGTAGAACGAAAGATCAGGAAAGTTCTACTCCATCATTGACCTATTGACTACTATTGATCTTACTCCACCTGAGAACTCCTGAA              1189
 N  I  H  Q  E  D  K  V  E  F  C  N  E  V  E  K  K  D  Q  E  S  D  L  I  T  I  D  L  T  P  S  T  P  E  E  N  D  A  P  E
                             3750                              3780                              3810                              3840
TGTTGCGATGATTTAAGGCTGCAGATACCAATAAGGGGACCTACAACTCCAGTTTTTTTTAACTTAGAATTTTTTTTAAGTAAAAGTGTATTTCATACCA              1216
 C  C  D  D  F  K  A  A  D  T  N  K  G  T  E  S  S  T  N  G  P  T  T  P  V  L  T  *
                             3870                              3900                              3930                              3960
AACAAATCTTAACCACAGTAAGAAACTTATGATTTTCCCCCTCCCTTTTGGAAAACATTTATGTCCGATTTCAAAGGTACAAATTTAAGTGATACTTGAAACTTCTAAAGAGTGACA

AAGAACTGT (3969)
```

FIG. 4B (sequence alignment figure - rows labeled Ros, Ryk, Eph, Eck, Mek, Hek, NCAM, FN(21), FN(24))

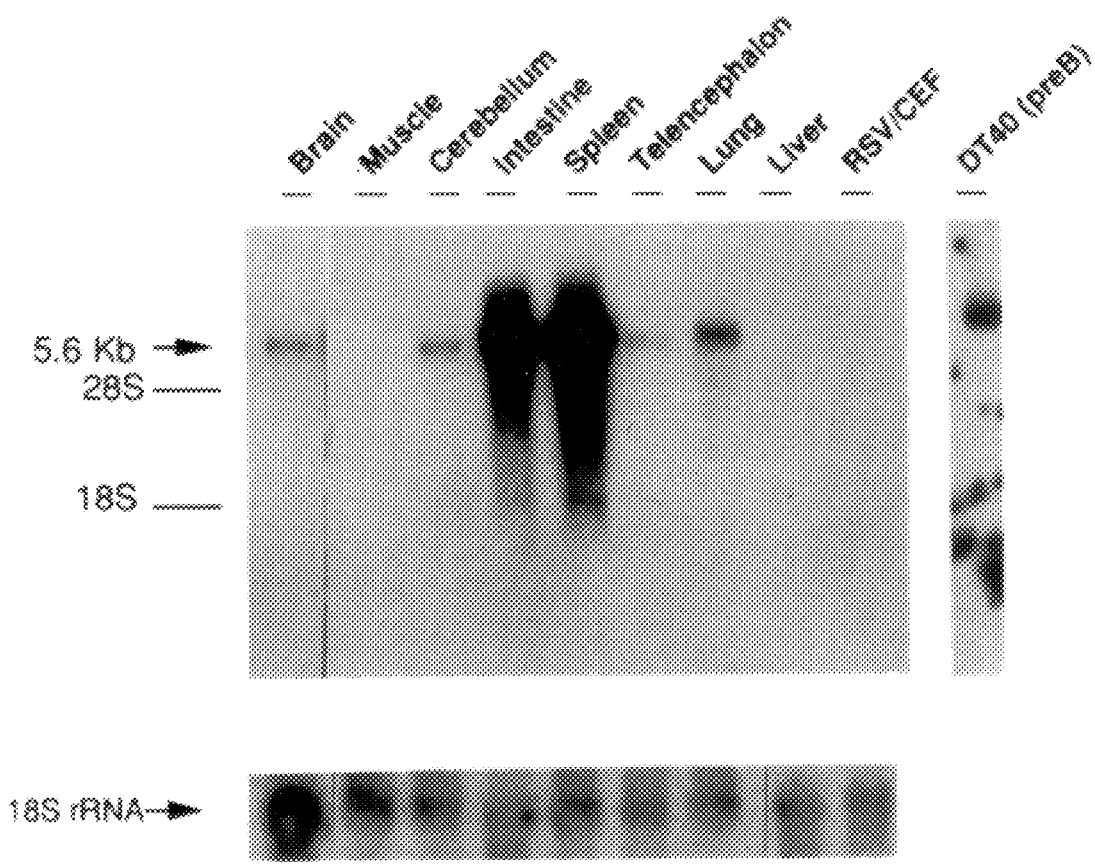

SEQUENCE LISTING ( 1 ) GENERAL INFORMATION:

( i i i ) NUMBER OF SEQUENCES: 37

( 2 ) INFORMATION FOR SEQ ID NO:1:

( i ) SEQUENCE CHARACTERISTICS:
        ( A ) LENGTH: 3969 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Gallus domesticus
        ( B ) STRAIN: DT40

( i x ) FEATURE:
        ( A ) NAME/KEY: CDS
        ( B ) LOCATION: 91..3802

( x i ) SEQUENCE DESCRIPTION: SEQ ID NO:1:

```
AGGAAGCCAA CTCCTTCTCA GATAAGCAGG CAGTGTAATA GCGAGACACA TGCTGCTTCG                    60

TAAGGATACG CCTGATTTCC AGAAATAACC ATG TTT TTG TGC CTT AAA CTC TTG                    114
                                    Met Phe Leu Cys Leu Lys Leu Leu
                                     1               5

GCG TTT GGC GTT GCC TTT CTG TGC CAG GAT GCT TTT GCC CAA GCA GGA                     162
Ala Phe Gly Val Ala Phe Leu Cys Gln Asp Ala Phe Ala Gln Ala Gly
         10              15              20

AAT GAT AAT TTG ACC TCT GCC AGC TCT CTC TCC TCT ACG TTA CCT ACA                     210
Asn Asp Asn Leu Thr Ser Ala Ser Ser Leu Ser Ser Thr Leu Pro Thr
 25              30              35                          40

CCT ACA CGC TCC ACA TCA TTC TCA CCT CCA AGC ACC ACT GCA GGA GTT                     258
Pro Thr Arg Ser Thr Ser Phe Ser Pro Pro Ser Thr Thr Ala Gly Val
             45              50                          55

CAG CCA GCA TCA ACT GGT GCC TCT CCC ACA GCC AGC ACG CAC CTC TCC                     306
Gln Pro Ala Ser Thr Gly Ala Ser Pro Thr Ala Ser Thr His Leu Ser
         60              65                      70

ACG CAC TCA GGC TCT GGT CCG ACC ACG GGA CTC GGC CAT TTG CAG CAT                     354
Thr His Ser Gly Ser Gly Pro Thr Thr Gly Leu Gly His Leu Gln His
         75              80                      85

AGC AGC CCT GCT GCC CTC ACC ACA CGC ACT CTC ACT GCC TTT CAT CAA                     402
Ser Ser Pro Ala Ala Leu Thr Thr Arg Thr Leu Thr Ala Phe His Gln
         90              95                     100

ACT GTA TCA GAT TAT TAC AGT TCA ACA TCC TTG CAC AAC ACC ACC TCA                     450
Thr Val Ser Asp Tyr Tyr Ser Ser Thr Ser Leu His Asn Thr Thr Ser
105             110             115                     120

CCA GTC ATC ACG CCA GCA AGC ACT GAG ACC ATC CCC ACT AGC ACA ATA                     498
Pro Val Ile Thr Pro Ala Ser Thr Glu Thr Ile Pro Thr Ser Thr Ile
                125             130                     135

GAA AGT GCT ACA ACA ACG GAA GAA CCT TGT GAT AAT AGT ATT GAT TAC                     546
Glu Ser Ala Thr Thr Thr Glu Glu Pro Cys Asp Asn Ser Ile Asp Tyr
            140             145                     150

GGG AAT ATA GAA GAA AAG AAT AAC TCG GCT GAA GTT ACG CTA AAG AAT                     594
Gly Asn Ile Glu Glu Lys Asn Asn Ser Ala Glu Val Thr Leu Lys Asn
            155             160                     165

CTC AAA GAA AAC AGA ATA TAT GAT ATT CTG CTG GAA GAT GGG AAG AGC                     642
Leu Lys Glu Asn Arg Ile Tyr Asp Ile Leu Leu Glu Asp Gly Lys Ser
170             175                     180

TTA TCA GTG AAT GCC AGC AAC AAC ATA GTA ATG CTT AAT TGG TGC AGA                     690
Leu Ser Val Asn Ala Ser Asn Asn Ile Val Met Leu Asn Trp Cys Arg
185                 190                 195                     200

AGA TAT ACA GTT CAA TCT CGT AGT TGC AAG GTC ATG TAT CTT ACT ATT                     738
Arg Tyr Thr Val Gln Ser Arg Ser Cys Lys Val Met Tyr Leu Thr Ile
                205             210                     215

CCA CCT GAT GAA AAA AGG TAT ACT TTT GGT GCC AAG AGC ATT GGA AAC                     786
Pro Pro Asp Glu Lys Arg Tyr Thr Phe Gly Ala Lys Ser Ile Gly Asn
                220             225                     230

GAC AAT GCA ACA TTG CGT TTA AAT TCT TTA TGT ATA GAT TGC GAA GAT                     834
Asp Asn Ala Thr Leu Arg Leu Asn Ser Leu Cys Ile Asp Cys Glu Asp
            235             240                     245

GTC TGT TCT AAT GTG ACT GTT AGC TGC AAA ACA AAT TCC ATA AAC TCA                     882
Val Cys Ser Asn Val Thr Val Ser Cys Lys Thr Asn Ser Ile Asn Ser
250                 255                 260

GGA GGC ACT GGG AAT TTA ACT GGT AGC TAC GAA TTG ATG AAA CAT GAT                     930
Gly Gly Thr Gly Asn Leu Thr Gly Ser Tyr Glu Leu Met Lys His Asp
265             270             275                     280

ATA AAT GCT GAC AAC ATA ACG ATA CTT TCT TTA TCA TCC GAC AGT GAG                     978
Ile Asn Ala Asp Asn Ile Thr Ile Leu Ser Leu Ser Ser Asp Ser Glu
            285             290                     295
```

| | | | | | | | | | | | | | | | | |
|---|---|---|---|---|---|---|---|---|---|---|---|---|---|---|---|---|
| TAC | CTC | TGC | AGA | GTT | ACA | GTA | AGG | TTT | TTT | GAA | AAG | AAT | TTT | ACC | AAA | 1026 |
| Tyr | Leu | Cys | Arg 300 | Val | Thr | Val | Arg 305 | Phe | Phe | Glu | Lys | Asn 310 | Phe | Thr | Lys | |
| GAA | GTC | AAC | ATA | ACT | ACA | GAT | TAT | GAT | GCT | CCA | AAA | GCA | CCA | GAA | AAC | 1074 |
| Glu | Val | Asn | Ile 315 | Thr | Thr | Asp | Tyr 320 | Asp | Ala | Pro | Lys | Pro 325 | Pro | Glu | Asn | |
| CTT | ACG | GTG | CAT | CCT | ACT | GAC | AGA | AAT | GTA | ACA | GTT | ACG | TGG | ATG | AAA | 1122 |
| Leu | Thr 330 | Val | His | Pro | Thr | Asp 335 | Arg | Asn | Val | Thr | Val 340 | Thr | Trp | Met | Lys | |
| CCT | ACC | GGC | ACA | TTA | GAA | AAA | CAT | ATA | GAT | GGC | TAT | ACT | GTG | GAG | TGC | 1170 |
| Pro | Thr 345 | Gly | Thr | Leu | Glu 350 | Lys | His | Ile | Asp 355 | Gly | Tyr | Thr | Val | Glu 360 | Cys | |
| AAT | AAC | ACT | TCT | CAA | AAC | GTT | AAC | AGG | AAT | GAG | ACC | AGC | TTT | ACT | TGT | 1218 |
| Asn | Asn | Thr | Ser | Gln 365 | Asn | Val | Asn | Arg | Asn 370 | Glu | Thr | Ser | Phe | Thr 375 | Cys | |
| GGT | GAT | TTA | GAA | CCT | TAC | AGC | ACT | GGC | TCT | GTG | TCT | GTA | AGA | GCA | TTT | 1266 |
| Gly | Asp | Leu | Glu 380 | Pro | Tyr | Ser | Thr | Gly 385 | Ser | Val | Ser | Val | Arg 390 | Ala | Phe | |
| AAA | AAA | AGC | AAG | TAT | AAG | AAT | AAA | AAC | TTT | GAG | GGA | GAA | AAA | GTG | AAT | 1314 |
| Lys | Lys | Ser 395 | Lys | Tyr | Lys | Asn | Lys 400 | Asn | Phe | Glu | Gly | Glu 405 | Lys | Val | Asn | |
| GGC | AGC | TTT | CAA | ACG | AAA | CCA | GCA | AAA | CCA | GAG | AAT | GTG | ACT | GAC | TTC | 1362 |
| Gly | Ser 410 | Phe | Gln | Thr | Lys | Pro 415 | Ala | Lys | Pro | Glu | Asn 420 | Val | Thr | Asp | Phe | |
| AAA | CTA | ACA | TTG | CTG | GCT | GAT | AAT | ACT | GTC | AAA | GTT | GCC | TGC | CGA | AGT | 1410 |
| Lys 425 | Leu | Thr | Leu | Leu 430 | Ala | Asp | Asn | Thr | Val 435 | Lys | Val | Ala | Cys | Arg 440 | Ser | |
| CAA | AAA | GTG | TAT | GGA | AAT | GAA | ACA | AAA | TTT | AAA | TTA | TCT | TGG | AAT | TCC | 1458 |
| Gln | Lys | Val | Tyr | Gly 445 | Asn | Glu | Thr | Lys | Phe 450 | Lys | Leu | Ser | Trp | Asn 455 | Ser | |
| AGC | AGC | AAC | AGT | GGT | GAG | AAT | CAG | AGG | AAA | AAT | GAA | TGC | AAT | TTT | ACA | 1506 |
| Ser | Ser | Asn | Ser 460 | Gly | Glu | Asn | Gln | Arg 465 | Lys | Asn | Glu | Cys | Asn 470 | Phe | Thr | |
| GTA | AGA | GAT | CTC | TCT | TAC | TTG | ACA | AAA | TAT | ACG | TTT | AAG | ATA | TCT | GTG | 1554 |
| Val | Arg | Asp | Leu 475 | Ser | Tyr | Leu | Thr | Lys 480 | Tyr | Thr | Phe | Lys | Ile 485 | Ser | Val | |
| TTT | AAT | GGA | GTG | TAT | ACA | GGA | GAC | TCG | GTA | TGT | GAG | GAA | ATA | TAT | ACC | 1602 |
| Phe | Asn | Gly 490 | Val | Tyr | Thr | Gly | Asp 495 | Ser | Val | Cys | Glu | Glu 500 | Ile | Tyr | Thr | |
| AGA | TAT | AAC | TCG | AGG | GCC | CTG | ATT | ATA | TTC | TTG | GTG | TTC | TTG | ATT | GTT | 1650 |
| Arg | Tyr | Asn 505 | Ser | Arg | Ala | Leu 510 | Ile | Ile | Phe | Leu | Val 515 | Phe | Leu | Ile | Val 520 | |
| GTG | ACA | TCA | ATT | GCT | TTA | CTG | TTG | GTT | CTG | TAT | AAA | ATC | TAT | GAC | CTA | 1698 |
| Val | Thr | Ser | Ile | Ala 525 | Leu | Leu | Leu | Val | Leu 530 | Tyr | Lys | Ile | Tyr | Asp 535 | Leu | |
| CAC | CAA | AAA | AAG | CTT | AGC | AAT | TCT | TCT | GAA | GTC | ATC | AGC | CTT | GTA | GCA | 1746 |
| His | Gln | Lys | Lys 540 | Leu | Ser | Asn | Ser | Ser 545 | Glu | Val | Ile | Ser | Leu 550 | Val | Ala | |
| GTT | AAA | GAT | GAT | GAA | AGG | CAG | CTT | TTG | AAC | ATA | GAG | CCA | ATA | CCT | TCA | 1794 |
| Val | Lys | Asp 555 | Asp | Glu | Arg | Gln | Leu 560 | Leu | Asn | Ile | Glu | Pro 565 | Ile | Pro | Ser | |
| GAG | AAA | CTG | TTG | GAG | ACA | TAC | AAG | AGG | AAG | ATT | GCT | GAT | GAA | GGA | AGA | 1842 |
| Glu | Lys | Leu 570 | Leu | Glu | Thr | Tyr | Lys 575 | Arg | Lys | Ile | Ala | Asp 580 | Glu | Gly | Arg | |
| CTT | TTC | TTG | GAT | GAA | TTT | CAG | AGC | ATT | CCA | AGA | ATT | TTC | ACT | AAA | TTT | 1890 |
| Leu 585 | Phe | Leu | Asp | Glu | Phe 590 | Gln | Ser | Ile | Pro | Arg 595 | Ile | Phe | Thr | Lys | Phe 600 | |
| CCA | ATG | AAG | GAG | GCC | AAG | AGG | AGC | CAT | AAT | CAG | AAC | AAA | AAC | CGT | TAC | 1938 |
| Pro | Met | Lys | Glu | Ala 605 | Lys | Arg | Ser | His | Asn 610 | Gln | Asn | Lys | Asn | Arg 615 | Tyr | |

| | | | | | | | | | | | | | | | | |
|---|---|---|---|---|---|---|---|---|---|---|---|---|---|---|---|---|
| ATT | GAT | ATT | CTT | CCA | TAT | GAT | CAT | AAC | CGT | GTT | GAG | CTC | TCT | GAG | ATT | 1986 |
| Ile | Asp | Ile | Leu 620 | Pro | Tyr | Asp | His | Asn 625 | Arg | Val | Glu | Leu | Ser 630 | Glu | Ile | |
| CCA | GGA | GAC | CCA | GGA | TCA | GAC | TAC | ATC | AAC | GCA | AGT | TAT | ATT | GAT | GGC | 2034 |
| Pro | Gly | Asp 635 | Pro | Gly | Ser | Asp | Tyr 640 | Ile | Asn | Ala | Ser | Tyr 645 | Ile | Asp | Gly | |
| TTC | AAA | GAA | CCG | AGA | AAA | TAC | ATT | GCT | GCA | CAA | GGC | CCC | AAG | GAT | GAA | 2082 |
| Phe | Lys 650 | Glu | Pro | Arg | Lys | Tyr 655 | Ile | Ala | Ala | Gln | Gly 660 | Pro | Lys | Asp | Glu | |
| ACC | ACG | GAT | GAT | TTC | TGG | AGA | ATG | ATC | TGG | GAA | CAG | AAA | GCA | ACA | ATT | 2130 |
| Thr 665 | Thr | Asp | Asp | Phe | Trp 670 | Arg | Met | Ile | Trp | Glu 675 | Gln | Lys | Ala | Thr | Ile 680 | |
| ATT | GTC | ATG | GTT | ACT | CGC | TGT | GAG | GAA | GGA | AAC | AGG | AAC | AAA | TGT | GCC | 2178 |
| Ile | Val | Met | Val | Thr 685 | Arg | Cys | Glu | Glu | Gly 690 | Asn | Arg | Asn | Lys | Cys 695 | Ala | |
| CAG | TAC | GGG | CCA | TCA | ATG | GAG | AAT | GGC | TCT | GCA | ACA | TAT | GGG | GAC | ATA | 2226 |
| Gln | Tyr | Gly | Pro 700 | Ser | Met | Glu | Asn | Gly 705 | Ser | Ala | Thr | Tyr | Gly 710 | Asp | Ile | |
| ACT | GTG | AAG | ATC | AAC | GAA | AGT | AAA | ATA | TGT | CCA | GAC | TAT | ATA | ATT | CAG | 2274 |
| Thr | Val | Lys 715 | Ile | Asn | Glu | Ser | Lys 720 | Ile | Cys | Pro | Asp | Tyr 725 | Ile | Ile | Gln | |
| AAA | CTG | CAC | ATC | ACA | AAT | GGA | AGA | GAA | AGA | ACA | TCT | GGA | AGA | GAT | GTC | 2322 |
| Lys | Leu 730 | His | Ile | Thr | Asn | Gly 735 | Arg | Glu | Arg | Thr | Ser 740 | Gly | Arg | Asp | Val | |
| ACT | CAC | ATT | CAG | TTC | ACC | AGC | TGG | CCA | GAC | CAT | GGC | GTT | CCC | GAG | GAT | 2370 |
| Thr 745 | His | Ile | Gln | Phe | Thr 750 | Ser | Trp | Pro | Asp | His 755 | Gly | Val | Pro | Glu | Asp 760 | |
| CCA | CAT | CTC | CTT | CTC | AAA | CTC | CGA | CGC | AGA | GTG | AAT | GCT | CTC | AGC | AAC | 2418 |
| Pro | His | Leu | Leu | Leu 765 | Lys | Leu | Arg | Arg | Arg 770 | Val | Asn | Ala | Leu | Ser 775 | Asn | |
| TTT | TTT | AGT | GGC | CCA | ATA | GTG | GTT | CAT | TGC | AGT | GCT | GGA | GTT | GGG | CGC | 2466 |
| Phe | Phe | Ser | Gly 780 | Pro | Ile | Val | Val | His 785 | Cys | Ser | Ala | Gly | Val 790 | Gly | Arg | |
| ACT | GGG | ACC | TAT | ATT | GGA | ATT | GAC | GCT | ATG | TTG | GAG | GGG | CTG | GAT | GCA | 2514 |
| Thr | Gly | Thr 795 | Tyr | Ile | Gly | Ile | Asp 800 | Ala | Met | Leu | Glu | Gly 805 | Leu | Asp | Ala | |
| GAG | GGC | AGA | GTG | GAT | GTT | TAT | GGC | TAC | GTT | GTG | AAG | CTG | CGC | CGG | CAG | 2562 |
| Glu | Gly | Arg 810 | Val | Asp | Val | Tyr | Gly 815 | Tyr | Val | Val | Lys 820 | Leu | Arg | Arg | Gln | |
| CGG | TGC | CTC | ATG | GTT | CAA | GTA | GAG | TCA | CAG | TAC | ATC | CTT | ATC | CAT | CAA | 2610 |
| Arg 825 | Cys | Leu | Met | Val | Gln 830 | Val | Glu | Ser | Gln | Tyr 835 | Ile | Leu | Ile | His | Gln 840 | |
| GCA | CTA | GTG | GAA | TAC | CAT | CAG | TAT | GGA | GAA | ACA | GAG | GTC | AGC | CTC | TCA | 2658 |
| Ala | Leu | Val | Glu | Tyr 845 | His | Gln | Tyr | Gly | Glu 850 | Thr | Glu | Val | Ser | Leu 855 | Ser | |
| GAA | CTA | CAT | TCC | TAT | CTT | AAC | AAT | CTG | AAA | AGA | AAA | GAT | CCT | CCA | AGT | 2706 |
| Glu | Leu | His | Ser 860 | Tyr | Leu | Asn | Asn | Leu 865 | Lys | Arg | Lys | Asp | Pro 870 | Pro | Ser | |
| GAA | CCT | TCT | CTG | CTG | GAG | GCG | AAA | TTT | CAG | AGA | CTG | CCT | TCC | TAC | AAG | 2754 |
| Glu | Pro | Ser 875 | Leu | Leu | Glu | Ala | Lys 880 | Phe | Gln | Arg | Leu | Pro 885 | Ser | Tyr | Lys | |
| GGA | TGG | CGG | ACA | CAG | AAC | ACT | GGG | AAT | CGA | GAG | GAA | AAT | AAG | AAC | AAA | 2802 |
| Gly | Trp | Arg | Thr 890 | Gln | Asn | Thr | Gly | Asn 895 | Arg | Glu | Glu | Asn | Lys 900 | Asn | Lys | |
| AAT | AGG | AGT | GCC | AAC | ACA | ATT | CCG | TAT | GAC | TTT | AAC | CGA | GTG | CCG | ATC | 2850 |
| Asn | Arg | Ser 905 | Ala | Asn | Thr | Ile | Pro 910 | Tyr | Asp | Phe | Asn | Arg 915 | Val | Pro | Ile 920 | |
| AGG | AGT | GAA | GAG | GAA | CAA | AGT | AAG | GAG | GGT | GAA | CAT | GAT | TCA | GAG | GAC | 2898 |
| Arg | Ser | Glu | Glu | Glu 925 | Gln | Ser | Lys | Glu | Gly 930 | Glu | His | Asp | Ser | Glu 935 | Asp | |

| | |
|---|---:|
| TCA TCA GAT GAG GAC AGT GAC TGT GAA GAA TCA AGC AGA TAC ATT AAT<br>Ser Ser Asp Glu Asp Ser Asp Cys Glu Glu Ser Ser Arg Tyr Ile Asn<br>                 940                     945                 950 | 2946 |
| GCT TCC TTC ATA ACT GGT TAC TGG GGT CCA AAA GCC ATG ATT GCA ACA<br>Ala Ser Phe Ile Thr Gly Tyr Trp Gly Pro Lys Ala Met Ile Ala Thr<br>        955                     960                     965 | 2994 |
| CAA GGA CCA CTG CAG GAA ACT ATC TCT GAC TTC TGG CAA ATG GTA TTC<br>Gln Gly Pro Leu Gln Glu Thr Ile Ser Asp Phe Trp Gln Met Val Phe<br>970                     975                     980 | 3042 |
| CAA AGA AAA GTC AAA GTC ATT GTT ATG CTG ACA GAG CTG AAA GAA GGG<br>Gln Arg Lys Val Lys Val Ile Val Met Leu Thr Glu Leu Lys Glu Gly<br>985                     990                     995                1000 | 3090 |
| GAT CAG GAA CTC TGT GCA CAG TAC TGG GGA GAA GGA AGA CAA ACA TAT<br>Asp Gln Glu Leu Cys Ala Gln Tyr Trp Gly Glu Gly Arg Gln Thr Tyr<br>                1005                1010                1015 | 3138 |
| GAT GAC ATA GAA GTT CAA GTG ACA GAT GTC AAC TGT TGT CCT AGC TAC<br>Asp Asp Ile Glu Val Gln Val Thr Asp Val Asn Cys Cys Pro Ser Tyr<br>                1020                1025                1030 | 3186 |
| ACC ATA CGT GCA TTT GAT GTC ACA CAT CTG AAG AGG AAA GAA ACA CAG<br>Thr Ile Arg Ala Phe Asp Val Thr His Leu Lys Arg Lys Glu Thr Gln<br>                1035                1040                1045 | 3234 |
| AAG GTA TAT CAG TAT CAA TAT CAC AAG TGG AAT GGA TTG GAT GTT CCA<br>Lys Val Tyr Gln Tyr Gln Tyr His Lys Trp Asn Gly Leu Asp Val Pro<br>                1050                1055                1060 | 3282 |
| GAA GAC CCC AAA GAT TTA GTC GAT ATG ATT CTA AGC CTT AAA CAA AAA<br>Glu Asp Pro Lys Asp Leu Val Asp Met Ile Leu Ser Leu Lys Gln Lys<br>1065                1070                1075                1080 | 3330 |
| GTG CCA TCC AGA CCA GCC TCT GAG GAC AGC AGG AAC AGC CGC AGC GTC<br>Val Pro Ser Arg Pro Ala Ser Glu Asp Ser Arg Asn Ser Arg Ser Val<br>                1085                1090                1095 | 3378 |
| CCA TTT GTC ATC CAC TGC TGT GAT GGA TCG CAG CAG ACC TGG TGT GTT<br>Pro Phe Val Ile His Cys Cys Asp Gly Ser Gln Gln Thr Trp Cys Val<br>                1100                1105                1110 | 3426 |
| TTG TGC TTG ATG ACC CTC TTG GAA AGT GCA GAA ACT GAA GAA GTA ATA<br>Leu Cys Leu Met Thr Leu Leu Glu Ser Ala Glu Thr Glu Glu Val Ile<br>                1115                1120                1125 | 3474 |
| GAT GTT TTC CAA GTA GTA AAA GCT CTT CGT CGC AGC AGG CTG GGA GTG<br>Asp Val Phe Gln Val Val Lys Ala Leu Arg Arg Ser Arg Leu Gly Val<br>                1130                1135                1140 | 3522 |
| GTC TCC ACC TTT GAA CAA TAC CAA TTT CTA TAT GAC ACC ATT GCT CGT<br>Val Ser Thr Phe Glu Gln Tyr Gln Phe Leu Tyr Asp Thr Ile Ala Arg<br>1145                1150                1155                1160 | 3570 |
| ACC TAC CCT GCC CAG AAT GGA CAA ATA AAG AAC ATC CAT CAG GAA GAT<br>Thr Tyr Pro Ala Gln Asn Gly Gln Ile Lys Asn Ile His Gln Glu Asp<br>                1165                1170                1175 | 3618 |
| AAG GTT GAA TTT TGC AAC GAA GTA GAG AAA AAA GAT CAG GAA AGT GAT<br>Lys Val Glu Phe Cys Asn Glu Val Glu Lys Lys Asp Gln Glu Ser Asp<br>                1180                1185                1190 | 3666 |
| TTG ATC ACT ATT GAC CTT ACT CCA TCA ACT CCA GAG GAA AAT GAT GCT<br>Leu Ile Thr Ile Asp Leu Thr Pro Ser Thr Pro Glu Glu Asn Asp Ala<br>                1195                1200                1205 | 3714 |
| CCT GAA TGT TGC GAT GAT TTT AAG GCT GCA GAT ACC AAT AAG GGG ACA<br>Pro Glu Cys Cys Asp Asp Phe Lys Ala Ala Asp Thr Asn Lys Gly Thr<br>                1210                1215                1220 | 3762 |
| GAA AGT TCT ACA AAT GGG CCT ACA ACT CCA GTT TTA ACT T AGAATTTTTT<br>Glu Ser Ser Thr Asn Gly Pro Thr Thr Pro Val Leu Thr<br>1225                1230                1235 | 3812 |
| TTTAAGTAAA AAGTGTATTT TCATACCAAA CAAATCTTAA CCACAGTAAG AAACTTATGA | 3872 |
| TTTTTCCCCC TCCCTTTTGG AAAACATTTA TGTCGGATTT TCAAAGGTAC AAATTTAAAG | 3932 |

TGATACTTGA AACTTCTAAA GAGTGACAAA GAACTGT 3969

( 2 ) INFORMATION FOR SEQ ID NO:2:

( i ) SEQUENCE CHARACTERISTICS:
        ( A ) LENGTH: 1237 amino acids
        ( B ) TYPE: amino acid
        ( D ) TOPOLOGY: linear ( i i ) MOLECULE TYPE: protein ( v i ) ORIGINAL SOURCE:
        ( A ) ORGANISM: Gallus domesticus
        ( B ) STRAIN: DT40

( x i ) SEQUENCE DESCRIPTION: SEQ ID NO:2:

```
Met Phe Leu Cys Leu Lys Leu Leu Ala Phe Gly Val Ala Phe Leu Cys
 1               5                  10                  15

Gln Asp Ala Phe Ala Gln Ala Gly Asn Asp Asn Leu Thr Ser Ala Ser
             20                  25                  30

Ser Leu Ser Ser Thr Leu Pro Thr Pro Thr Arg Ser Thr Ser Phe Ser
             35                  40                  45

Pro Pro Ser Thr Thr Ala Gly Val Gln Pro Ala Ser Thr Gly Ala Ser
     50                  55                  60

Pro Thr Ala Ser Thr His Leu Ser Thr His Ser Gly Ser Gly Pro Thr
 65                  70                  75                  80

Thr Gly Leu Gly His Leu Gln His Ser Ser Pro Ala Ala Leu Thr Thr
                 85                  90                  95

Arg Thr Leu Thr Ala Phe His Gln Thr Val Ser Asp Tyr Tyr Ser Ser
                100                 105                 110

Thr Ser Leu His Asn Thr Thr Ser Pro Val Ile Thr Pro Ala Ser Thr
            115                 120                 125

Glu Thr Ile Pro Thr Ser Thr Ile Glu Ser Ala Thr Thr Thr Glu Glu
130                 135                 140

Pro Cys Asp Asn Ser Ile Asp Tyr Gly Asn Ile Glu Glu Lys Asn Asn
145                 150                 155                 160

Ser Ala Glu Val Thr Leu Lys Asn Leu Lys Glu Asn Arg Ile Tyr Asp
                165                 170                 175

Ile Leu Leu Glu Asp Gly Lys Ser Leu Ser Val Asn Ala Ser Asn Asn
            180                 185                 190

Ile Val Met Leu Asn Trp Cys Arg Arg Tyr Thr Val Gln Ser Arg Ser
            195                 200                 205

Cys Lys Val Met Tyr Leu Thr Ile Pro Pro Asp Glu Lys Arg Tyr Thr
    210                 215                 220

Phe Gly Ala Lys Ser Ile Gly Asn Asp Asn Ala Thr Leu Arg Leu Asn
225                 230                 235                 240

Ser Leu Cys Ile Asp Cys Glu Asp Val Cys Ser Asn Val Thr Val Ser
                245                 250                 255

Cys Lys Thr Asn Ser Ile Asn Ser Gly Gly Thr Gly Asn Leu Thr Gly
            260                 265                 270

Ser Tyr Glu Leu Met Lys His Asp Ile Asn Ala Asp Asn Ile Thr Ile
            275                 280                 285

Leu Ser Leu Ser Ser Asp Ser Glu Tyr Leu Cys Arg Val Thr Val Arg
    290                 295                 300

Phe Phe Glu Lys Asn Phe Thr Lys Glu Val Asn Ile Thr Thr Asp Tyr
305                 310                 315                 320

Asp Ala Pro Lys Ala Pro Glu Asn Leu Thr Val His Pro Thr Asp Arg
                325                 330                 335
```

-continued

| | | | | | | | | | | | | | | |
|---|---|---|---|---|---|---|---|---|---|---|---|---|---|---|
| Asn | Val | Thr | Val<br>340 | Thr | Trp | Met | Lys | Pro<br>345 | Thr | Gly | Thr | Leu<br>350 | Glu | Lys | His |
| Ile | Asp | Gly<br>355 | Tyr | Thr | Val | Glu | Cys<br>360 | Asn | Asn | Thr | Ser | Gln<br>365 | Asn | Val | Asn |
| Arg | Asn<br>370 | Glu | Thr | Ser | Phe | Thr<br>375 | Cys | Gly | Asp | Leu | Glu<br>380 | Pro | Tyr | Ser | Thr |
| Gly<br>385 | Ser | Val | Ser | Val | Arg<br>390 | Ala | Phe | Lys | Lys | Ser<br>395 | Lys | Tyr | Lys | Asn | Lys<br>400 |
| Asn | Phe | Glu | Gly | Glu<br>405 | Lys | Val | Asn | Gly | Ser<br>410 | Phe | Gln | Thr | Lys | Pro<br>415 | Ala |
| Lys | Pro | Glu | Asn<br>420 | Val | Thr | Asp | Phe<br>425 | Lys | Leu | Thr | Leu | Leu<br>430 | Ala | Asp | Asn |
| Thr | Val | Lys<br>435 | Val | Ala | Cys | Arg<br>440 | Ser | Gln | Lys | Val | Tyr<br>445 | Gly | Asn | Glu | Thr |
| Lys | Phe<br>450 | Lys | Leu | Ser | Trp<br>455 | Asn | Ser | Ser | Asn | Ser<br>460 | Gly | Glu | Asn | Gln |
| Arg<br>465 | Lys | Asn | Glu | Cys | Asn<br>470 | Phe | Thr | Val | Arg | Asp<br>475 | Leu | Ser | Tyr | Leu | Thr<br>480 |
| Lys | Tyr | Thr | Phe | Lys<br>485 | Ile | Ser | Val | Phe | Asn<br>490 | Gly | Val | Tyr | Thr | Gly<br>495 | Asp |
| Ser | Val | Cys | Glu<br>500 | Ile | Tyr | Thr | Arg | Tyr<br>505 | Asn | Ser | Arg | Ala | Leu<br>510 | Ile |
| Ile | Phe | Leu<br>515 | Val | Phe | Leu | Ile | Val<br>520 | Val | Thr | Ser | Ile | Ala<br>525 | Leu | Leu | Leu |
| Val | Leu<br>530 | Tyr | Lys | Ile | Tyr | Asp<br>535 | Leu | His | Gln | Lys | Lys<br>540 | Leu | Ser | Asn | Ser |
| Ser<br>545 | Glu | Val | Ile | Ser | Leu<br>550 | Val | Ala | Val | Lys | Asp<br>555 | Asp | Glu | Arg | Gln | Leu<br>560 |
| Leu | Asn | Ile | Glu | Pro<br>565 | Ile | Pro | Ser | Glu | Lys<br>570 | Leu | Leu | Glu | Thr | Tyr<br>575 | Lys |
| Arg | Lys | Ile | Ala | Asp<br>580 | Glu | Gly | Arg | Leu<br>585 | Phe | Leu | Asp | Glu | Phe<br>590 | Gln | Ser |
| Ile | Pro | Arg<br>595 | Ile | Phe | Thr | Lys | Phe<br>600 | Pro | Met | Lys | Glu | Ala<br>605 | Lys | Arg | Ser |
| His | Asn<br>610 | Gln | Asn | Lys | Asn | Arg<br>615 | Tyr | Ile | Asp | Ile | Leu<br>620 | Pro | Tyr | Asp | His |
| Asn<br>625 | Arg | Val | Glu | Leu | Ser<br>630 | Glu | Ile | Pro | Gly | Asp<br>635 | Pro | Gly | Ser | Asp | Tyr<br>640 |
| Ile | Asn | Ala | Ser | Tyr<br>645 | Ile | Asp | Gly | Phe | Lys<br>650 | Glu | Pro | Arg | Lys | Tyr<br>655 | Ile |
| Ala | Ala | Gln | Gly<br>660 | Pro | Lys | Asp | Glu | Thr<br>665 | Thr | Asp | Asp | Phe | Trp<br>670 | Arg | Met |
| Ile | Trp | Glu<br>675 | Gln | Lys | Ala | Thr | Ile<br>680 | Ile | Val | Met | Val | Thr<br>685 | Arg | Cys | Glu |
| Glu | Gly<br>690 | Asn | Arg | Asn | Lys | Cys<br>695 | Ala | Gln | Tyr | Gly | Pro<br>700 | Ser | Met | Glu | Asn |
| Gly<br>705 | Ser | Ala | Thr | Tyr | Gly<br>710 | Asp | Ile | Thr | Val | Lys<br>715 | Ile | Asn | Glu | Ser | Lys<br>720 |
| Ile | Cys | Pro | Asp | Tyr<br>725 | Ile | Ile | Gln | Lys | Leu<br>730 | His | Ile | Thr | Asn | Gly<br>735 | Arg |
| Glu | Arg | Thr | Ser<br>740 | Gly | Arg | Asp | Val | Thr<br>745 | His | Ile | Gln | Phe | Thr<br>750 | Ser | Trp |
| Pro | Asp | His | Gly | Val | Pro | Glu | Asp | Pro | His | Leu | Leu | Leu | Lys | Leu | Arg |

-continued

|     |     |     |     |     | 755 |     |     |     |     | 760 |     |     |     |     | 765 |     |     |
| --- | --- | --- | --- | --- | --- | --- | --- | --- | --- | --- | --- | --- | --- | --- | --- | --- | --- |

Arg Arg Val Asn Ala Leu Ser Asn Phe Phe Ser Gly Pro Ile Val Val
      770                     775                     780

His Cys Ser Ala Gly Val Gly Arg Thr Gly Thr Tyr Ile Gly Ile Asp
785                     790                     795                     800

Ala Met Leu Glu Gly Leu Asp Ala Glu Gly Arg Val Asp Val Tyr Gly
                    805                     810                     815

Tyr Val Val Lys Leu Arg Arg Gln Arg Cys Leu Met Val Gln Val Glu
              820                     825                     830

Ser Gln Tyr Ile Leu Ile His Gln Ala Leu Val Glu Tyr His Gln Tyr
          835                     840                     845

Gly Glu Thr Glu Val Ser Leu Ser Glu Leu His Ser Tyr Leu Asn Asn
850                     855                     860

Leu Lys Arg Lys Asp Pro Ser Glu Pro Ser Leu Leu Glu Ala Lys
865                     870                     875                     880

Phe Gln Arg Leu Pro Ser Tyr Lys Gly Trp Arg Thr Gln Asn Thr Gly
                    885                     890                     895

Asn Arg Glu Glu Asn Lys Asn Lys Asn Arg Ser Ala Asn Thr Ile Pro
              900                     905                     910

Tyr Asp Phe Asn Arg Val Pro Ile Arg Ser Glu Glu Glu Gln Ser Lys
          915                     920                     925

Glu Gly Glu His Asp Ser Glu Asp Ser Ser Asp Ser Asp Ser Asp Cys
930                     935                     940

Glu Glu Ser Ser Arg Tyr Ile Asn Ala Ser Phe Ile Thr Gly Tyr Trp
945                     950                     955                     960

Gly Pro Lys Ala Met Ile Ala Thr Gln Gly Pro Leu Gln Glu Thr Ile
                    965                     970                     975

Ser Asp Phe Trp Gln Met Val Phe Gln Arg Lys Val Lys Val Ile Val
              980                     985                     990

Met Leu Thr Glu Leu Lys Glu Gly Asp Gln Glu Leu Cys Ala Gln Tyr
          995                     1000                    1005

Trp Gly Glu Gly Arg Gln Thr Tyr Asp Asp Ile Glu Val Gln Val Thr
          1010                    1015                    1020

Asp Val Asn Cys Cys Pro Ser Tyr Thr Ile Arg Ala Phe Asp Val Thr
1025                    1030                    1035                    1040

His Leu Lys Arg Lys Glu Thr Gln Lys Val Tyr Gln Tyr Gln Tyr His
                    1045                    1050                    1055

Lys Trp Asn Gly Leu Asp Val Pro Glu Asp Pro Lys Asp Leu Val Asp
              1060                    1065                    1070

Met Ile Leu Ser Leu Lys Gln Lys Val Pro Ser Arg Pro Ala Ser Glu
          1075                    1080                    1085

Asp Ser Arg Asn Ser Arg Ser Val Pro Phe Val Ile His Cys Cys Asp
1090                    1095                    1100

Gly Ser Gln Gln Thr Trp Cys Val Leu Cys Leu Met Thr Leu Leu Glu
1105                    1110                    1115                    1120

Ser Ala Glu Thr Glu Glu Val Ile Asp Val Phe Gln Val Val Lys Ala
                    1125                    1130                    1135

Leu Arg Arg Ser Arg Leu Gly Val Val Ser Thr Phe Glu Gln Tyr Gln
              1140                    1145                    1150

Phe Leu Tyr Asp Thr Ile Ala Arg Thr Tyr Pro Ala Gln Asn Gly Gln
          1155                    1160                    1165

Ile Lys Asn Ile His Gln Glu Asp Lys Val Glu Phe Cys Asn Glu Val
1170                    1175                    1180

```
Glu  Lys  Lys  Asp  Gln  Glu  Ser  Asp  Leu  Ile  Thr  Ile  Asp  Leu  Thr  Pro
1185                1190                     1195                          1200

Ser  Thr  Pro  Glu  Glu  Asn  Asp  Ala  Pro  Glu  Cys  Cys  Asp  Asp  Phe  Lys
               1205                          1210                     1215

Ala  Ala  Asp  Thr  Asn  Lys  Gly  Thr  Glu  Ser  Ser  Thr  Asn  Gly  Pro  Thr
               1220                     1225                     1230

Thr  Pro  Val  Leu  Thr
          1235
```

(2) INFORMATION FOR SEQ ID NO:3:

(i) SEQUENCE CHARACTERISTICS:
        (A) LENGTH: 57 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:3:

```
Ile  Glu  Glu  Lys  Asn  Asn  Ser  Ala  Glu  Val  Thr  Leu  Lys  Asn  Leu  Glu
1                   5                        10                          15

Asn  Arg  Ile  Tyr  Asp  Ile  Leu  Leu  Glu  Asp  Gly  Lys  Ser  Leu  Ser  Val
               20                       25                      30

Asn  Ala  Ser  Asn  Asn  Ile  Val  Met  Leu  Asn  Trp  Cys  Arg  Arg  Tyr  Thr
               35                  40                       45

Val  Gln  Ser  Arg  Ser  Cys  Val  Met  Tyr
          50                  55
```

(2) INFORMATION FOR SEQ ID NO:4:

(i) SEQUENCE CHARACTERISTICS:
        (A) LENGTH: 104 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:4:

```
Leu  Thr  Ile  Pro  Pro  Asp  Glu  Lys  Arg  Tyr  Thr  Phe  Gly  Ala  Lys  Ser
1                   5                        10                          15

Ile  Gly  Asn  Asp  Asn  Ala  Thr  Leu  Arg  Leu  Asn  Ser  Leu  Cys  Ile  Asp
               20                       25                      30

Cys  Glu  Asp  Val  Ser  Asn  Val  Thr  Val  Ser  Cys  Lys  Thr  Asn  Ser  Ile
          35                       40                       45

Asn  Ser  Gly  Gly  Thr  Gly  Asn  Leu  Thr  Gly  Ser  Tyr  Glu  Leu  Met  Lys
          50                       55                       60

His  Asp  Ile  Asn  Ala  Asp  Asn  Ile  Thr  Ile  Leu  Leu  Ser  Ser  Asp  Ser
65                       70                       75                       80

Glu  Tyr  Leu  Cys  Arg  Val  Thr  Val  Arg  Phe  Phe  Glu  Lys  Asn  Phe  Thr
                    85                       90                       95

Lys  Glu  Val  Asn  Ile  Thr  Thr  Asp
               100
```

( 2 ) INFORMATION FOR SEQ ID NO:5:

( i ) SEQUENCE CHARACTERISTICS:
        ( A ) LENGTH: 64 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:5:

```
Ile Ser Thr Thr Thr Ile Ala Thr Thr Pro Lys Pro Thr Cys Asp Glu
 1               5                   10                  15

Lys Tyr Ala Asn Ile Thr Val Asp Tyr Leu Tyr Asn Lys Glu Thr Lys
                20                  25                  30

Leu Phe Thr Ala Lys Leu Asn Val Asn Glu Asn Val Glu Cys Gly Asn
            35                  40                  45

Asn Thr Cys Thr Asn Asn Glu Val His Asn Leu Thr Glu Cys Lys Asn
            50                  55                  60
```

( 2 ) INFORMATION FOR SEQ ID NO:6:

( i ) SEQUENCE CHARACTERISTICS:
        ( A ) LENGTH: 108 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:6:

```
Ile Ser His Asn Ser Cys Thr Ala Pro Asp Lys Thr Leu Ile Leu Asp
 1               5                   10                  15

Val Pro Pro Gly Val Glu Lys Phe Gln Leu His Asp Cys Thr Gln Val
                20                  25                  30

Glu Lys Ala Asp Thr Thr Ile Cys Leu Lys Trp Lys Asn Ile Glu Thr
            35                  40                  45

Phe Thr Cys Asp Thr Gln Asn Ile Thr Tyr Arg Phe Gln Cys Gly Asn
            50                  55                  60

Met Ile Phe Asp Asn Lys Glu Ile Lys Leu Glu Asn Leu Glu Pro Glu
 65                  70                  75                  80

His Glu Tyr Lys Cys Asp Ser Glu Ile Leu Tyr Asn Asn His Lys Phe
                85                  90                  95

Thr Asn Ala Ser Lys Ile Ile Lys Thr Asp Phe Gly
            100                 105
```

( 2 ) INFORMATION FOR SEQ ID NO:7:

( i ) SEQUENCE CHARACTERISTICS:
        ( A ) LENGTH: 66 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:7:

| Asp | Tyr | Asp | Ala | Asn | Asp | Asp | Ile | Val | Asn | Glu | Tyr | Asp | Thr | Thr | Tyr |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Leu | Asp | Asp | Ile | Ala | Lys | Arg | Leu | Asn | Lys | Glu | Asn | Lys | Gly | Leu | Asn |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Leu | Thr | Ser | Thr | Asp | Ala | Ser | Thr | Leu | Phe | Ser | Trp | Cys | Ala | Phe | Glu |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

| Val | Asn | Ala | Lys | Gly | Tyr | Ser | Asp | Val | Cys | Asp | Ile | Phe | Thr | Lys | Asp |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Glu | Leu |
|-----|-----|
| 65  |     |

( 2 ) INFORMATION FOR SEQ ID NO:8:

( i ) SEQUENCE CHARACTERISTICS:
    ( A ) LENGTH: 113 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:8:

| Val | His | Tyr | Ser | Tyr | Tyr | Gln | Asp | Leu | His | Thr | Tyr | Tyr | His | Glu | Gly |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Pro | Gly | Tyr | Asp | Ile | Ile | Lys | Ser | Val | Gly | Ser | Asn | Leu | Phe | Asn | Ala |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Ser | Val | Lys | Leu | Leu | Lys | Gln | Ser | Glu | Ile | Gln | Asp | Gln | Lys | Val | Trp |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

| Leu | Ser | Phe | Thr | His | Asp | Thr | Asp | Ile | Leu | Asp | Phe | Leu | Thr | Thr | Ala |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Gly | Ile | Ile | Asp | Asp | Lys | Asn | Asn | Leu | Thr | Ala | Glu | Thr | Val | Pro | Phe |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Met | Gly | Asn | Thr | Phe | His | Arg | Ser | Trp | Tyr | Val | Pro | Gln | Gly | Ala | Arg |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Val | Tyr | Thr | Glu | Lys | Phe | Gln | Cys | Ser | Asn | Asp | Thr | Tyr | Val | Arg | Tyr |
|-----|-----|-----|-----|-----|-----|-----|-----|-----|-----|-----|-----|-----|-----|-----|-----|
|     |     |     | 100 |     |     |     |     | 105 |     |     |     |     | 110 |     |     |

| Ile |
|-----|
|     |

( 2 ) INFORMATION FOR SEQ ID NO:9:

( i ) SEQUENCE CHARACTERISTICS:
    ( A ) LENGTH: 66 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:9:

| Met | Lys | Thr | Ala | Asn | Asp | Asp | Ile | Leu | Asp | Lys | Tyr | Asp | Thr | Thr | Tyr |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Leu | Asp | Asp | Ile | Ala | Lys | Arg | Leu | Asn | Lys | Glu | Asn | Lys | Gly | Leu | Asn |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

|     |     | Leu | Thr | Ser<br>35 | Lys | Asp | Ala | Asn | Thr<br>40 | Leu | Phe | Ala | Trp | Cys<br>45 | Ala | Tyr | Glu |
|-----|-----|-----|-----|-----|-----|-----|-----|-----|-----|-----|-----|-----|-----|-----|-----|-----|-----|

Leu Asn Ala Arg Gly Tyr Ser Asp Val Cys Asp Ile Phe Thr Glu Asp
        50                  55                  60

Glu Leu
65

( 2 ) INFORMATION FOR SEQ ID NO:10:

( i ) SEQUENCE CHARACTERISTICS:
          ( A ) LENGTH: 113 amino acids
          ( B ) TYPE: amino acid
          ( C ) STRANDEDNESS: single
          ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:10:

Val Arg Tyr Ser Tyr Gly Gln Asp Leu Val Ser Phe Tyr Gln Asp Gly
1               5                   10                  15

Pro Gly Tyr Asp Met Ile Arg Ser Val Gly Ala Asn Leu Phe Asn Ala
            20                  25                  30

Thr Leu Lys Leu Leu Lys Gln Ser Glu Thr Gln Asp Leu Lys Val Trp
        35                  40                  45

Leu Ser Phe Thr His Asp Thr Asp Ile Leu Asp Tyr Leu Thr Thr Ala
    50                  55                  60

Gly Ile Ile Asp Asp Lys Asn Asn Leu Thr Ala Glu Thr Val Pro Phe
65                  70                  75                  80

Met Gly Asn Thr Phe His Arg Ser Trp Tyr Val Pro Gln Gly Ala Arg
                85                  90                  95

Val Tyr Thr Glu Lys Phe Gln Cys Ser Asn Asp Thr Tyr Val Arg Tyr
            100                 105                 110

Ile ( 2 ) INFORMATION FOR SEQ ID NO:11:

( i ) SEQUENCE CHARACTERISTICS:
          ( A ) LENGTH: 105 amino acids
          ( B ) TYPE: amino acid
          ( C ) STRANDEDNESS: single
          ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:11:

Ile Glu Ala Arg Ile Lys Glu Val Ser Ala Gln Trp Asp Gln Leu Lys
1               5                   10                  15

Asp Leu Ala Ala Phe Cys Lys Lys Asn Leu Gln Asp Ala Glu Asn Phe
            20                  25                  30

Phe Gln Phe Gln Gly Asp Ala Asp Leu Lys Ala Trp Leu Gln Asp
        35                  40                  45

Ala His Arg Leu Leu Ser Gly Glu Asp Val Gly Gln Asp Glu Gly Ala
    50                  55                  60

Thr Arg Ala Leu Gly Lys Lys His Lys Asp Phe Leu Glu Glu Leu Glu 65                  70                  75                  80

Glu  Ser  Arg  Gly  Val  Met  Glu  Lys  Leu  Glu  Gln  Gln  Ala  Gln  Gly  Phe
               85                       90                       95

Pro  Glu  Glu  Phe  Arg  Asp  Ser  Pro  Asp
              100                      105

( 2 ) INFORMATION FOR SEQ ID NO:12:

( i ) SEQUENCE CHARACTERISTICS:
        ( A ) LENGTH: 106 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v i ) ORIGINAL SOURCE:
        ( A ) ORGANISM: Gallus domesticus
        ( B ) STRAIN: DT40

( x i ) SEQUENCE DESCRIPTION: SEQ ID NO:12:

Val  Lys  Gln  Tyr  Gln  Asp  His  Leu  Asn  Thr  Arg  Trp  Gln  Ala  Phe  Gln
1                   5                        10                       15

Thr  Leu  Val  Ser  Glu  Arg  Arg  Glu  Ala  Val  Asp  Ser  Ala  Leu  Arg  Val
               20                       25                       30

His  Thr  Leu  Cys  Val  Asp  Cys  Glu  Glu  Thr  Ser  Lys  Trp  Ile  Thr  Asp
               35                       40                       45

Lys  Thr  Lys  Val  Val  Glu  Ser  Thr  Lys  Asp  Pro  Gly  Arg  Asp  Leu  Ala
               50                       55                       60

Gly  Ile  Ile  Ala  Ile  Gln  Arg  Lys  Leu  Ser  Gly  Leu  Glu  Arg  Asp  Val
65                       70                       75                       80

Ala  Ala  Ile  Gln  Ala  Arg  Val  Asp  Ala  Leu  Glu  Arg  Glu  Ser  Gln  Gln
               85                       90                       95

Leu  Met  Asp  Ser  His  Pro  Glu  Gln  Lys  Glu
              100                      105

( 2 ) INFORMATION FOR SEQ ID NO:13:

( i ) SEQUENCE CHARACTERISTICS:
        ( A ) LENGTH: 106 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:13:

Val  Arg  Glu  Lys  Met  Glu  Arg  Leu  Asp  Asn  Asn  Trp  Thr  Ala  Leu  Leu
1                   5                        10                       15

Glu  Leu  Trp  Asp  Glu  Arg  His  Arg  Lys  Tyr  Glu  Gln  Cys  Leu  Asp  Phe
               20                       25                       30

His  Leu  Phe  Tyr  Arg  Asp  Ser  Glu  Gln  Val  Asp  Ser  Trp  Met  Ser  Arg
               35                       40                       45

Gln  Glu  Ala  Phe  Leu  Glu  Asn  Glu  Asp  Leu  Gly  Asn  Ser  Leu  Gly  Ser
               50                       55                       60

Ala  Glu  Ala  Leu  Leu  Gln  Lys  His  Glu  Asp  Phe  Glu  Glu  Ala  Phe  Thr

```
                65                      70                     75                      80
            Ala Gln Glu Glu Lys Ile Ile Thr Val Asp Lys Thr Ala Thr Lys Leu
                            85                      90                      95

Ile Gly Asp Asp His Tyr Asp Ser Glu Met
                            100                     105
```

( 2 ) INFORMATION FOR SEQ ID NO:14:

( i ) SEQUENCE CHARACTERISTICS:
        ( A ) LENGTH: 99 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:14:

```
            Val Ala Ser Leu Trp Glu Glu Leu Leu Glu Ala Thr Lys Gln Lys Gly
            1               5                       10                      15

Thr Gln Leu His Glu Ala Asn Gln Gln Leu Gln Phe Glu Asn Asn Ala
                            20                      25                      30

Glu Asp Leu Gln Arg Trp Leu Asp Val Glu Trp Gln Val Thr Ser
                            35                      40                      45

Glu Asp Tyr Gly Lys Gly Leu Ala Glu Val Gln Asn Arg Leu Arg Lys
                            50                      55                      60

His Gly Leu Leu Glu Ser Ala Val Ala Ala Arg Gln Asp Gln Val Asp
            65                      70                      75                      80

Ile Leu Thr Asp Leu Ala Ala Tyr Phe Glu Ile Gly His Pro Asp
                            85                      90                      95

Ser Lys Asp
```

( 2 ) INFORMATION FOR SEQ ID NO:15:

( i ) SEQUENCE CHARACTERISTICS:
        ( A ) LENGTH: 113 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:15:

```
            Thr Arg Glu Gln Ile Leu Val Lys His Ala Gln Glu Glu Leu Pro Pro
            1               5                       10                      15

Pro Pro Pro Gln Lys Lys Arg Gln Ile Thr Val Asp Ser Glu Ile Arg
                            20                      25                      30

Lys Arg Leu Asp Val Asp Ile Thr Glu Leu His Ser Trp Ile Thr Arg
                            35                      40                      45

Ser Glu Ala Val Leu Gln Ser Pro Glu Phe Ala Ile Phe Arg Lys Glu
                            50                      55                      60

Gly Asn Phe Ser Asp Leu Lys Glu Lys Val Asn Ala Ile Glu Arg Glu
            65                      70                      75                      80

Lys Ala Glu Lys Phe Arg Lys Leu Gln Asp Ala Ser Arg Ser Ala Gln
                            85                      90                      95
```

Ala Leu Val Glu Gln Met Val Asn Glu Gly Val Asn Ala Asp Ser Ile
            100                 105                 110

Lys ( 2 ) INFORMATION FOR SEQ ID NO:16:

( i ) SEQUENCE CHARACTERISTICS:
         ( A ) LENGTH: 101 amino acids
         ( B ) TYPE: amino acid
         ( C ) STRANDEDNESS: single
         ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:16:

Leu Asn Thr Gln Trp Asp His Met Cys Gln Gln Val Tyr Ala Arg Lys
1               5                   10                  15

Glu Ala Leu Lys Gly Gly Leu Glu Lys Thr Val Ser Leu Gln Lys Asp
            20                  25                  30

Leu Ser Glu Met His Glu Trp Met Thr Lys Ala Glu Glu Glu Tyr Leu
        35                  40                  45

Glu Arg Asp Phe Glu Tyr Lys Thr Pro Asp Glu Leu Gln Lys Ala Val
    50                  55                  60

Glu Glu Met Met Pro Ala Lys Glu Glu Ala Leu Gln Lys Glu Thr Lys
65                  70                  75                  80

Val Lys Leu Leu Thr Glu Thr Val Asn Ser Val Ile Ala His Ala Pro
                85                  90                  95

Pro Ser Ala Gln Glu
            100

( 2 ) INFORMATION FOR SEQ ID NO:17:

( i ) SEQUENCE CHARACTERISTICS:
         ( A ) LENGTH: 108 amino acids
         ( B ) TYPE: amino acid
         ( C ) STRANDEDNESS: single
         ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:17:

Ile Asn Gly Lys Trp Glu His Val Arg Gln Leu Val Pro Arg Arg Asp
1               5                   10                  15

Gln Ala Leu Met Glu Glu His Ala Arg Gln Gln Asn Glu Arg Leu
            20                  25                  30

Arg Lys Gln Phe Gly Ala Gln Ala Asn Val Ile Gly Pro Trp Ile Gln
        35                  40                  45

Thr Lys Met Glu Glu Ile Gly Arg Ile Ser Ile Glu Met His Gly Thr
    50                  55                  60

Leu Glu Asp Gln Leu Asn His Leu Arg Gln Tyr Glu Lys Ser Ile Val
65                  70                  75                  80

Asn Thr Lys Pro Lys Ile Asp Gln Leu Glu Gly Gly Asp His Gln Gln
                85                  90                  95

Ile Gln Glu Ala Leu Ile Phe Asp Asn Lys His Thr
            100                 105

( 2 ) INFORMATION FOR SEQ ID NO:18:

( i ) SEQUENCE CHARACTERISTICS:
        ( A ) LENGTH: 93 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:18:

```
Ala  Pro  Lys  Ala  Pro  Glu  Asn  Leu  Thr  Val  His  Pro  Thr  Asp  Arg  Asn
 1               5                        10                       15
Val  Thr  Val  Thr  Trp  Met  Lys  Pro  Thr  Gly  Thr  Leu  Glu  Lys  His  Ile
              20                       25                       30
Asp  Gly  Tyr  Thr  Val  Glu  Cys  Asn  Asn  Thr  Ser  Gln  Asn  Val  Asn  Arg
         35                            40                  45
Asn  Glu  Thr  Ser  Phe  Thr  Cys  Gly  Asp  Leu  Glu  Pro  Tyr  Ser  Thr  Gly
     50                       55                      60
Ser  Val  Ser  Val  Arg  Ala  Phe  Lys  Lys  Ser  Lys  Tyr  Lys  Asn  Lys  Asn
 65                 70                       75                           80
Phe  Glu  Gly  Glu  Lys  Val  Asn  Gly  Ser  Phe  Gln  Thr  Lys
                  85                       90
```

( 2 ) INFORMATION FOR SEQ ID NO:19:

( i ) SEQUENCE CHARACTERISTICS:
        ( A ) LENGTH: 87 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:19:

```
Ser  Pro  Gly  Glu  Pro  Gln  Ile  Ile  Phe  Cys  Arg  Ser  Glu  Ala  Ala  His
 1               5                        10                       15
Gln  Gly  Val  Ile  Thr  Trp  Asn  Pro  Pro  Gln  Arg  Ser  Phe  His  Asn  Phe
              20                       25                       30
Thr  Leu  Cys  Tyr  Ile  Lys  Glu  Thr  Glu  Lys  Asp  Cys  Leu  Asn  Leu  Asp
          35                           40                  45
Lys  Asn  Leu  Ile  Lys  Tyr  Asp  Leu  Gln  Asn  Leu  Lys  Pro  Tyr  Thr  Lys
 50                       55                      60
Tyr  Val  Leu  Ser  Leu  His  Ala  Tyr  Ile  Ile  Ala  Lys  Val  Gln  Arg  Asn
 65                 70                       75                           80
Asn  Gly  Ser  Ala  Ala  Met  Cys
                  85
```

( 2 ) INFORMATION FOR SEQ ID NO:20:

( i ) SEQUENCE CHARACTERISTICS:
        ( A ) LENGTH: 96 amino acids
        ( B ) TYPE: amino acid
        ( C ) STRANDEDNESS: single
        ( D ) TOPOLOGY: linear (i i) MOLECULE TYPE: peptide (i i i) HYPOTHETICAL: NO (i v) ANTI-SENSE: NO (x i) SEQUENCE DESCRIPTION: SEQ ID NO:20:

| Pro | Ser | Ala | Pro | Pro | Gln | Lys | Val | Met | Cys | Val | Ser | Met | Gly | Ser | Thr |
|---|---|---|---|---|---|---|---|---|---|---|---|---|---|---|---|
| 1 | | | | 5 | | | | | 10 | | | | | 15 | |
| Thr | Val | Arg | Val | Ser | Trp | Val | Pro | Pro | Pro | Ala | Asp | Ser | Arg | Asn | Gly |
| | | | 20 | | | | | 25 | | | | | 30 | | |
| Val | Ile | Thr | Gln | Tyr | Ser | Val | Ala | His | Glu | Ala | Val | Asp | Gly | Glu | Asp |
| | | 35 | | | | | 40 | | | | | 45 | | | |
| Arg | Gly | Arg | His | Val | Val | Asp | Gly | Ile | Ser | Arg | Glu | His | Ser | Ser | Trp |
| | 50 | | | | | 55 | | | | | 60 | | | | |
| Asp | Leu | Val | Gly | Leu | Glu | Lys | Trp | Thr | Glu | Tyr | Arg | Val | Trp | Val | Arg |
| 65 | | | | | 70 | | | | | 75 | | | | | 80 |
| Ala | His | Thr | Asp | Val | Gly | Pro | Gly | Pro | Glu | Ser | Ser | Pro | Val | Leu | Val |
| | | | | 85 | | | | | 90 | | | | | 95 | |

(2) INFORMATION FOR SEQ ID NO:21:

(i) SEQUENCE CHARACTERISTICS:
        (A) LENGTH: 92 amino acids
        (B) TYPE: amino acid
        (C) STRANDEDNESS: single
        (D) TOPOLOGY: linear (i i) MOLECULE TYPE: peptide (i i i) HYPOTHETICAL: NO (i v) ANTI-SENSE: NO (x i) SEQUENCE DESCRIPTION: SEQ ID NO:21:

| Pro | Gly | Ala | Pro | Pro | Arg | Asn | Ile | Thr | Ala | Ile | Ala | Thr | Ser | Ser | Thr |
|---|---|---|---|---|---|---|---|---|---|---|---|---|---|---|---|
| 1 | | | | 5 | | | | | 10 | | | | | 15 | |
| Thr | Ile | Ser | Leu | Ser | Trp | Leu | Pro | Pro | Pro | Val | Glu | Arg | Ser | Asn | Gly |
| | | | 20 | | | | | 25 | | | | | 30 | | |
| Arg | Ile | Ile | Tyr | Tyr | Lys | Val | Phe | Phe | Val | Glu | Val | Gly | Arg | Glu | Asp |
| | | 35 | | | | | 40 | | | | | 45 | | | |
| Asp | Glu | Ala | Thr | Thr | Met | Thr | Leu | Asn | Met | Thr | Ser | Ile | Val | Leu | Asp |
| | 50 | | | | | 55 | | | | | 60 | | | | |
| Glu | Leu | Lys | Arg | Trp | Thr | Glu | Tyr | Lys | Ile | Trp | Val | Leu | Ala | Gly | Thr |
| 65 | | | | | 70 | | | | | 75 | | | | | 80 |
| Ser | Val | Gly | Asp | Gly | Pro | Arg | Ser | His | Pro | Ile | Ile | | | | |
| | | | | 85 | | | | | 90 | | | | | | |

(2) INFORMATION FOR SEQ ID NO:22:

(i) SEQUENCE CHARACTERISTICS:
        (A) LENGTH: 83 amino acids
        (B) TYPE: amino acid
        (C) STRANDEDNESS: single
        (D) TOPOLOGY: linear (i i) MOLECULE TYPE: peptide (i i i) HYPOTHETICAL: NO (i v) ANTI-SENSE: NO (x i) SEQUENCE DESCRIPTION: SEQ ID NO:22:

| Val | Pro | Ser | Pro | Val | Lys | Asp | Ile | Gly | Ile | Ser | Thr | Lys | Ala | Asn | Ser |
|---|---|---|---|---|---|---|---|---|---|---|---|---|---|---|---|
| 1 | | | | 5 | | | | | 10 | | | | | 15 | |

| | | | | | | | | | | | | | | | |
|---|---|---|---|---|---|---|---|---|---|---|---|---|---|---|---|
| Leu | Leu | Ile | Ser | Trp | Ser | His | Gly | Ser | Gly | Asn | Val | Glu | Arg | Tyr | Arg |
| | | | 20 | | | | | 25 | | | | | 30 | | |
| Leu | Met | Leu | Met | Asp | Lys | Gly | Ile | Leu | Val | His | Gly | Gly | Val | Val | Asp |
| | | 35 | | | | | 40 | | | | | 45 | | | |
| Lys | His | Ala | Thr | Ser | Tyr | Ala | Phe | His | Gly | Leu | Ser | Pro | Gly | Tyr | Leu |
| | 50 | | | | | 55 | | | | | 60 | | | | |
| Tyr | Asn | Leu | Thr | Val | Met | Thr | Glu | Ala | Ala | Gly | Leu | Gln | Asn | Tyr | Arg |
| 65 | | | | | 70 | | | | | 75 | | | | | 80 |
| Trp | Lys | Leu | | | | | | | | | | | | | |

(2) INFORMATION FOR SEQ ID NO:23:

(i) SEQUENCE CHARACTERISTICS:
        (A) LENGTH: 86 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:23:

| | | | | | | | | | | | | | | | |
|---|---|---|---|---|---|---|---|---|---|---|---|---|---|---|---|
| Pro | Ile | Phe | Ile | Pro | Lys | Val | Glu | Thr | Thr | Gly | Ser | Thr | Ala | Ser | Thr |
| 1 | | | | 5 | | | | | 10 | | | | | 15 | |
| Ile | Thr | Ile | Gly | Trp | Asn | Pro | Pro | Pro | Asp | Leu | Ile | Asp | Tyr | Ile | |
| | | | 20 | | | | | 25 | | | | | 30 | | |
| Gln | Tyr | Tyr | Glu | Leu | Ile | Val | Ser | Glu | Ser | Gly | Glu | Val | Pro | Lys | Val |
| | | 35 | | | | | 40 | | | | | 45 | | | |
| Ile | Glu | Glu | Ala | Ile | Tyr | Gln | Gln | Asn | Ser | Arg | Asn | Leu | Pro | Tyr | Met |
| | 50 | | | | | 55 | | | | | 60 | | | | |
| Phe | Asp | Lys | Leu | Lys | Thr | Ala | Thr | Asp | Tyr | Glu | Phe | Arg | Val | Phe | Ala |
| 65 | | | | | 70 | | | | | 75 | | | | | 80 |
| Cys | Ser | Asp | Leu | Thr | Lys | | | | | | | | | | |
| | | | | 85 | | | | | | | | | | | |

(2) INFORMATION FOR SEQ ID NO:24:

(i) SEQUENCE CHARACTERISTICS:
        (A) LENGTH: 91 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:24:

| | | | | | | | | | | | | | | | |
|---|---|---|---|---|---|---|---|---|---|---|---|---|---|---|---|
| Ile | Pro | Asp | Ser | Val | Gln | Glu | Ser | Ser | Phe | Arg | Ile | Glu | Gly | His | Thr |
| 1 | | | | 5 | | | | | 10 | | | | | 15 | |
| Ser | Ser | Pro | Arg | Ile | Leu | Trp | Asn | Glu | Pro | Pro | Ala | Val | Asp | Trp | Gly |
| | | | 20 | | | | | 25 | | | | | 30 | | |
| Ile | Val | Phe | Tyr | Ser | Val | Glu | Phe | Ser | Ala | His | Ser | Lys | Phe | Leu | Ala |
| | | | 35 | | | | | 40 | | | | | 45 | | |
| Ile | Glu | Gln | Gln | Ser | Leu | Pro | Val | Phe | Thr | Val | Glu | Gly | Leu | Glu | Pro |
| | | | 50 | | | | | 55 | | | | | 60 | | |
| Tyr | Ala | Leu | Phe | Asn | Leu | Ser | Val | Thr | Pro | Tyr | Thr | Tyr | Trp | Gly | Lys |

```
                        65                  70                  75                  80
        Gly Gln Lys Thr Ser Leu Ser Phe Arg Ala Pro
                        85                  90
```

( 2 ) INFORMATION FOR SEQ ID NO:25:

( i ) SEQUENCE CHARACTERISTICS:
        ( A ) LENGTH: 94 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:25:

```
        Thr Thr Gln Pro Leu Asn Val Thr Val Ser Leu Asn Glu Ser Ser Ser
        1               5                   10                  15
        Phe Leu Glu Ile Arg Trp Val Lys Pro Pro Leu Glu Arg Thr His Gly
                        20                  25                  30
        Glu Leu Gln Gly Tyr His Ile Trp His Thr Trp Gln Asp Ser Lys Gly
                    35                  40                  45
        Leu Gln Asn Ile Ser Leu Glu Ala Gln Pro Asn Ala Thr Val Ala Ile
                50                  55                  60
        Leu Pro Val Val Ala Thr Asn Ala Thr Cys Ser Val Arg Val Ala Ala
        65                  70                  75                  80
        Val Thr Lys Gly Gly Val Gly Pro Phe Ser Ser Pro Val Glu
                        85                  90
```

( 2 ) INFORMATION FOR SEQ ID NO:26:

( i ) SEQUENCE CHARACTERISTICS:
        ( A ) LENGTH: 110 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:26:

```
        Pro Pro Ser Ala Pro Arg Asn Leu Ser Phe Ser Ala Ser Gly Thr Gln
        1               5                   10                  15
        Leu Ser Leu Arg Trp Glu Pro Pro Ala Asp Thr Gly Gly Arg Gln Asp
                        20                  25                  30
        Val Arg Tyr Ser Val Arg Cys Ser Gln Cys Gln Gly Thr Ala Gln Asp
                    35                  40                  45
        Gly Gly Pro Cys Gln Pro Cys Gly Val Gly Val His Phe Ser Pro Gly
                50                  55                  60
        Ala Arg Ala Leu Thr Thr Pro Ala Val His Val Asn Gly Leu Glu Pro
        65                  70                  75                  80
        Tyr Ala Asn Tyr Thr Phe Asn Val Glu Ala Gln Asn Gly Val Ser Gly
                        85                  90                  95
        Leu Gly Ser Ser Gly His Ala Ser Thr Ser Val Ser Ile Ser
                        100                 105                 110
```

( 2 ) INFORMATION FOR SEQ ID NO:27:

( i ) SEQUENCE CHARACTERISTICS:
   ( A ) LENGTH: 103 amino acids
   ( B ) TYPE: amino acid
   ( C ) STRANDEDNESS: single
   ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:27:

```
Pro  Pro  Ser  Ala  Pro  His  Tyr  Leu  Thr  Ala  Val  Gly  Met  Gly  Ala  Lys
1              5                        10                            15

Val  Glu  Leu  Arg  Trp  Thr  Pro  Pro  Gln  Asp  Ser  Gly  Gly  Arg  Glu  Asp
          20                       25                           30

Ile  Val  Tyr  Ser  Val  Thr  Cys  Glu  Gln  Cys  Trp  Pro  Glu  Ser  Gly  Glu
          35                       40                           45

Cys  Gly  Pro  Cys  Glu  Ala  Ser  Val  Arg  Tyr  Ser  Glu  Pro  Pro  His  Gly
          50                       55                           60

Leu  Thr  Arg  Thr  Ser  Val  Thr  Val  Ser  Asp  Leu  Glu  Pro  His  Met  Asn
65                       70                           75                      80

Tyr  Thr  Phe  Thr  Val  Glu  Ala  Arg  Asn  Gly  Val  Ser  Gly  Leu  Val  Thr
               85                       90                           95

Ser  Arg  Ser  Phe  Arg  Thr  Ala
               100
```

( 2 ) INFORMATION FOR SEQ ID NO:28:

( i ) SEQUENCE CHARACTERISTICS:
      ( A ) LENGTH: 100 amino acids
      ( B ) TYPE: amino acid
      ( C ) STRANDEDNESS: single
      ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:28:

```
Pro  Pro  Ser  Ala  Pro  Arg  Asn  Val  Ile  Ser  Asn  Ile  Asn  Glu  Thr  Ser
1              5                        10                            15

Val  Ile  Leu  Asp  Trp  Ser  Trp  Pro  Leu  Asp  Thr  Gly  Gly  Arg  Lys  Asp
          20                       25                           30

Ile  Thr  Phe  Asn  Ile  Ile  Cys  Lys  Lys  Cys  Gly  Trp  Asn  Val  Arg  Gln
          35                       40                           45

Cys  Glu  Pro  Cys  Ser  Pro  Asn  Val  Arg  Phe  Leu  Pro  Arg  Gln  Leu  Gly
          50                       55                           60

Leu  Thr  Asn  Thr  Thr  Val  Thr  Val  Thr  Asp  Leu  Leu  Ala  His  Thr  Asn
65                       70                           75                      80

Tyr  Thr  Phe  Glu  Ile  Asp  Ala  Val  Asn  Gly  Val  Ser  Glu  Leu  Ser  Ser
               85                       90                           95

Pro  Pro  Arg  Gln
               100
```

( 2 ) INFORMATION FOR SEQ ID NO:29:

( i ) SEQUENCE CHARACTERISTICS:
      ( A ) LENGTH: 100 amino acids
      ( B ) TYPE: amino acid (C) STRANDEDNESS: single
(D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:29:

| Pro | Pro | Ser | Ser | Pro | Arg | Asn | Val | Ile | Ser | Asn | Ile | Asn | Glu | Thr | Ser |
|---|---|---|---|---|---|---|---|---|---|---|---|---|---|---|---|
| 1 | | | | 5 | | | | | 10 | | | | | 15 | |
| Val | Ile | Leu | Asp | Trp | Ser | Trp | Pro | Leu | Asp | Thr | Gly | Gly | Arg | Lys | Asp |
| | | | 20 | | | | | 25 | | | | | 30 | | |
| Val | Thr | Phe | Asn | Ile | Ile | Cys | Lys | Lys | Cys | Gly | Trp | Asn | Ile | Lys | Gln |
| | | | 35 | | | | 40 | | | | | 45 | | | |
| Cys | Glu | Pro | Cys | Ser | Pro | Asn | Val | Arg | Phe | Leu | Pro | Arg | Gln | Phe | Gly |
| | | 50 | | | | | 55 | | | | | 60 | | | |
| Leu | Thr | Asn | Thr | Thr | Val | Thr | Val | Thr | Asp | Leu | Leu | Ala | His | Thr | Asn |
| 65 | | | | | 70 | | | | | 75 | | | | | 80 |
| Tyr | Thr | Phe | Glu | Ile | Asp | Ala | Val | Asn | Gly | Val | Ser | Glu | Leu | Ser | Ser |
| | | | | 85 | | | | | 90 | | | | | 95 | |
| Pro | Pro | Arg | Gln | | | | | | | | | | | | |
| | | | 100 | | | | | | | | | | | | |

(2) INFORMATION FOR SEQ ID NO:30:

(i) SEQUENCE CHARACTERISTICS:
  (A) LENGTH: 68 amino acids
  (B) TYPE: amino acid
  (C) STRANDEDNESS: single
  (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:30:

| Thr | Gly | Gly | Val | Pro | Ile | Leu | Lys | Tyr | Lys | Ala | Glu | Trp | Lys | Ser | Leu |
|---|---|---|---|---|---|---|---|---|---|---|---|---|---|---|---|
| 1 | | | | 5 | | | | | 10 | | | | | 15 | |
| Gly | Glu | Glu | Ala | Trp | His | Ser | Lys | Trp | Tyr | Asp | Ala | Lys | Gly | Ala | Asn |
| | | | 20 | | | | | 25 | | | | | 30 | | |
| Met | Glu | Gly | Ile | Val | Thr | Ile | Met | Gly | Leu | Lys | Pro | Glu | Thr | Arg | Tyr |
| | | | 35 | | | | | 40 | | | | | 45 | | |
| Ala | Val | Arg | Leu | Ala | Ala | Ile | Asn | Gly | Lys | Gly | Leu | Gly | Glu | Ile | Ser |
| | | 50 | | | | | 55 | | | | | 60 | | | |
| Ala | Ala | Thr | Glu | | | | | | | | | | | | |
| 65 | | | | | | | | | | | | | | | |

(2) INFORMATION FOR SEQ ID NO:31:

(i) SEQUENCE CHARACTERISTICS:
  (A) LENGTH: 91 amino acids
  (B) TYPE: amino acid
  (C) STRANDEDNESS: single
  (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:31:

| | | | | | | | | | | | | | | |
|---|---|---|---|---|---|---|---|---|---|---|---|---|---|---|
| Pro | Leu | Ser | Pro | Pro | Thr | Asn | Leu | His | Leu | Glu | Ala | Asn | Pro | Asp | Thr |
| 1 | | | | 5 | | | | | 10 | | | | | 15 | |
| Gly | Val | Leu | Thr | Val | Ser | Trp | Glu | Arg | Ser | Thr | Thr | Pro | Asp | Ile | Thr |
| | | | 20 | | | | | 25 | | | | | 30 | | |
| Gly | Tyr | Arg | Ile | Thr | Thr | Thr | Pro | Thr | Asn | Gly | Gln | Gln | Gly | Asn | Ser |
| | | 35 | | | | | 40 | | | | | 45 | | | |
| Leu | Asn | Asn | Val | Val | Ala | Asp | Gln | Ser | Ser | Cys | Thr | Phe | Asp | Asn | Leu |
| | 50 | | | | | 55 | | | | | 60 | | | | |
| Ser | Pro | Gly | Leu | Glu | Tyr | Asn | Val | Ser | Val | Tyr | Thr | Val | Lys | Asp | Asp |
| 65 | | | | | 70 | | | | | 75 | | | | | 80 |
| Lys | Glu | Ser | Val | Pro | Ile | Ser | Asp | Thr | Ile | Ile |
| | | | | 85 | | | | | 90 | |

(2) INFORMATION FOR SEQ ID NO:32:

(i) SEQUENCE CHARACTERISTICS:
        (A) LENGTH: 89 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:32:

| | | | | | | | | | | | | | | |
|---|---|---|---|---|---|---|---|---|---|---|---|---|---|---|---|
| Val | Ser | Asp | Val | Pro | Arg | Asp | Ile | Glu | Val | Val | Ala | Ala | Thr | Pro | Thr |
| 1 | | | | 5 | | | | | 10 | | | | | 15 | |
| Ser | Leu | Leu | Ile | Ser | Trp | Asp | Ala | Pro | Ala | Val | Thr | Val | Arg | Tyr | Tyr |
| | | | 20 | | | | | 25 | | | | | 30 | | |
| Arg | Ile | Thr | Tyr | Gly | Glu | Thr | Gly | Gly | Asn | Ser | Pro | Val | Gln | Glu | Phe |
| | | 35 | | | | | 40 | | | | | 45 | | | |
| Thr | Val | Pro | Gly | Ser | Lys | Ser | Thr | Ala | Thr | Ile | Ser | Gly | Leu | Lys | Pro |
| | 50 | | | | | 55 | | | | | 60 | | | | |
| Gly | Val | Asp | Tyr | Thr | Ile | Thr | Val | Tyr | Ala | Val | Thr | Gly | Arg | Gly | Asp |
| 65 | | | | | 70 | | | | | 75 | | | | | 80 |
| Ser | Pro | Ala | Ser | Ser | Lys | Pro | Ile | Ser |
| | | | | 85 | | | | |

(2) INFORMATION FOR SEQ ID NO:33:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:33:

CCTCTGATTC TCACCACTGT T          21

(2) INFORMATION FOR SEQ ID NO:34:

(i) SEQUENCE CHARACTERISTICS:
        (A) LENGTH: 19 base pairs
        (B) TYPE: nucleic acid
        (C) STRANDEDNESS: single ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:34:

TGTATATCTT CTGCACCAA 19

( 2 ) INFORMATION FOR SEQ ID NO:35:

( i ) SEQUENCE CHARACTERISTICS:
            ( A ) LENGTH: 19 base pairs
            ( B ) TYPE: nucleic acid
            ( C ) STRANDEDNESS: single
            ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:35:

CCATGTTTTT GTGCCTTAA 19

( 2 ) INFORMATION FOR SEQ ID NO:36:

( i ) SEQUENCE CHARACTERISTICS:
            ( A ) LENGTH: 18 base pairs
            ( B ) TYPE: nucleic acid
            ( C ) STRANDEDNESS: single
            ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:36:

CGTGATGACT GGTGTGGT 18

( 2 ) INFORMATION FOR SEQ ID NO:37:

( i ) SEQUENCE CHARACTERISTICS:
            ( A ) LENGTH: 22 amino acids
            ( B ) TYPE: amino acid
            ( C ) STRANDEDNESS: single
            ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:37:

Ala Leu Ile Ile Phe Leu Val Phe Leu Ile Val Val Thr Ser Ile Ala
        1               5                   10                  15

Leu Leu Leu Val Leu Tyr
                    20

TRANSMEMBRANE TYROSINE PHOSPHATASE AND METHODS OF USE THEREOF

This application is a Division of application Ser. No. 08/241,853 filed May 12, 1994, U.S. Pat No. 5,693,488.

The research leading to the present invention was supported in part with Grant Nos. CA44356 and CA01605 from the National Cancer Institute. Accordingly, the Government may have certain rights in the invention.

FIELD OF THE INVENTION

The present invention relates to regulation and control of cellular processes by transmembrane protein tyrosine phosphatases, and to ligands that agonize or antagonize tyrosine phosphorylation mediated by such tyrosine phosphatases. This invention further relates to diagnosis and therapy based on the activity of such ligands.

BACKGROUND OF THE INVENTION

Protein tyrosine phosphorylation is one of the mechanisms cells use to control proliferation and differentiation (1, 2) (the full length citation of references cited herein by number can be found at the end of the specification, preceding the SEQUENCE LISTING). The level of protein tyrosine phosphorylation is regulated by protein tyrosine kinases (PTKs) and protein tyrosine phosphatases (PTPs). PTPs represent a diverse family of enzymes, including both transmembrane and nontransmembrane types. All PTPs share highly homologous catalytic domains—PTP domains (about 230 amino acids)—that have no similarity with protein serine/threonine phosphatases (3). All the nontransmembrane PTPs identified so far contain only one PTP domain. Most transmembrane PTPs have two tandem PTP domains in their cytoplasmic portions, except for HPTPβ and DPTP10D which have only one PTP domain (4). Usually, any pair of PTP domains are 30–50% identical at the amino acid level, with a higher score within the transmembrane or non-transmembrane type (average 46%) and a lower score between these two types (average 35%). In some cases, identity between two distinct PTPs can reach as high as 74%, e.g., PTP1B and TCPTP or PTPα and PTPε (5).

In contrast to the homologous PTP domains, the non-catalytic sequences of PTPs vary considerably in size and structure. For example, some nontransmembrane PTPs contain hydrophobic carboxyl-terminal sequences as in PTP1B and T-cell PTP (6–10); others have sequences similar to other known proteins, such as the SH2 domains of SH-PTP1 and 2, and the cytoskeletal protein domains of PTP-MEG and PTP-H1 (11–16). These structural similarities appear to be involved in localization and/or regulation of these PTPs. On the other hand, transmembrane PTPs differ greatly in their extracellular portions. Some have structures similar to carbonate hydrolase, as in PTPζ (or PTPβ) (17, 18); others have fibronectin type III (FN-III) domains and immunoglobulin (Ig)-like domains, as in LAR, PTPδ, PTPμ, PTPκ, DLAR and DPTP, which are similar to cell adhesion molecules including N-CAM (4). Recently, the extracellular domain of PTPμ has been shown to form a homodimer in vitro (1,9).

Although little is known about the ligands of transmembrane PTPs, features in their extracellular domains may help in predicting protein properties and in searching for their physiological ligands.

Accordingly, there is a need in the art for identification and characterization of additional members of the family of protein tyrosine phosphatases.

There is a further need in the art to identify ligands and ligand analogs or mimetics, including agonists and antagonists, of protein tyrosine phosphatases.

Accordingly, there is a need to identify strategies for identifying ligands of protein tyrosine phosphatases.

The present invention is directed to these and other needs in the art.

The citation of any reference herein is not an admission that such reference is available as prior art to the instant invention.

SUMMARY OF THE INVENTION

The present invention provides a novel transmembrane protein tyrosine phosphatase-λ (PTPλ), including fragments, derivatives, and analogs thereof; nucleic acids encoding the same; antibodies to the PTPλ; and methods for identifying ligands to the PTPλ of the invention.

Accordingly, in a first aspect, the present invention relates to a nucleic acid molecule that encodes an extracytoplasmic domain of a transmembrane protein tyrosine phosphatase comprising a serine-threonine-proline-rich region, a spectrin repeat, and a fibronectin III module. In one embodiment, the nucleic acid has the sequence of a naturally occurring coding sequence for PTPλ. In another embodiment, the nucleic acid has a sequence that encodes a naturally occurring PTPλ protein, but has an altered nucleotide sequence, i.e., with by substitution of degenerate codons. In yet another embodiment, the nucleic acid is hybridizable, preferably under moderately stringent conditions, more preferably under conditions of high stringency, to a nucleic acid having a hybridizable portion of a sequence as set forth in FIG. 2A–2C (SEQ ID NO: 1), or the complementary sequence thereof, and encodes a polypeptide that is a derivative or analog of a naturally occurring PTPλ.

The present invention advantageously provides a nucleotide sequence of a nucleic acid that encodes a specific PTPλ of the invention, which nucleotide sequence is shown in FIG. 2A–2C and in SEQ ID NO: 1. Thus, in one aspect, the invention provides a nucleic acid hybridizable to the nucleic acid having a sequence encoding the extracytoplasmic domain, as depicted in FIG. 2A–2C (SEQ ID NO: 1, nucleotides number 154 to 1617). In a further embodiment, the nucleotide sequence of the nucleic acid is the same as nucleotides number 154 to 1617. The invention further provides nucleic acids having sequences complementary to the above-mentioned sequences.

A nucleic acid molecule of the invention can be DNA or RNA, including synthetic variants thereof having phosphate or phosphate analog, e.g., thiophosphate, bonds. Both single stranded and double stranded sequences are contemplated by the invention.

In a preferred aspect, the nucleic acid molecule also includes a nucleotide sequence that encodes a transmembrane domain oriented 3' to the nucleotide sequence encoding the extracytoplasmic domain, and a nucleotide sequence that encodes a receptor-type protein tyrosine phosphatase domain oriented 3' to the nucleotide sequence encoding the transmembrane domain, wherein all three nucleotide sequences are in an open reading frame. Such a protein tyrosine phosphatase may comprise two catalytic domains in tandem. Such a construct can be a chimeric construct. In another embodiment, the receptor-type protein tyrosine phosphatase domain is hybridizable to a nucleic acid having a sequence selected from the group consisting of the sequence shown in FIG. 2A–2C (SEQ ID NO:1) from nucleotide number 1684 to nucleotide number 3802 and the sequence complementary thereto. In a specific embodiment, the invention provides a nucleic acid for a full length PTPλ.

In another embodiment, a nucleic acid molecule of the invention is a chimeric molecule having a nucleotide sequence that encodes a transmembrane domain oriented 3' to the nucleotide sequence encoding the extracytoplasmic domain, and a nucleotide sequence that encodes a receptor-type protein tyrosine kinase domain oriented 3' to the nucleotide sequence encoding the transmembrane domain, wherein all three nucleotide sequences are in an open reading frame. In a specific embodiment, the receptor-type protein tyrosine kinase domain is selected from the group consisting of cEyk protein tyrosine kinase domain and epidermal growth factor receptor protein tyrosine kinase domain.

In specific embodiments, the transmembrane domain mentioned above is hybridizable to a nucleic acid having a sequence selected from the group consisting of the sequence shown in FIG. 2A–2C (SEQ ID NO: 1) from nucleotide number 1618 to nucleotide number 1683 and the sequence complementary thereto.

The present invention further provides nucleic acid molecules for use as molecular probes, or as primers for polymerase chain reaction (PCR) amplification, i.e., synthetic or natural oligonucleotides having a sequence corresponding to a portion of the sequence shown in FIG. 2A–2C (SEQ ID NO: 1). In particular, the invention contemplates a nucleic acid molecule having at least about 10 nucleotides, wherein a sequence of the nucleic acid molecule corresponds to a nucleotide sequence of the same number of nucleotides in the nucleotide sequence of FIG. 2A–2C (SEQ ID NO: 1), or a sequence complementary thereto. More preferably, the nucleic acid sequence of the molecule has at least 15 nucleotides. Most preferably, the nucleic acid sequence has at least 20 nucleotides. In an embodiment of the invention in which the oligonucleotide is a probe, the oligonucleotide is detectably labeled, e.g., with a radionuclide (such as $^{32}p$), or an enzyme.

In further aspects, the present invention provides a cloning vector, which comprises the nucleic acid of the invention; and a bacterial, insect, or a mammalian expression vector, which comprises the nucleic acid molecule of the invention, operatively associated with an expression control sequence. Accordingly, the invention further relates to a bacterial cell or a mammalian transfected or transformed with an appropriate expression vector.

In another aspect, the present invention relates to proteins encoded by the nucleic acids of the invention. In particular, the invention is directed to a protein encoded by the nucleic acids described above, which protein comprises an extracytoplasmic domain of a transmembrane protein tyrosine phosphatase, which extracytoplasmic domain comprises a serine-threonine-proline-rich region, a spectrin repeat, and a fibronectin III domain. In a further embodiment, the protein comprises a transmembrane domain oriented C-terminal to the extracytoplasmic domain, and a protein tyrosine phosphatase domain or a protein tyrosine kinase domain oriented C-terminal to the transmembrane domain. Preferably, the protein tyrosine kinase domain is selected from the group consisting of cEyk: protein tyrosine kinase domain and epidermal growth factor receptor protein tyrosine kinase domain. In a specific embodiment, the present invention provides a purified, full length transmembrane PTPλ.

In yet a further aspect, the invention is directed to an antibody that binds to the protein tyrosine phosphatase as described above. Such an antibody can be a polygonal or a monoclonal antibody. In a specific Example, infra, the present invention provides a rabbit polyclonal antibody reactive with the protein tyrosine phosphatase extracytoplasmic domain. The invention is also directed to antibodies that bind to the ligand binding site of the protein tyrosine phosphatase. Accordingly, the invention relates to antibodies that can act as an antagonist or an agonist of a ligand to the protein tyrosine phosphatase.

The invention is also directed to a method for identifying a ligand of a protein tyrosine phosphatase having a serine-threonine-proline-rich region, a spectrin repeat, and a fibronectin III domain in an extracytoplasmic domain. In one embodiment, the method comprises contacting candidate ligands with the protein tyrosine phosphatase, or extracellular domain thereof; detecting binding of the protein with a ligand; and determining the structure of the ligand. In another embodiment, the method comprises contacting a cell that expresses the extracellular domain of the protein tyrosine phosphatase with candidate ligands; detecting a phenotypic change in the cell in response to binding of a ligand; and determining the structure of the ligand. Accordingly, the invention further relates to a molecule that is an agonist or an antagonist of a ligand to a protein tyrosine phosphatase of the invention.

Accordingly, a primary object of the present invention is to provide a nucleic acid, in particular a DNA, that encodes a novel protein tyrosine phosphatase-λ, or a fragment, derivative or analog thereof.

Yet a further object of the invention is to provide a cloning vector and an expression vector for such a nucleic acid molecule.

Still another object of the invention is to provide a recombinant cell line that contains such an expression vector.

It is also an object of the invention to provide the protein tyrosine phosphatase-λ, and fragments thereof, in particular the extracytoplasmic domain thereof.

Yet a further object of the invention is to provide antibodies to such proteins.

Another important object of the invention is to provide ligand agonists or antagonists of the protein tyrosine phosphatase-λ of the invention. The agonists and antagonists can be natural ligands or ligand mimetics.

These and other objects of the present invention can be better appreciated and understood by reference to the following drawings and detailed description of the invention.

BRIEF DESCRIPTION OF THE DRAWINGS

FIG. 1A–1C Sequencing strategy and schematic structure of ChPTPλ. (A) A linear map of ChPTPλ cDNA, including some restriction sites. Clone 6a and 1a were obtained from screening a chicken brain cDNA library. Fragments 6b and 6c's were obtained from 5' RACE. p1, p2, p3 and pn are primers λp1, λp2, λp3 and λpn, correspondingly. Arrows indicate 5'-to-3' orientation. (B) Upper panel: schematic structure of ChPTPλ protein. Shaded boxes represent functional domains, and thick lines represent non-coding sequences. SP, signal peptide; S/T/P, Ser/Thr/Pro-region; FNIII, fibronectin type-III domain; TM, transmembrane span; PDI and PDII, PTP domains I and II, respectively. The lower panel shows five ChPTPλ isoforms a–e. The N-terminal 114 amino acids are dissected into four segments—I, II, III and IV. Numbers indicate the starting residue of each segment. Amino acid sequences after the fourth segment are identical among isoforms. (C) Total RNA was isolated from DT40 cells, and the first strand cDNA was reverse-transcribed with random primers. PCR was performed using λpn and λp3 (lane b) or λp2 (lane c) primers. Lane a is DNA molecular weight marker 1kb ladder.

FIG. 2A–2C. Nucleotide (SEQ ID NO:1) and deduced amino acid (SEQ ID NO:2) sequences of ChPTPλ. The 3969 bp ChPTPλ cDNA encodes 1237 amino acids, terminated at nucleotide 3806 marked by an asterisk. A putative signal peptide (residue −21 to −1) and a transmembrane region (residue 489 to 510) are boxed. In the extracellular domain, potential sites (NXS/T) for N-linked glycosylation are underlined; cysteine residues are in bold-face; and the altrnatively spliced segments are included in ( ). In the cytoplasmic domain, two PTP domains are delineated by [], and the core sequences are underlined. Amino acids are identified by the single-letter code. The numbers above the lines indicate nucleotides, and the numbers at right indicate amino acids.

FIG. 3. Alignment of the spectrin-like repeats. The amino acid sequence (starting form residue 134) of ChPTPλ (ChPTP1-1, SEQ ID NO:3; AND ChPTP1-2, SEQ ID NO:4) is aligned with the spectrin-like repeat-containing proteins, including human CD45 (CD45-1, SEQ ID NO:5; CD45-2, SEQ ID NO:6), phosphatases (PHO5-1, SEQ ID NO:7; PHO5-2, SEQ ID NO:8; PHO3-1, SEQ ID NO:9; PHO3-2, SEQ ID NO: 10), β-spectrin (b-spec-5, SEQ ID NO: 11; b-spec-7, SEQ ID NO:12), α-spectrin (a-spec-5, SEQ ID NO:13; a-spec-7, SEQ ID NO: 14), dystrophin (DMD-4, SEQ ID NO: 15; DMD-8, SEQ ID NO: 16), and actinin (actinin-3, SEQ ID NO: 17). The numbers after proteins indicate the repeat number. The single-letter amino acid code is used. The conserved residues are highlighted by black boxes. FIG. 4A and 4B. Alignment of the FN-III domains. The amino acid sequence of ChPTPλ (starting from residue 301, SEQ ID NO: 18) is aligned with the FN-III domains of other proteins, including PTPs (CD45, SEQ ID NO: 19; LAR, SEQ ID NO:20; DLAR, SEQ ID NO: 21; HPTPδ, SEQ ID NO: 22; DPTP, SEQ ID NO:23), PTKs (Ros, SEQ ID NO:24; Ryk, SEQ ID NO:25; Eph, SEQ ID NO:26; Eck, SEQ ID NO:27; Mek4, SEQ ID NO:28; Hek, SEQ ID NO:29), cell adhesion molecules (N-CAM, SEQ ID NO:30), and adhesion matrix proteins (FN-21, SEQ ID NO:31; FN-24, SEQ ID NO:32). The numbers after FN indicate the repeat number. The single-letter amino acid code is used. The conserved residues are in black boxes.

FIG. 5. Tissue distribution of ChPTPλ. 10 μg of polyA⁺ RNA was prepared from adult chicken tissues, separated in 1% formaldehyde-denaturing agarose gel. After transfer, the membrane was hybridized with ³²P-labeled fragment 6a (FIG. 1A). RSV/CEF, Rous Sarcoma Virus-infected chicken embryo fibroblasts; DT40, chicken preB-cell line. 18S rRNA was probed as a loading control (lower panel).

DETAILED DESCRIPTION OF THE INVENTION

Figure 1C:
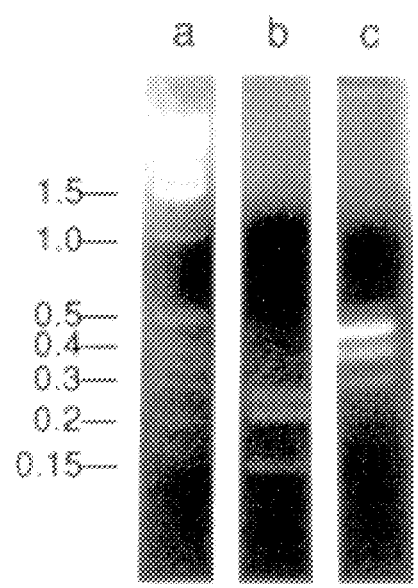

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984).

Therefore, if appearing herein, the following terms shall have the definitions set out below.

A "replicon" is any genetic element (e.g., plasmid, chromosome, virus) that functions as an autonomous unit of DNA replication in vivo, i.e., capable of replication under its own control.

A "vector" is a replicon, such as plasmid, phage or cosmid, to which another DNA segment may be attached so as to bring about the replication of the attached segment.

A "cassette" refers to a segment of DNA that can be inserted into a vector at specific restriction sites. The segment of DNA encodes a polypeptide of interest, and the cassette and restriction sites are designed to ensure insertion of the cassette in the proper reading frame for transcription and translation.

A cell has been "transfected" by exogenous or heterologous DNA when such DNA has been introduced inside the cell. A cell has been "transformed" by exogenous or heterologous DNA when the transfected DNA effects a phenotypic change. Preferably, the transforming DNA should be integrated (covalently linked) into chromosomal DNA making up the genome of the cell.

"Heterologous" DNA refers to DNA not naturally located in the cell, or in a chromosomal site of the cell. Preferably, the heterologous DNA includes a gene foreign to the cell.

A "clone" is a population of cells derived from a single cell or common ancestor by mitosis.

A "nucleic acid molecule" refers to the phosphate ester polymeric form of ribonucleosides (adenosine, guanosine, uridine or cytidine; "RNA molecules") of deoxyribonucleosides (deoxyadenosine, deoxyguanosine, deoxythymidine, or deoxycytidine; "DNA molecules") in either single stranded form, or a double-stranded helix. Double stranded DNA—DNA, DNA-RNA and RNA—RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra). The conditions of temperature and ionic strength determine the "stringency" of the hybridization. For preliminary screening for homologous nucleic acids, low stringency hybridization conditions, corresponding to a $T_m$ of 55°, can be used, e.g., 5×SSC, 0.1% SDS, 0.25% milk, and no formamide; or 30% formamide, 5×SSC, 0.5% SDS). Moderate stringency hybridization conditions correspond to a higher $T_m$, e.g., 40% formamide, with 5× or 6×SCC. High stringency hybridization conditions correspond to the highest $T_m$, e.g., 50% formamide, 5× or 6×SCC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50–0.51). For hybridization with shorter nucleic acids, i.e., oligonucleotides, the position of mismatches becomes more important, and the length of the oligonucleotide determines its specificity (see Sambrook et al., supra, 11.7–11.8). Preferably a minimum length for a hybridizable nucleic acid is at least about 10 nucleotides; more preferably at least about 15 nucleotides; most preferably the length is at least about 20 nucleotides.

"Homologous recombination" refers to the insertion of a foreign DNA sequence of a vector in a chromosome. Preferably, the vector targets a specific chromosomal site for homologous recombination. For specific homologous recombination, the vector will contain sufficiently long regions of homology to sequences of the chromosome to allow complementary binding and incorporation of the vector into the chromosome. Longer regions of homology, and greater degrees of sequence similarity, may increase the efficiency of homologous recombination.

A DNA "coding sequence" is a double-stranded DNA sequence which is transcribed and translated into a polypeptide in a cell in vitro or in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. If the coding sequence is intended for expression in a eukaryotic cell, a polyadenylation signal and transcription termination sequence will usually be located 3' to the coding sequence.

Transcriptional and translational control sequences are DNA regulatory sequences, such as promoters, enhancers, terminators, and the like, that provide for the expression of a coding sequence in a host cell. In eukaryotic cells, polyadenylation signals are control sequences.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A coding sequence is "under the control" of transcriptional and translational control sequences in a cell when RNA polymerase transcribes the coding sequence into mRNA, which is then trans-RNA spliced and translated into the protein encoded by the coding sequence.

A "signal sequence" is included at the beginning of the coding sequence of a protein to be expressed on the surface of a cell. This sequence encodes a signal peptide, N-terminal to the mature polypeptide, that directs the host cell to translocate the polypeptide. The term "translocation signal sequence" is used herein to refer to this sort of signal sequence. Translocation signal sequences can be found associated with a variety of proteins native to eukaryotes and prokaryotes, and are often functional in both types of organisms.

A molecule is "antigenic" when it is capable of specifically interacting with an antigen recognition molecule of the immune system, such as an immunoglobulin (antibody) or T cell antigen receptor. An antigenic polypeptide contains at least about 5, and preferably at least about 10, amino acids. An antigenic portion of a molecule can be that portion that is immunodominant for antibody or T cell receptor recognition, or it can be a portion used to generate an antibody to the molecule by conjugating the antigenic portion to a carrier molecule for immunization. A molecule that is antigenic need not be itself immunogenic, i.e., capable of eliciting an immune response without a carrier.

A composition comprising "A" (where "A" is a single protein, DNA molecule, vector, recombinant host cell, etc.) is substantially free of "B" (where "B" comprises one or more contaminating proteins, DNA molecules, vectors, etc.) when at least about 75% by weight of the proteins, DNA, vectors (depending on the category of species to which A and B belong) in the composition is "A". Preferably, "A" comprises at least about 90% by weight of the A+B species in the composition, most preferably at least about 99% by weight. It is also preferred that a composition, which is substantially free of contamination, contain only a single molecular weight species having the activity or characteristic of the species of interest.

The phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly For injectable solutions. Suitable pharmaceutical carriers are described in "Remington's Pharmaceutical Sciences" by E. W. Martin.

The phrase "therapeutically effective amount" is used herein to mean an amount sufficient to reduce by at least about 15 percent, preferably by at least 50 percent, more preferably by at least 90 percent, and most preferably prevent, a clinically significant deficit in the activity, function and response of the host. Alternatively, a therapeutically effective amount is sufficient to cause an improvement in a clinically significant condition in the host. The term "adjuvant" refers to a compound or mixture that enhances the immune response to an antigen. An adjuvant can serve as a tissue depot that slowly releases the antigen and also as a lymphoid system activator that non-specifically enhances the immune response (Hood et al., *Immunology, Second Ed.*, 1984, Benjamin/Cummings: Menlo Park, Calif., p. 384). Often, a primary challenge with an antigen alone, in the absence of an adjuvant, will fail to elicit a humoral or cellular immune response. Adjuvants include, but are not limited to, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, keyhole limpet hemocyanins, dinitrophenol, and potentially useful human adjuvants such as BCG (bacille Calmette-Guerin) and Corynebacterium parvum. Preferably, the adjuvant is pharmaceutically acceptable.

As used herein, the term "serine-threonine-proline (Ser/Thr/Pro or S-T-P) rich region" refers to a region of a protein that contains an unusually high number of occurrences of serine or threonine and proline residues;. In a specific embodiment, these three residues make up greater than 40% of the amino acids in the particular region of the protein.

As used herein, the term "spectrin repeat" refers to a spectrin-like sequence, e.g., an identifiable consensus sequence found in proteins such as a-spectrin, β-spectrin, dystrophin, and α-actinin. Spectrin repeats of the sort identified herein have heretofore never been identified on phosphatases.

As used herein the term "fibronectin type-III (FN-III or fibronectin III)" domain (or module) has the meaning generally understood by those of ordinary skill in the art.

As used herein, the term "transmembrane domain" has the meaning ordinarily ascribed to it by those of skill in the art, e.g., a portion of a protein consisting almost exclusively of non-polar, primarily hydrophobic amino acid residues, that provides for partitioning of a protein into a lipid bilayer membrane. A transmembrane domain can be about 20±5 amino acids in length.

As used herein, the term "receptor-type protein tyrosine phosphatase domain" and "transmembrane protein tyrosine phosphatase domain" refer to the intracytoplasmic domain having tyrosine phosphatase activity that is found as part of a receptor structure. Binding of ligand to the receptor activates the tyrosine phosphatase activity of the domain. A receptor-type tyrosine phosphatase domain can have one, two, or more tyrosine phosphatase catalytic domains. Examples of receptor-type protein tyrosine phosphatases include, but are not limited to, human CD45, and the PTPλ disclosed herein (having two catalytic domains), and HPTPβ and DPTP10D (having one catalytic domain).

As used herein, the term "receptor-type protein tyrosine kinase domain" and "transmembrane protein tyrosine kinase domain" refer to the intracytoplasmic domain having tyrosine kinase activity that is found as part of a receptor structure. Binding of ligand to the receptor activates the tyrosine kinase activity of the domain. Examples of receptor-type protein tyrosine phosphatases include, but are not limited to, platelet-derived growth factor receptor, epidermal growth factor receptor, cEyk, and vEyk.

In its primary aspect, the present invention is directed to transmembrane protein tyrosine phosphatases (PTPs), nucleic acids encoding such transmembrane PTPs, recombinant expression of transmembrane PTPs of the invention, methods for identifying ligands that agonize or antagonize tyrosine phosphorylation mediated by such PTPs, and ligand agonists and antagonists of such PTPs. A PTP of the invention, termed herein a PTPX, is characterized by having a unique extracellular domain containing a Ser/Thr/Pro-rich region, spectrin-like repeats, a FN-III domain, and an alternatively spliced N-terminus. The PTPλ of the invention can be of avian or mammalian origin. Preferably, the PTPλ of the invention is of human origin. However, the PTPλ of the invention is not human or murine CD45.

The present invention is based, in part, on the isolation and characterization of the first chicken transmembrane PTP, called ChPTPλ. Accordingly, the present invention is directed specifically to chicken PTPλ, and broadly to homologs of ChPTPλ in other species. A PTPλ of the invention has a unique extracellular domain containing a Ser/Thr/Pro-rich region, spectrin-like repeats, a FN-III domain, and an alternatively spliced N-terminus. The expression of ChPTPλ in various tissues and cells has been examined. ChPTPλ was shown to have a tyrosine-specific phosphatase activity and the basic characteristics of this enzyme were studied. Thus, PTPλ of the invention has a tissue distribution that distinguishes it from human CD45.

The present invention is divided into the following sections, which relate to identification of genes encoding a PTPX of the invention or a functionally active fragment, derivative, or analog thereof; expression of recombinant genes encoding a PTPλ of the invention, or a functionally active fragment, derivative or analog thereof; identification of such polypeptides by biochemical, immunological, and functional criteria; preparation of antibodies to such polypeptides; identification of ligands that agonize or antagonize the functional activity of a PTPλ of the invention; and methods of treatment of diseases or disorders with the nucleic acids, polypeptides, or ligand agonists or antagonists of the invention.

Genes Encoding PTP, or Fragments, Derivatives or Analogs Thereof

The present invention contemplates isolation of a gene encoding a functional portion of a PTP of the invention, including a full length PTP, from any animal, particularly mammalian or avian, and more particularly human or chicken, source. As used herein, the term "gene" refers to an assembly of nucleotides that encode a polypeptide, and includes cDNA and genomic DNA nucleic acids.

A gene encoding PTP whether genomic DNA or cDNA, can be isolated from any source, particularly from a human cDNA or genomic library. Methods for obtaining the PTP gene are well known in the art, as described above (see, e.g., Sambrook et al., 1989, supra).

Accordingly, any animal cell potentially can serve as the nucleic acid source for the molecular cloning of a PTP gene. The DNA may be obtained by standard procedures known in the art from cloned DNA (e.g., a DNA "library"), by chemical synthesis, by cDNA cloning, or by the cloning of genomic DNA, or fragments thereof, purified from the desired cell (See, for example, Sambrook et al., 1989, supra; Glover, D. M. (ed.), 1985, DNA Cloning: A Practical Approach, MRL Press, Ltd., Oxford, U.K. Vol. I, II). Clones derived from genomic DNA may contain regulatory and intron DNA regions in addition to coding regions; clones derived from cDNA will not contain intron sequences. Whatever the source, the gene should be molecularly cloned into a suitable vector for propagation of the gene.

In the molecular cloning of the gene from genomic DNA, DNA fragments are generated, some of which will encode the desired gene. The DNA may be cleaved at specific sites using various restriction enzymes. Alternatively, one may use DNAse in the presence of manganese to fragment the DNA, or the DNA can be physically sheared, as for example, by sonication. The linear DNA fragments can then be separated according to size by standard techniques, including but not limited to, agarose and polyacrylamide gel electrophoresis and column chromatography.

Once the DNA fragments are generated, identification of the specific DNA fragment containing the desired PTP gene may be accomplished in a number of ways. For example, if an amount of a portion of a PTP gene or its specific RNA, or a fragment thereof, is available and can be purified and labeled, the generated DNA fragments may be screened by nucleic acid hybridization to the labeled probe (Benton and Davis, 1977, Science 196:180; Grunstein and Hogness, 1975, Proc. Natl. Acad. Sci. U.S.A. 72:3961). The present invention provides such nucleic acid probes, which can be conveniently prepared from the specific sequences disclosed herein, e.g., a probe having a nucleotide sequence corresponding to at least a 10, and preferably a 15, nucleotide fragment of the sequence depicted in FIG. 2A–2C (SEQ ID NO: 1). Preferably, a fragment is selected that is highly unique to the PTP of the invention. Those DNA fragments with substantial homology to the probe will hybridize. As noted above, the greater the degree of homology, the more stringent hybridization conditions can be used. In a specific embodiment, low stringency hybridization conditions are used to identify a homologous PTPλ. However, in a preferred aspect, a nucleic acid encoding a PTPλ of the invention will hybridize to a nucleic acid having a nucleotide sequence depicted in FIG. 2A–2C (SEQ ID NO: 1), or a hybridizable fragment thereof, under moderately stringent conditions; more preferably, it will hybridize under high stringency conditions.

Further selection can be carried out on the basis of the properties of the gene, e.g., if the gene includes sequences encoding a Ser/Thr/Pro-rich region, spectrin-like repeats, a FN-III domain, etc.

In a specific embodiment, infra, a specific cDNA fragment encoding the PTP domain of human CD45 was used as a probe to screen λgt10 phage plaques of a chicken embryonic cDNA library. Accordingly, the present invention contemplates isolation of homologs of ChPTPλ from other species using such a probe.

Alternatively, the presence of the gene may be detected by assays based on the physical, chemical, or immunological properties of its expressed product. For example, cDNA clones, or DNA clones which hybrid-select the proper mRNAs, can be selected which produce a protein that, e.g., has similar or identical electrophoretic migration, isoelectric focusing behavior, proteolytic digestion maps, tyrosine phosphatase activity or antigenic properties as known for ChPTPλ. For example, the antibodies of the instant invention can conveniently be used to screen for homologs of ChPTPλ from other sources, preferably human.

A PTP gene of the invention can also be identified by mRNA selection, i.e., by nucleic acid hybridization followed by in vitro translation. In this procedure, fragments are used to isolate complementary mRNAs by hybridization. Such DNA fragments may represent available, purified ChPTPλ DNA. Immunoprecipitation analysis or functional assays (e.g., tyrosine phosphatase activity) of the in vitro translation products of the products of the isolated mRNAs identifies the mRNA and, therefore, the complementary DNA fragments, that contain the desired sequences. In addition, specific mRNAs may be selected by adsorption of polysomes isolated from cells to immobilized antibodies specifically directed against a PTP, in particular ChPTPλ.

A radiolabelled PTP cDNA can be synthesized using the selected mRNA (from the adsorbed polysomes) as a template. The radiolabelled mRNA or cDNA may then be used as a probe to identify homologous PTP DNA fragments from among other genomic DNA fragments.

The present invention also relates to cloning vectors containing genes encoding analogs and derivatives of the PTP of the invention, that have the same or homologous functional activity as ChPTPλ, and homologs thereof from other species. The production and use of derivatives and analogs related to PTP are within the scope of the present invention. In a specific embodiment, the derivative or analog is functionally active, i.e., capable of exhibiting one or more functional activities associated with a full-length, wild-type PTP of the invention.

In a particularly preferred aspect, the derivative of PTP of the invention is a chimeric construct consisting of a PTP extracellular domain and a tyrosine kinase intracellular domain. The tyrosine kinase portion can be selected from the group consisting of, though not limited to, cEyk receptor-type protein tyrosine kinase domain (e.g., Jia and Hanafusa, 1994, J. Biol. Chem. 269:1839–44) and EGFR tyrosine kinase domain. Presumably, binding of ligand to the PTP extracellular domain can activate the tyrosine kinase activity. Such a construct is attractive because tyrosine kinase activity is more readily assayed than tyrosine phosphatase activity.

In another embodiment, chimeric PTP polypeptide fragments can be prepared, e.g., a GST fusion protein for expression in bacteria. Expression of fragments of PTP as a fusion protein can facilitate stable expression, or allow for purification based on the properties of the fusion partner.

PTP derivatives can be made by altering encoding nucleic acid sequences by substitutions, additions or deletions that provide for functionally equivalent molecules. Preferably, derivatives are made that have enhanced or increased functional activity relative to the native PTP. Alternatively, such derivatives may encode soluble fragments of the PTP extracellular domain that have the same or greater affinity for the natural ligand of the PTP of the invention. Such soluble derivatives may be potent inhibitors of ligand binding to PTP.

Due to the degeneracy of nucleotide coding sequences, other DNA sequences which encode substantially the same amino acid sequence as a PTP gene may be used in the practice of the present invention. These include but are not limited to nucleotide sequences comprising all or portions of PTP genes which are altered by the substitution of different codons that encode the same amino acid residue within the sequence, thus producing a silent change. Likewise, the PTP derivatives of the invention include, but are not limited to, those containing, as a primary amino acid sequence, all or part of the amino acid sequence of a PTP protein including altered sequences in which functionally equivalent amino acid residues are substituted for residues within the sequence resulting in a conservative amino acid substitution. For example, one or more amino acid residues within the sequence can be substituted by another amino acid of a similar polarity, which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid.

The genes encoding PTP derivatives and analogs of the invention can be produced by various methods known in the art. The manipulations which result in their production can occur at the gene or protein level. For example, the cloned PTP gene sequence can be modified by any of numerous strategies known in the art (Sambrook et al., 1989, supra). The sequence can be cleaved at appropriate sites with restriction endonuclease(s), followed by further enzymatic modification if desired, isolated, and ligated in vitro. In the production of the gene encoding a derivative or analog of PTP, care should be taken to ensure that the modified gene remains within the same translational reading frame as the PTP gene, uninterrupted by translational stop signals, in the gene region where the desired activity is encoded.

Additionally, the PTP-encoding nucleic acid sequence can be mutated in vitro or in vivo, to create and/or destroy translation, initiation, and/or termination sequences, or to create variations in coding regions and/or form new restriction endonuclease sites or destroy preexisting ones, to facilitate further in vitro modification. Preferably, such mutations enhance the functional activity of the mutated PTP gene product. Any technique for mutagenesis known in the art can be used, including but not limited to, in vitro site-directed mutagenesis (Hutchinson, C., et al., 1978, J. Biol. Chem. 253:6551; Zoller and Smith, 1984, DNA 3:479–488; Oliphant et al., 1986, Gene 44:177; Hutchinson et al., 1986, Proc. Natl. Acad. Sci. U.S.A. 83:710), use of TAB® linkers (Pharmacia), etc. PCR techniques are preferred for site directed mutagenesis (see Higuchi, 1989, "Using PCR to Engineer DNA", in *PCR Technology: Principles and Applications for DNA Amplification,* H. Erlich, ed., Stockton Press, Chapter 6, pp. 61–70).

Expression of PTP Polypeptides

The nucleotide sequence coding for a PTP, or functional fragment, derivative or analog thereof, can be inserted into an appropriate expression vector, i.e., a vector which contains the necessary elements for the transcription and translation of the inserted protein-coding sequence. Such elements are termed herein a "promoter." Thus, the nucleic acid encoding the PTP of the invention is operationally associated with a promoter in an expression vector of the invention. Both cDNA and genomic sequences can be cloned and expressed under control of such regulatory sequences.

An expression vector also preferably includes a replication origin.

The necessary transcriptional and translational signals can be provided on a recombinant expression vector, or they may be supplied by the native gene encoding a PTP and/or its flanking regions. Potential host-vector systems include but are not limited to mammalian cell systems infected with virus (e.g., vaccinia virus, adenovirus, etc.); insect cell systems infected with virus (e.g., baculovirus); microorganisms such as yeast containing yeast vectors; or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used.

A recombinant PTP of the invention, or functional fragment, derivative or analog thereof, may be expressed chromosomally, after integration of the PTPλ coding sequence by recombination. In this regard, any of a number of amplification systems may be used to achieve high levels of stable gene expression (See Sambrook et al., 1989, supra).

The cell into which the recombinant vector comprising the nucleic acid encoding the PTP is cultured in an appropriate cell culture medium under conditions that provide for expression of the PTP by the cell. If full length PTP is expressed, the expressed protein will be an integral membrane protein. If a fragment of PTP lacking a membrane binding domain is expressed, the expressed PTP can then be recovered from the culture according to methods well known in the art. Such methods are described in detail, infra.

Any of the methods previously described for the insertion of DNA fragments into a cloning vector may be used to construct expression vectors containing a gene consisting of appropriate transcriptional/translational control signals and the protein coding sequences. These methods may include in vitro recombinant DNA and synthetic techniques and in vivo recombination (genetic recombination).

Expression of a PTP protein may be controlled by any promoter/enhancer element known in the art, but these regulatory elements must be functional in the host selected for expression. Promoters which may be used to control PTP gene expression include, but are not limited to, the SV40 early promoter region (Benoist and Chambon, 1981, Nature 290:304–310), the promoter contained in the 3'long terminal repeat of Rous sarcoma virus (Yamamoto, et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et al., 1982, Nature 296:39–42); prokaryotic expression vectors such as the β-lactamase promoter (Villa-Kamaroff, et al., 1978, Proc. Natl. Acad. Sci. U.S.A. 75:3727–3731), or the tac promoter (DeBoer, et al., 1983, Proc. Natl. Acad. Sci. U.S.A. 80:21–25); see also "Useful proteins from recombinant bacteria" in Scientific American, 1980, 242:74–94; promoter elements from yeast or other fungi such as the Gal 4 promoter, the ADC (alcohol dehydrogenase) promoter, PGK (phosphoglycerol kinase) promoter, alkaline phosphatase promoter; and the animal transcriptional control regions, which exhibit tissue specificity and have been utilized in transgenic animals.

Expression vectors containing a nucleic acid encoding a PTP of the invention can be identified by four general approaches: (a) PCR amplification of the desired plasmid DNA or specific mRNA, (b) nucleic acid hybridization, (c) presence or absence of "marker" gene functions, and (d) expression of inserted sequences. In the first approach, the nucleic acids can be amplified by PCR to provide for detection of the amplified product. In the second approach, the presence of a foreign gene inserted in an expression vector can be detected by nucleic acid hybridization using probes comprising sequences that are homologous to an inserted PTP gene. In the third approach, the recombinant vector/host system can be identified and selected based upon the presence or absence of certain "marker" gene functions (e.g., β-galactosidase activity, thymidine kinase activity, resistance to antibiotics, transformation phenotype, occlusion body formation in baculovirus, etc.) caused by the insertion of foreign genes in the vector. In another example, if the nucleic acid encoding a PTP is inserted within the marker gene sequence of the vector, recombinants containing the PTP insert can be identified by the absence of the marker gene function. In the fourth approach, recombinant expression vectors can be identified by assaying for the activity of the gene product expressed by the recombinant, provided that the expressed protein assumes a functionally active conformation. Such assays can be based, for example, on the physical or functional properties of the a PTP gene product in in vitro assay systems, e.g., tyrosine phosphorylation, or alternatively binding with antibody.

Once a particular recombinant DNA molecule is identified and isolated, several methods known in the art may be used to propagate it. Once a suitable host system and growth conditions are established, recombinant expression vectors can, be propagated and prepared in quantity. As previously explained, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

In addition, a host cell strain may be chosen which modulates the expression of the inserted sequences, or modifies and processes the gene product in the specific fashion desired. Different host cells have characteristic and specific mechanisms for the translational and post-translational processing and modification (e.g., glycosylation, cleavage [e.g., of signal sequence]) of proteins. Appropriate cell lines or host systems can be chosen to ensure the desired modification and processing of the foreign protein expressed. For example, expression in a bacterial system can be used to produce an nonglycosylated core protein product. However, the transmembrane PTP protein expressed in bacteria may not be properly folded. Expression in yeast can produce a glycosylated product. Expression in eukaryotic cells can increase the likelihood of "native" glycosylation and folding of a heterologous protein. Furthermore, different vector/host expression systems may affect processing reactions, such as proteolytic cleavages, to a different extent.

Vectors are introduced into the desired host cells by methods known in the art, e.g., transfection, electroporation, microinjection, transduction, cell fusion, DEAE dextran, calcium phosphate precipitation, lipofection (lysosome fusion), use of a gene gun, or a DNA vector transporter (see, e.g., Wu et al., 1992, J. Biol. Chem. 267:963–967; Wu and Wu, 1988, J. Biol. Chem. 263:14621–14624; Hartmut et al., Canadian Patent Application No. 2,012,311, filed Mar. 15, 1990).

As noted above, the PTP of the invention can be expressed as an integral membrane protein, e.g., in its native conformation, or as a fragment. PTP fragments include, but are not limited to, the extracellular domain, the intracellular domain, or a combination thereof. A PTP fragment may include the membrane binding domain, and may thus be a membrane-binding fragment.

Recombinant PTP protein expressed as an integral membrane protein can be isolated and purified by standard methods. Generally, the integral membrane protein can be obtained by lysing the membrane with detergents, such as but not limited to, sodium dodecyl sulfate (SDS), Triton X-100, nonidet P-40 (NP-40), digoxin, sodium deoxycholate, and the like, including mixtures thereof. Solubilization can be enhanced by sonication of the suspension. Soluble forms of the protein can be obtained by collecting culture fluid, or solubilizing inclusion bodies, e.g., by treatment with detergent, and if desired sonication or other mechanical processes, as described above. The solubilized or soluble protein can be isolated using various techniques, such as polyacrylamide gel electrophoresis (PAGE), including chromatography (e.g., ion exchange, affinity, immunoaffinity, and sizing column chromatography), centrifugation, differential solubility, immunoprecipitation, or by any other standard technique for the purification of proteins.

In a specific embodiment, infra, the entire intracellular domain of ChPTPλ was ligated to the expression vector pKKUC12, which includes an inducible bacterial promoter. The recombinant expression vector, pkPTPλ, was transformed in E. coli DHB4 and expression induced by addition of IPTG. Bacterial extracts were prepared and assayed for tyrosine phosphatase activity, as described infra.

In another specific embodiment, a nucleic acid encoding a portion of the carboxyl-half of ChPTPλ was subcloned in the bacterial expression vector pET-3b as a fusion protein. The fusion protein expressed after transfection of E. coli was used to immunize rabbits and prepare antisera reactive with full length ChPTPλ.

In yet another specific embodiment, a PTPλ, or fragment, derivative, or analog thereof, can be expressed as a GST-fusion protein in a bacterial expression system.

Preferably, a fragment of PTPλ is expressed in such a system. A cDNA or gene fragment of PTPλ can be isolated, as described above, gel purified, blunt-ended with T4 DNA polymerase, and ligated with EcoRI-linearized, blunt ended pGEX-3X DNA (Smith and Johnson, 1988, Gene 67:31–40). The ligation mixture can then be transformed into E. coli and the clones obtained analyzed by restriction digestion and DNA sequencing. Products of resulting plasmids can be purified over glutathione-SEPHAROSE resin and eluted with free glutathione. The glutathione can be removed by passage through a PD10 desalting column.

In still another specific embodiment, Cos cells can be transiently transfected with plasmids containing PTPλ DNA, e.g., in the pBabePuro vector by the DEAE-dextran-Chloroquine method (Sabe et al., 1992, Proc. Natl. Acad. Sci. USA 89:2190–94). Transfected cells can be cultured for 60–72 hours to allow quantitative expression of the foreign PTPλ gene.

For expression in insect cell, the invention specifically provides for infection of Sf9 (Spodoptera frugiperda) cells at a multiplicity of infection of 10, with a recombinant baculovirus (Autographa californica), made by subcloning cDNA into the pAcYM1 vector (Matsuura et al., 1987, J. Gen. Virol. 68:1233–50). After 72 hours, cells can be lysed by Dounce homogenization in TNE buffer, and protein products purified by gel filtration, antibody affinity chromatography, or a combination of chromatography steps.

In another embodiment, the PTP of the invention is expressed in an indicator cell line, which is discussed in detail, infra. In this embodiment, isolation of the expressed protein is not desired, since the functional activity of the expressed protein in the indicator cell line is the property most of interest.

Identification and Characterization of PTP Polypeptides

Once a recombinant which expresses the PTP gene sequence is identified, the recombinant PTP product can be analyzed. This is achieved by assays based on the physical or functional properties of the product, including radioactive labelling of the product followed by analysis by gel electrophoresis, immunoassay, etc.

For example, the ability of the expressed protein, or a fragment comprising the intracytoplasmic domain thereof, to mediate hydrolysis of tyrosine phosphates can be determined. In one embodiment, proteins tyrosine kinase substrates, such as Raytide (Oncogene Science) or myelin basic protein (Sigma) can be phosphorylated on tyrosine and used as a substrate for phosphatase activity (see, e.g., Brown-Shimer et al., 1990, Proc. Natl. Acad. Sci. USA 87:5148–52). Alternatively, PTP assays can be performed in vitro, by measuring release of $^{32}$Pi (Brown-Shimer et al., supra).

In a specific embodiment, the PTP can be tested for the ability to dephosphorylate phospho-tyrosine 527 of the Src prototype of cytoplasmic tyrosine kinases. For example, any of the members of the Src family of tyrosine kinases, such as but not limited to, Src, Fyn, Lyn, Lck, and the like, can serve as substrates for dephosphorylation of phospho-tyrosine 527, which is located in the C-terminal end of these proteins.

In another preferred embodiment, the ability of a chimeric protein that comprises the PTP extracytoplasmic domain functionally associated with a protein tyrosine kinase domain to mediate tyrosine kinase activity can be determined.

The structure of PTP of the invention can be analyzed by various methods known in the art. Preferably, the structure of the various domains, particularly the PTP domain, is analyzed. Structural analysis can be performed by identifying sequence similarity with other known proteins. The degree of similarity (or homology) can provide a basis for predicting structure and function of PTP, or a domain thereof. In a specific embodiment, sequence comparisons can be performed with sequences found in GenBank, using, for example, the FASTA and FASTP programs (Pearson and Lipman, 1988, Proc. Natl. Acad. Sci. USA 85:2444–48).

The protein sequence can be further characterized by a hydrophilicity analysis (e.g., Hopp and Woods, 1981, Proc. Natl. Acad. Sci. U.S.A. 78:3824). A hydrophilicity profile can be used to identify the hydrophobic and hydrophilic regions of the PTPλ protein.

Secondary structural analysis (e.g., Chou and Fasman, 1974, Biochemistry 13:222) can also be done, to identify regions of PTPλ that assume specific secondary structures.

Manipulation, translation, and secondary structure prediction, as well as open reading frame prediction and plotting, can also be accomplished using computer software programs available in the art.

By providing an abundant source of recombinant PTP, the present invention enables quantitative structural determination of PTP, or domains thereof. In particular, enough material is provided for nuclear magnetic resonance (NMR), infrared (IR), Raman, and ultraviolet (UV), especially circular dichroism (CD), spectroscopic analysis. In particular NMR provides very powerful structural analysis of molecules in solution, which more closely approximates their native environment (Marion et al., 1983, Biochem. Biophys. Res. Comm. 113:967–974; Bar et al., 1985, J. Magn. Reson. 65:355–360; Kimura et al., 1980, Proc. Natl. Acad. Sci. U.S.A. 77:1681–1685). Other methods of structural analysis can also be employed. These include but are not limited to X-ray crystallography (Engstom, A., 1974, Biochem. Exp. Biol. 11:7–13).

More preferably, co-crystals of PTP and a PTP-specific ligand can be studied. Analysis of co-crystals provides detailed information about binding, which in turn allows for rational design of ligand agonists and antagonists. Computer modeling can also be used, especially in connection with NMR or X-ray methods (Fletterick, R. and Zoller, M. (eds.), 1986, Computer Graphics and Molecular Modeling, in *Current Communications in Molecular Biology*, Cold Spring Harbor Laboratory, Cold Spring Harbor, N.Y.).

In yet a further embodiment, a putative protein tyrosine phosphatase of the invention can be tested to determine whether it cross-reacts with an antibody specific for ChPTPλ. For example, the putative PTP can be reacted with a rabbit polyclonal antibody, as described in the Example, infra, to determine whether it binds. Alternatively, a PTP can be used to generate antibodies, which can be tested for cross reactivity with ChPTPλ. The degree of cross reactivity provides information about structural homology or similarity of proteins.

Antibodies Reactive With PTP

According to the invention, recombinant PTP, and fragments or other derivatives or analogs thereof, or cells expressing the foregoing may be used as an immunogen to generate antibodies which recognize the PTP. Such antibodies include but are not limited to polyclonal, monoclonal, chimeric, single chain, Fab fragments, and an Fab expression library.

Various procedures known in the art may be used for the production of polyclonal antibodies to a recombinant PTP or derivative or analog thereof. For the production of antibody, various host animals can be immunized by injection with the recombinant PTP, or a derivative (e.g., fragment) thereof, including but not limited to rabbits, mice, rats, etc. In one embodiment, the recombinant PTP or fragment thereof can be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*.

For preparation of monoclonal antibodies directed toward an PTP or analog thereof, any technique which provides for the production of antibody molecules by continuous cell lines in culture may be used. These include but are not limited to the hybridoma technique originally developed by Kohler and Milstein (1975, Nature 256:495–497), as well as the trioma technique, the human B-cell hybridoma technique (Kozbor et al., 1983, Immunology Today 4:72), and the EBV-hybridoma technique to produce human monoclonal antibodies (Cole et al., 1985, in *Monoclonal Antibodies and Cancer Therapy*, Alan R. Liss, Inc., pp. 77–96). In an additional embodiment of the invention, monoclonal antibodies can be produced in germ-free animals utilizing recent technology (PCT/US90/02545). According to the invention, human antibodies may be used and can be obtained by using human hybridomas (Cote et al., 1983, Proc. Natl. Acad. Sci. U.S.A. 80:2026–2030) or by transforming human B cells with EBV virus in vitro (Cole et al., 1985, in *Monoclonal Antibodies and Cancer Therapy*, Alan R. Liss, pp. 77–96). In fact, according to the invention, techniques developed for the production of "chimeric antibodies" (Morrison et al., 1984, J. Bacteriol. 159–870; Neuberger et al., 1984, Nature 312:604–608; Takeda et al., 1985, Nature 314:452–454) by splicing the genes from a mouse antibody molecule specific for a PTPλ together with genes from a human antibody molecule of appropriate biological activity can be used; such antibodies are within the scope of this invention. Such human or humanized chimeric antibodies are preferred for use in therapy (described infra), since the human or humanized antibodies are much less likely than xenogenic antibodies to induce an immune response, in particular an allergic response, themselves. According to the invention, techniques described for the production of single chain antibodies (U.S. Pat. No. 4,946,778) can be adapted to produce PTP-specific single chain antibodies. An additional embodiment of the invention utilizes the techniques described for the construction of Fab expression libraries (Huse et al., 1989, Science 246:1275–1281) to allow rapid and easy identification of monoclonal Fab fragments with the desired specificity for a PTP, or its derivatives, or analogs.

Antibody fragments which contain the idiotype of the antibody molecule can be generated by known techniques. For example, such fragments include but are not limited to: the $F(ab')_2$ fragment which can be produced by pepsin digestion of the antibody molecule; the Fab' fragments which can be generated by reducing the disulfide bridges of the $F(ab')_2$ fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. For example, to select antibodies which recognize a specific epitope of an PTP, one may assay generated hybridomas for a product which binds to a PTP fragment containing such epitope. For selection of an antibody specific to an PTP from a particular species of animal, one can select on the basis of positive binding with PTP expressed by or isolated from cells of that species of animal.

The foregoing antibodies can be used in methods known in the art relating to the localization and activity of PTP, e.g., for Western blotting, imaging PTP, measuring levels thereof in appropriate physiological samples, etc.

In a specific embodiment, antibodies that agonize or antagonize the activity of PTP can be generated. Such antibodies can be tested using the assays described infra for identifying ligands.

Ligand Agonists and Antagonists of PTP

Identification and isolation of a gene encoding PTP of the invention provides for expression of the protein in quantities greater than can be isolated from natural sources, or in indicator cells that are specially engineered to indicate the activity of a protein expressed after transfection or transformation of the cells. According, the present invention contemplates identifying specific ligands of PTP using various screening assays known in the art.

Any screening technique known in the art can be used to screen for PTP agonists or antagonists. The present invention contemplates screens for small molecule ligands or ligand analogs and mimics, as well as screens for the native ligand that binds to and activates PTP of the invention in vivo.

Knowledge of the primary sequence of the protein, and the similarity of that sequence with proteins of known function, can provide an initial clue as the inhibitors or antagonists of the protein. Identification and screening of antagonists is further facilitated by determining structural features of the protein, e.g., using X-ray crystallography, neutron diffraction, nuclear magnetic resonance spectrometry, and other techniques for structure determination. These techniques provide for the rational design or identification of inhibitors and antagonists.

Another approach uses recombinant bacteriophage to produce large libraries.

Using the "phage method" (Scott and Smith, 1990, Science 249:386–390; Cwirla, et al., 1990, Proc. Natl. Acad. Sci., 87:6378–6382; Devlin et al., 1990, Science, 249:404–406), very large libraries can be constructed ($10^6$–$10^8$ chemical entities). A second approach uses primarily chemical methods, of which the Geysen method (Geysen et al., 1986, Molecular Immunology 23:709–715; Geysen et al. 1987, J. Immunologic Method 102:259–274) and the recent method of Fodor et al. (1991, Science 251, 767–773) are examples. Furka et al. (1988, 14th International Congress of Biochemistry, Volume 5, Abstract FR:013; Furka, 1991, Int. J. Peptide Protein Res. 37:487–493), Houghton (U.S. Pat. No. 4,631,211, issued December 1986) and Rutter et al. (U.S. Pat. No. 5,010,175, issued Apr. 23, 1991) describe methods to produce a mixture of peptides.

In another aspect, synthetic libraries (Needels et al., 1993, "Generation and screening of an oligonucleotide encoded synthetic peptide library," Proc. Natl. Acad. Sci. USA 90:10700–4; Lam et al., International Patent Publication No. WO 92/00252, each of which is incorporated herein by reference in its entirety), and the like can be used to screen for PTP ligands according to the present invention.

Alternatively, assays for binding of soluble ligand to cells that express recombinant forms of the PTP extracellular domain can be performed. The soluble ligands can be provided in cellular extracts or conditioned media (see Pele et al., 1992, Cell 69:205–216).

The screening can be performed with recombinant cells that express the PTP, or alternatively, using purified protein, e.g., produced recombinantly, as described above. For example, the ability of labeled, soluble or solubilized PTP that includes the extracellular (ligand-binding) portion of the molecule, to bind ligand can be used to screen libraries, as described in the foregoing references.

In a preferred embodiment, a chimeric construct consisting of the extracellular domain of PTP, with the intracellular domain of a tyrosine kinase, such as cEyk or EGFR is expressed in a transformed or transfected cell line. Detection of kinase activity is generally easier than detection of phosphatase activity, and it is likely that binding of ligand to the receptor domain of PTP will activate kinase activity of the intracellular domain. Such a cell line can serve as an indicator cell line, e.g., if activation of the kinase activity of the chimeric construct by binding of ligand to the PTP extracellular domain induces some observable phenotypic change.

Genetic approaches to identification of ligands are also possible. These approaches are particularly facilitated by use of a chimeric construct consisting of a PTP extracellular domain and a tyrosine kinase intracellular domain.

One such approach is particularly effective if the ligand is a membrane bound ligand. In this embodiment, mammalian cells that overexpress PTP-tyrosine kinase chimeric molecules may be transfected with an expression cDNA library, e.g., a splenic cDNA library. By creation of a transforming autocrine loop, cells that received cDNA of a PTP ligand can be isolated as transformed foci, as used for isolation of KGF receptor (Miki et al., 1991, Science 251:72–75). Such clones may be identified by higher levels of phosphotyrosine due to activation of the PTP-tyrosine kinase chimera. in a second embodiment, cDNA expression libraries may be screened by binding with the extracellular domain of PTP. The cDNA can be transfected into E. Coli, and pools of about 10,000 independent clones can be separated and grown in agar plates. Plasmids obtained form the pool can be transfected in mammalian expression cells, such as Cos cells, and these cells can be tested for binding to the PTP extracellular domain. This method, similar to the method used to isolate the TGFβ type II receptor (Lin et al., 1992, Cell 68:775–785), allows the ligand protein to be processed (e.g., glycosylated) in Cos cells, so that the ligand will be more likely to have its native structure.

In a third embodiment, a recently developed two-hybrid system, which utilizes the reconstitution of GAL4 (a transcriptional activator from yeast) function (Files and Song, 1989, Nature 340:245–246; Chien et al., 1991, Proc. Natl. Acad. Sci. USA 88:9578–82; yang et al., 1992, Science 257:680–682), may effectively allow isolation of genes involved in protein interactions.

Once a native ligand is isolated, it can be analyzed, as described herein with respect to PTP itself, for its structural and physiological characteristics.

Diagnostic and Therapeutic Methods

Protein phosphorylation is one means by which cells control activation, proliferation, and differentiation. Therefore, the level of expression of PTP of the invention, and the ability to modulate activity of PTP of the invention, can be very important for the diagnosis and treatment of diseases of disorders, particularly cellular transformations that lead to cancer, and to immune system function.

Thus, the nucleic acid probes (enzyme or radio-labeled nucleotides) or antibodies of the invention can be used to detect expression, and measure the level of expression, of a PTP of the invention in selected tissues. For example, the presence or absence of expression of PTP in cancer cells obtained in a tissue biopsy can be important in evaluating whether the normal cellular control machinery are operating. Similarly, the presence or absence, and level of expression, of PITP of the invention in immune cells can provide information about the level of immune activation and regulation.

In another aspect of the invention, antisense oligonucleotides capable of hybridizing to PTPλ mRNA can be used to inhibit expression of PTPλ in a cell, and thus modulate phosphatase activity in a cell. Inhibition of PTPλ activity can be useful, e.g., to modulate the activity of immune cells. For example, during a pathological inflammatory response or an autoimmune disease, it may be desirable to modulate immune cell activity by inhibiting activation of immune cells.

In another embodiment, a soluble form of the extracytoplasmic domain of PTPλ can be used therapeutically, the antagonize cellular PTPλ by binding with ligand. This embodiment of the invention can be used to modulate immune cell activity, as described above, e.g., in an autoimmune disease or during inflammation. Accordingly, the invention provides for administration of a therapeutically effective amount of a soluble PTPX extracellular domain, and for a pharmaceutical composition comprising a soluble PTPX extracellular domain and a pharmaceutically acceptable carrier.

In a further embodiment, ligand agonists or antagonists can be used to modulate cellular activity by increasing or decreasing the activity of the PTP of the invention in cells.

In one embodiment, a ligand agonist of PTP can be used alone, or as an adjunct, in the treatment of cancer, when oncogenesis is the result of uncontrolled protein phosphorylation, such as mediated by Src and similar oncogenic tyrosine kinases. Activation of PTP activity in such cells can result in more normal regulation of protein phosphorylation, thus inhibiting oncogenesis. In particular, dephosphorylation of phospho-tyrosine 527 of an oncogenic tyrosine kinase may reduce the kinase activity of the kinase, thus limiting otherwise uncontrolled cellular activation.

In another embodiment, a PTP ligand antagonist can be used to inhibit the tyrosine phosphatase activity. This may be beneficial to modulate, and preferably enhance, an immune response, by allowing greater protein phosphorylation to occur. Modulation of immune response can be important in individuals who are immunocompromised, such as those suffering from AIDS, chronic viral infections, radiation therapy or exposure, old age, and other immunosuppressive conditions.

The present invention may be better understood by reference to the following non-limiting example, which is provided by way of exemplification.

EXAMPLE

The present Example discloses the first chicken transmembrane PTP, ChPTPλ, isolated from a brain cDNA library and preB cells. ChPTPλ has transcripts about 5.6 kb, and is abundant in spleen, intestine and in fibroblasts transformed by oncogenic ras or erbA/B. It has five alternative splicing products varying near their N-terminus, and the largest one contains 1237 amino acids. The extracellular domain of ChPTPλ has several features including a Ser/Thr/Pro-rich region, one fibronectin type III domain, and spectrin-like repeats. This represents the first case in which spectrin-like repeats were found in a non-cytoplasmic domain of a protein.

Antibodies to ChPTPλ recognized several protein species whose $M_r$ range from 170 to 210 kDa. ChPTPλ exhibited phosphotyrosine-specific phosphatase activity. Since human CD45 also has similar features in the extracellular domain, and since the two PTPs share 70% similarity in the intracellular domains, ChPTPλ and CD45 appear to belong to the same gene family. However, it is equally evident that ChPTPλ is most likely not the chicken homolog of human CD45.

Materials and Methods cDNA Cloning and Sequencing. A cDNA probe encoding the intracellular domain of human CD45 (20), was used to screen a λgt10 cDNA libraries derived from 11-day-old chicken embryonic brain at low stringency conditions (30% formamide/5×SSC/20 mM Tris-HCI, pH 7.4/0.5% SDS/1 mM EDTA/0.2 mg per ml salmon sperm DNA/$10^6$ cpm per ml $^{32}$P-labeled cDNA at 37° C.). Phage DNA containing the positive signals was prepared, and cDNA inserts were subcloned into pBluescript SK(-) (Stratagene). To complete the 5'-end sequence, the 5' rapid amplification of cDNA ends (5'RACE) and sequential polymerase chain reaction (PCR) were employed on template poly(A)⁺RNA isolated from a chicken preB cell line DT40, following the manufacturer's manual (GIBCO/BRL). Briefly, the first strand cDNA was reverse transcribed in vitro and then tailed with poly-dC. PCR was followed, using poly-dG and ChPTPλ-specific primers [5'-CCTCTGATTCTCACCACTGTT-3' (λP1)(SEQ ID NO:33) and 5'-TGTATATCTTCTGCACCAA-3' (λP2)(SEQ ID NO:34), FIG. 1A]. The N-terminal sequence was also examined by PCR of the first-strand cDNA from DT40 cells, using either primers λpn (5'-CCATGTTTTTGTGCCTTAA-3'; SEQ ID NO:35) and λp2 or λpn and λp3 (5'-CGTGATGACTGGTGTGGT-3'; SEQ ID NO:36), then visualizing the PCR fragments in 2% agarose gel (FIG. 1C). Positions of all primers are indicated in FIG. 1A and underlined in FIG. 2A–2C. PCR products were subcloned to the vector pCR1000 (Invitrogen). All cDNA clones were sequenced on both strands, using the Sequenase system (United States Biochemical Co.) (21, 22). The search of sequence homology was done through the FASTA and FASTP programs in GenBank (23). The GenBank accession number of ChPTPλ is L13285.

Antibody (A299) preparation-A 1.6 kb cDNA fragment encoding 478 amino acids (residue 738 to 1216) in the carboxyl-half of ChPTPλ was excised with BamHI/EcoRI and subcloned into the expression vector pET-3b (24). The recombinant was transformed into E. coli BL21(DE)pLysS and the fusion protein was induced by 0.4 mM isopropyl β-D-thiogalactopyranoside (IPTG). Bacteria were lysed by sonication in RIPA (1 % Triton X-100/1% sodium deoxycholate/0.1% SDS/20 mM Tris-HCl, pH 7.4/150 mM NaCl/5 mM EDTA) and centrifuged at 10,000×g for 10 min at 4° C. The fusion protein in the pellet was separated by gel electrophoresis and prepared for immunization of rabbits (25). The antisera were purified by immunoglobulin selection (25), dialyzed in phosphate-buffered saline (PBS), and concentrated by Centriprep (Amicon).

Cells, Immunoblotting and Immunoprecipitation. Chicken embryo fibroblasts (CEF) were cultured and infected with viruses using the method of DEAE-dextran as previously described (26). DT40 cells were cultured in RPMI Medium 1640 (GIBCO) containing 10% fetal calf serum and 1% chicken serum (27). Other chicken hematopoietic cell lines were cultured in F-10 medium supplemented with 8% calf serum and 2% chicken serum (28–32). Chicken osteoclasts and bone marrow cells were prepared as described (33).

For immunoblot (Western) analysis, cells were lysed in 1% SDS containing protease inhibitor mix (1 mM phenylmethylsulfonyl fluoride/2 μg aprotinin per ml/1 μg pepstatin per ml) (Boehringer). After clarification by centrifugation, 50 μg protein of each sample was subjected to a 7.5% SDS-polyacrylamide gel electrophoresis (SDS-PAGE) (34). Proteins were transferred to nitrocellulose filters, and filters were incubated with A299 (1 μg/ml immunoglobulin) then labeled by ¹²⁵I-labeled protein A (25). For immunoprecipitation, cells were solubilized in 1% NP-40/PBS/protease inhibitor mix, then ChPTPλ was immunoprecipitated with pA299 (25).

Bacterial Expression of ChPTPλ. A 2 kb-cDNA fragment encoding the entire intracellular domain of ChPTPλ was excised by HindIII and EcoRI (starting from leucine 520, FIG. 2A–2C) and ligated to the expression vector pKKUC12. The recombinant, pkPTPλ, was transformed into E.coli DHB4 that lacks alkaline phosphatase (35). After induction by 0.4 mM IPTG for 2 h, bacterial extracts were prepared (5) and 5 μl samples were used for PTP assays. The extract of DHB4 containing the vector only was used as a negative control.

PTP Assay. Raytide (Oncogene Science) and bovine brain myelin basic protein (Sigma) (20 μg each) were phosphorylated on tyrosines by v-Src (34 pg), purified from a baculovirus expression system (35a), in 50 μl containing 20 mM Tris-HCl, pH 7.2/5 mM MnCl₂/50 μCi [γ-³²P]ATP at 30° C. for 3 h. Casein and histone 2B (Sigma) were phosphorylated on serines and threonines by the catalytic subunit of calf heart cAMP-dependent protein kinase (1 U, Sigma) in 50 μl including 25 mM Hepes, pH 7.4/10 mM MgCl₂/10 mM DTT/50 μCi [γ-³²P]ATP. All reactions were terminated by TCA-precipitation and resuspended in Tris-HCl (pH 8.0) as previously described (5).

For in vitro PTP assay, the immunoprecipitate was washed three times with lysis buffer and once with PBS, then resuspended in 30 μl of PTP buffer (50 mM Hepes, pH 7.5/5 mM EDTA/10 mM DTT/2–5×10⁴ cpm ³²P-labeled substrate). When bacterial extract was used, assay was done in 50 μl of PTP buffer. After incubating at 30° C. for 30 min, the reactions were stopped, and the released ³²Pi was measured as previously described (5).

Northern Blot Analysis. Total RNA was isolated from chicken tissues and cells by the acid guanidinium thiocyanate-chloroform extraction method (36), and Poly (A)⁺RNA was selected by poly-dT chromatograph (37). 10 μg poly(A)⁺RNA was separated on a 1% formaldehyde-denaturing agarose gel and transferred to Zetabind nylon membrane (AMF Cuno). The membrane was prehybridized and hybridized under high stringency conditions [50% formamide/5×SSC/1×Denhardt's/20 mM NaPO₄, pH 6.7/100 μg per ml SS DNA/10% Dextran sulfate/5–10×10⁵ cpm per ml ³²P-labeled cDNA fragment 6a (FIG. 1A) at 42° C.]. The membrane was washed finally in 0.1×SSC/0.1% SDS at 65° C. for 30 min. 18S rRNA was probed as a loading control.

Results

Isolation of chicken PTPλ cDNA clones. Using a cDNA fragment encoding the PTP domain of human CD45 as a probe, we screened 6×10⁵ λgt10 phage plaques of a chicken embryonic brain cDNA library. Of 27 positive clones, four were duplicates encoding partial ChPTPλ. The sequence strategy is outlined in FIG. 1A. The 5'-cDNA sequence encoding most of the extracellular domain was obtained by 5'RACE from mRNA of chicken preB DT40 cells (see Experimental Procedures). Near the 5'-end of ChPTPλ we found many clone variants that fell into five groups, denoted a, b, c, d and e (FIG. 1B). They differed in a region which could be dissected into four segments, denoted I, II, III and IV. Group a has all four segments; group b has segments II, III and IV; group c has segments I, II and IV; group d has segments II and IV; and group e has only segment II. All the missing segments in groups b-e resulted in in-frame continuation of amino acid sequences.

To confirm these findings, we performed PCR with primers franking this region. FIG. 1C shows multiple PCR products at the predicted lengths (lane b and c), except a fragment corresponding to 6C1 (FIG. 1A, or group 1 in FIG. 1B) that was predicted at 380 bp and 620 bp in lane b and c of FIG. 1C, respectively. This was probably due to the low abundance of this transcript, or due to the preferable usage of primers and nucleotides by smaller fragments in PCR reactions. FIG 1C also suggests relative abundance of ChPTPλ variants in DT40 cells: groups b and c were similarly abundant but more than groups d, e, and a. Sequences of PCR fragments were verified by direct sequencing and were consistent with cloning data described above. Therefore, we propose that these clone variants represent five ChPTPλ transcripts, resulting from alternative splicing of the same gene.

Figure 2A:
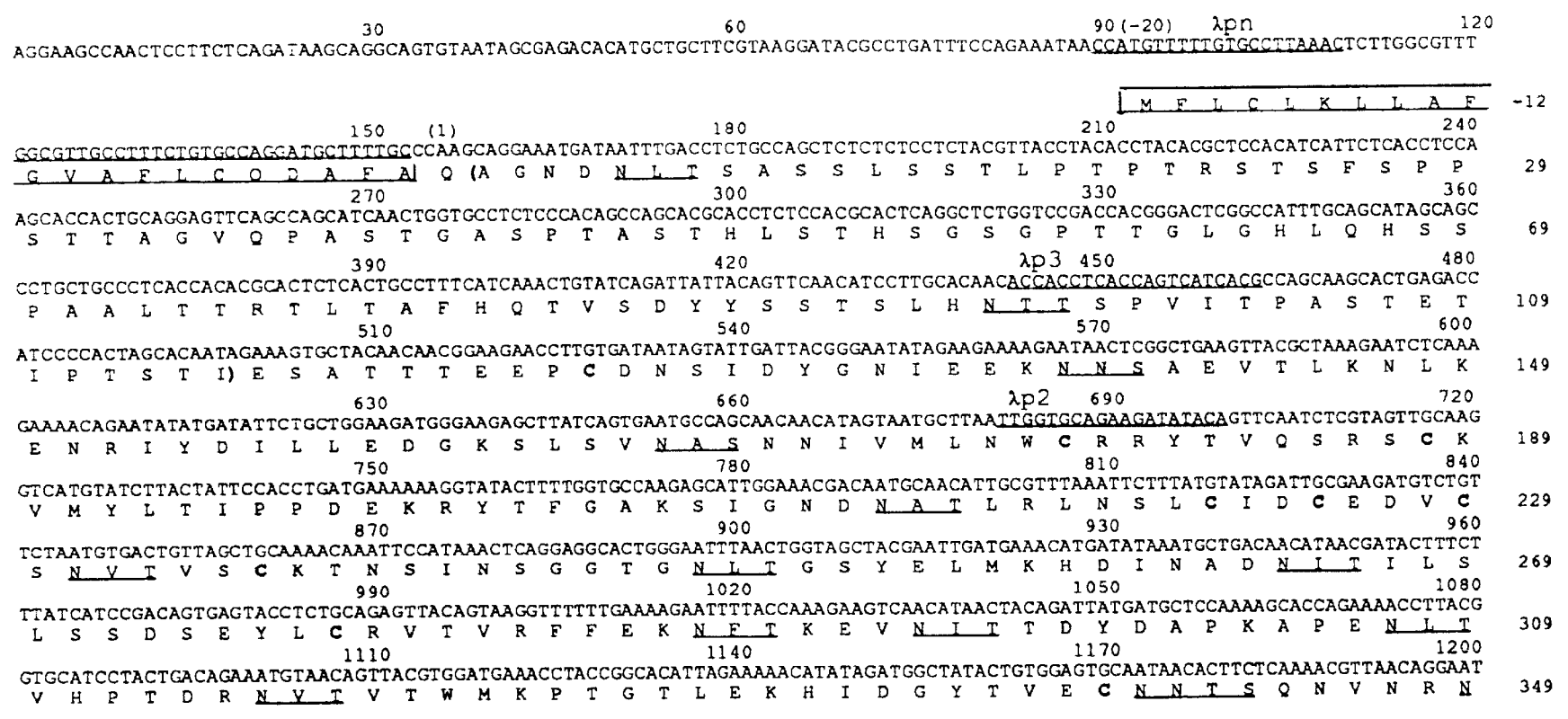
Figure 2B:
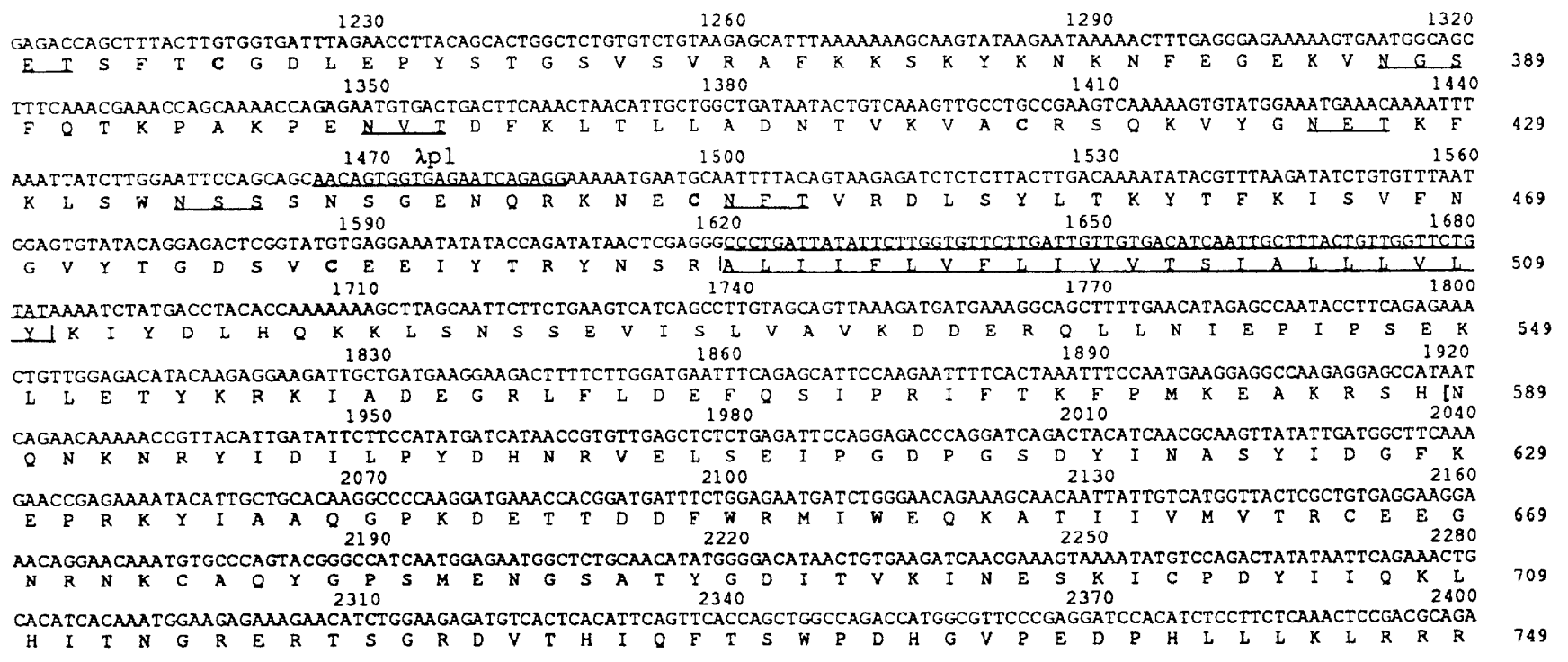

Structure of ChPTPλ. The largest ChPTPλ cDNA, clone a, encodes 1237 amino acids, containing a putative N-terminal signal peptide (21 residues) and one hydrophobic transmembrane span (22 residues) (FIG. 2A–2C). Based upon the features of signal peptides (38, 39), the N-terminus of the mature ChPTPλ most likely begins at glutamine at position 1. The ChPTPλ structure is shown schematically in FIG. 1B. Like most of the transmembrane PTPs, the intracellular domain of ChPTPλ possesses two tandem PTP domains. A homology search through GenBank showed that ChPTPλ has the highest similarity with human CD45, 70% in their intracellular domains. The extracellular domain of ChPTPλ did not align significantly with any known protein, except 20% with that of human CD45.

The extracellular domain of ChPTPλ presents the following features. Firstly, it is rich in sites potential for oligosaccharides. There are 20 asparagine residues in NXS/T motif that are signals for N-linked glycosylation (38). Within the beginning 135 amino acids of the mature protein, there are 52 serine/threonine and 12 proline residues-comprising 47.4% of the amino acids within this region. This Ser/Thr/Pro-rich region may embody many potential sites for O-linked glycosylation. It is also within this region that alternatively spliced segments I–IV locate and give rise to five ChPTPλ isoforms as mentioned above (FIG. 1B).

Figure 3:
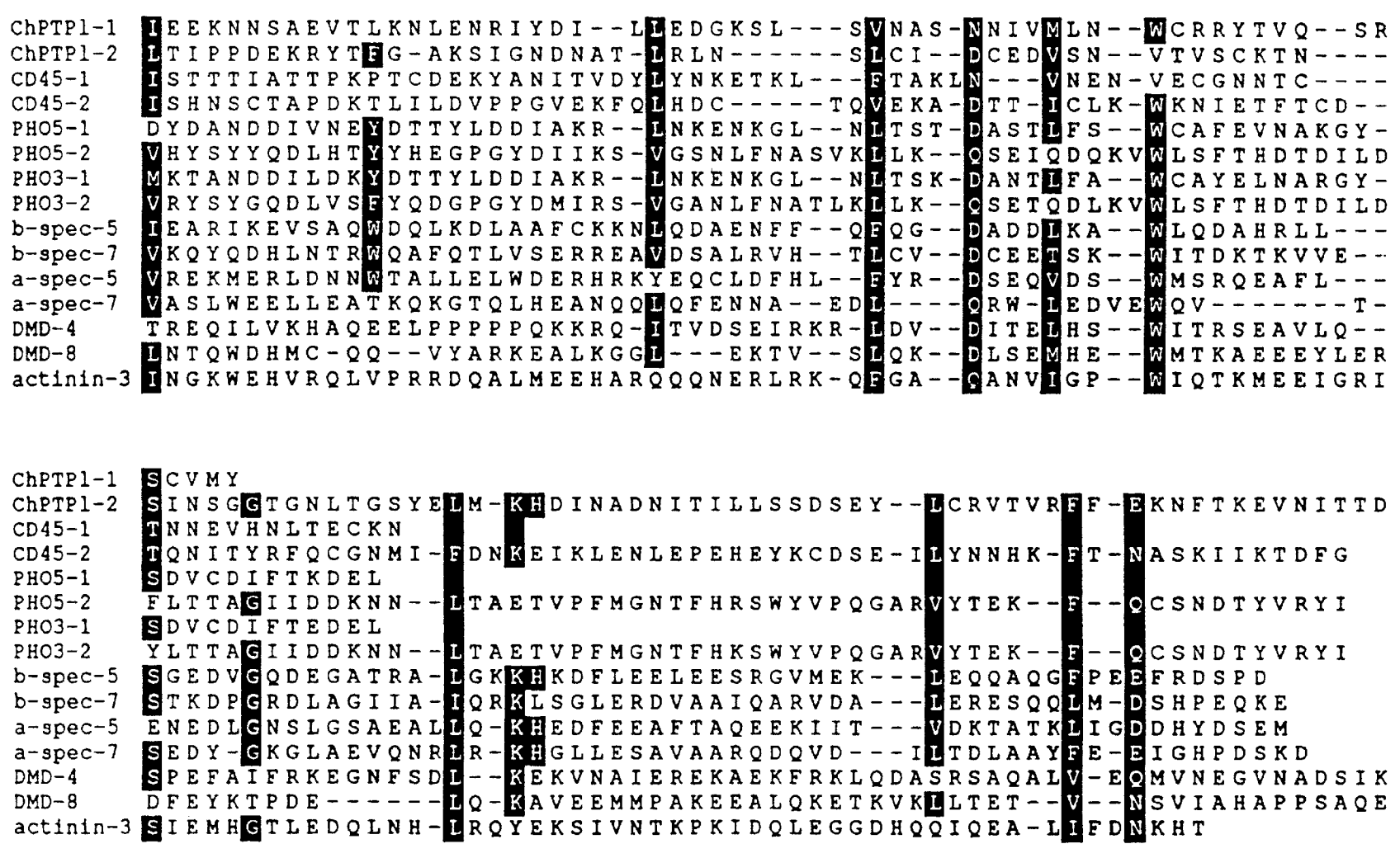

Following the Ser/Thr/Pro-rich region is a spectrin-like sequence containing 166 amino acids (residue 134 to 299). FIG. 3 shows the alignment of ChPTPλ with spectrin-like repeats of other known proteins including α-spectrin, β-spectrin, dystrophin, and α-actinin (40–43). This region of ChPTPλ is aligned as one and a half spectrin-like repeats. During homology search:, human CD45 and two yeast phosphatases, PHO5 and PHO3, were also found to contain spectrin-like repeats, which have never been reported.

Figure 4A:
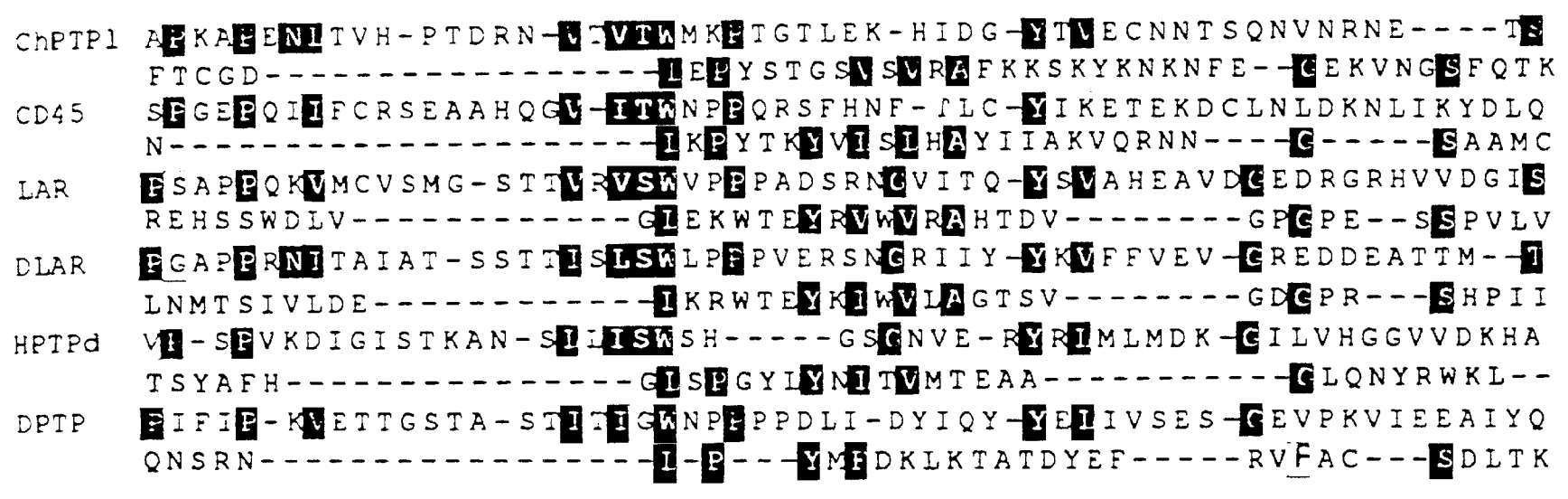

After the spectrin-like repeats, there is one fibronectin type-III (FN-III) domain composed of 93 amino acids (residue 302 to 393). FIG. 4A and 4B aligns ChPTPλ with FN-III domain-containing proteins including PTPs (also human CD45, 39), PTKs, cell adhesion molecules and fibronectin. Lastly, although the above-mentioned domains are not featured by cysteine residues, the extracellular portion of ChPTPλ has a relatively high content of cysteines, especially after the Ser/Thr/Pro-rich region (13/320) (FIG. 2A–2C).

Figure 6A:
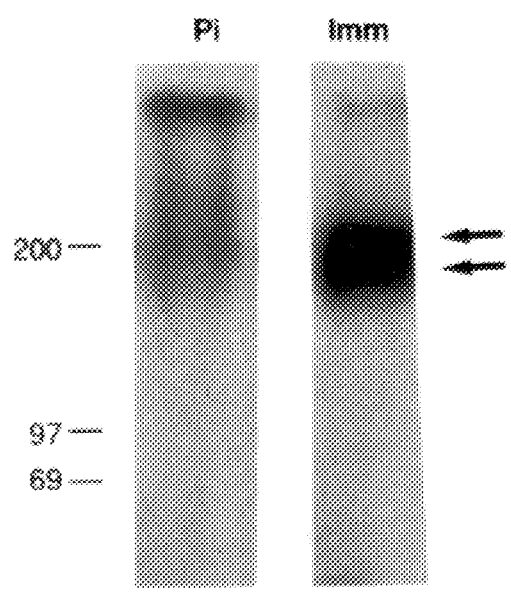
FIG. 6A–6C. Immune analyses of ChPTPλ. (A) Immunoblotting analysis of whole cell lysates of DT40. (B) Immunoprecipitation of [³H]leucine-labeled DT40 cell lysates. Pi, preimmune serum; Imm, antibody to ChPTPλ, A299. (C) Immunoblotting of other chicken cells with antibody A299. Lane A–F represent lysates of hematopoietic cell lines established by transformation with avian retroviruses. A, BM2C2 cell line, AMV transformed monoblasts; B, HD3 cell line, AEV transformed erythroblasts; C, HD11 cell lines, MC29 transformed macrophages; D, REV cell line, REV transformed T cells; E, RPL12 cell lines, RPL12 transformed B lymphoblasts; F, MSB-1 cell line, MDV transformed T lymphoblasts. Lane G, tertiary CEF; Lane H and I, enriched preparations of chicken osteoclasts and bone marrow cells, respectively.
Figure 6B:
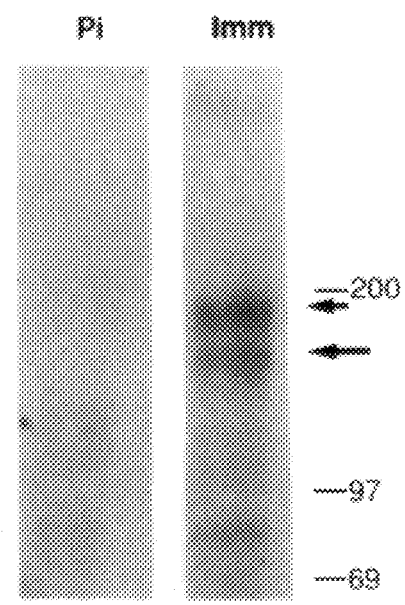

ChPTPλ expression. The tissue distribution of ChPTPλ was examined by Northern blot analysis of polyA+RNA prepared from adult chicken tissues. FIG. 5 shows that ChPTPλ has a broad mRNA band around 5.6 kb. It is abundant in spleen, intestine and preB DT40 cell, less in lung, low in brain (both cerebellum and telencephalon) and CEF, but absent in liver and muscle. ChPTPλ protein was studied by analyses with ChPTPλ-specific antibody, A299. Immunoblotting of DT40 cell lysates showed two major protein bands at M, 170 and 210 kDa (FIG. 6A). From DT40 cells metabolically labeled with [³H]leucine, A299 precipitated two proteins with similar M, (FIG. 6B). Since the predicted M, of ChPTPλ (group a) is about 140 kDa, both bands may represent the glycosylated forms of ChPTPλ.

Figure 6C:
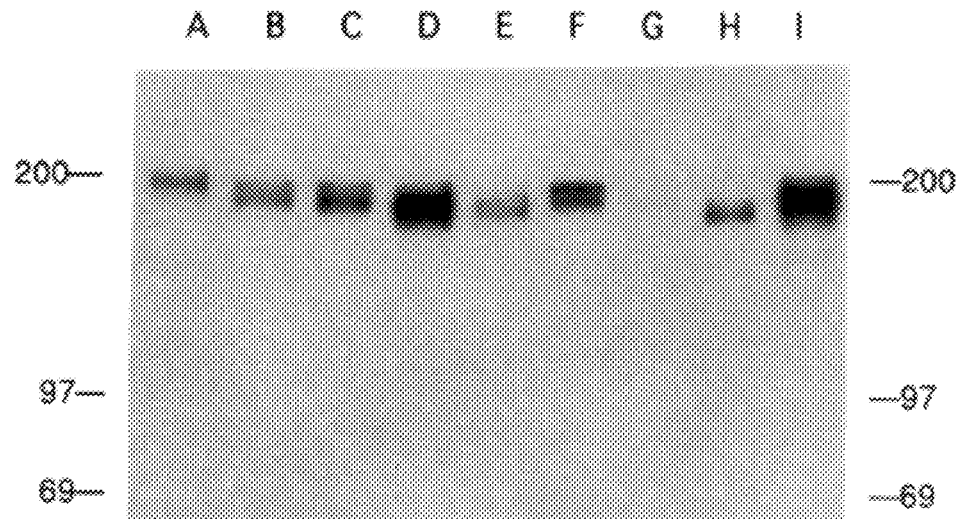

We also examined the ChPTPλ expression in other chicken cell lines. Antibody A299 identified multiple protein bands with M, from 170 to 210 kDa in CEF, erythroblasts, lymphocytes, lymphoblasts, macrophages, monoblasts, isolated osteoclasts and bone marrow cells (FIG. 6C). These cells expressed at least one protein band of different size. The multiple protein bands may reflect different isoforms and/or the high but variable carbohydrate content in the extracellular portion of ChPTPλ.

PTP activity of ChPTPλ. The enzymatic activity of ChPTPλ was measured after immunoprecipitation with A299 from DT40 cells. ChPTPλ hydrolyzed phosphotyrosines from Raytide and myelin basic protein (Table 1). Under the same condition, it did not hydrolyze phosphoserines/threonines from casein and histone 2B (data not shown). The PTP domain alone, pKPTPλ, also exhibited phosphotyrosine-specific activity when expressed in bacteria and assayed as bacterial extract (Table 1). Like most of PTPs, the reducing reagent (10 mM DTT) was required for ChPTPλ activity; while a chelator (EDTA or EGTA) was needed for ChPTPλ to reach a higher activity in vitro (Table 1). 1 mM orthovanadate, 0.1 mM molybdate, 1 mM iodoacetate and 10 mM zinc were potent inhibitors of ChPTPλ (>70%). Some ions, such as phosphate, $Mg^{2+}$ and $Mn^{2+}$, had less effect on ChPTPλ activity (<30%); others, such as $Na^+$ and $Ca^{2+}$, had no effect at all. Under the same assaying conditions, the activity of pKPTPλ was affected similarly by most ions, except that it was more sensitive to the inhibitors described above and that $Mn^{2+}$ showed some inhibitory influence (49%) (Table 1).

TABLE 1

Ion effects on the enzymatic activity of the full-length and truncated ChPTPλ

| IONS | ChPTPλ[a] (% activity) | pKPTPλ[a] (% activity) |
|---|---|---|
| 20 mM Hepes[b] | 0 | 0 |
| 1 mM DTT | 39 | ND[e] |
| 10 nM DTT | 65 | 80 |
| 5 nM EDTA[c] | 100 | 100 |
| 5 mM EGTA | 100 | 100 |
| 200 mM NaCl[d] | 100 | ND |
| 10 mM MgCl₂ | 80 | 80 |
| 10 mM MnCl₂ | 87 | 51 |
| 10 mM CaCl₂ | 100 | 90 |
| 10 mM NaPO₄ (pH 7.0) | 70 | 95 |
| 10 mM ZnCl₂ | 12 | 1 |
| 0.1 mM Na₃VO₄ | 78 | ND |
| 1 mM Na₃VO₄ | 4 | 2 |
| 0.1 mM Na₂MoO₄ | 24 | 11 |
| 1 mM Iodoacetate | 29 | ND |

[a]Immunoprecipitated ChPTPλ from DT40 ncells; pKPTPλ, truncated CHPTPλ containing the intracellular domain.
[b]Assays in the first three rows were based on buffer 20 mM Hepes (pH 7.4).
[c]Assays in the next two rows were based on buffer 20 mM Hepes (pH 7.4), 10 mM DTT.
[d]Assays in the next ten rows were based on buffer 20 mM Hepes (pH 7.4), 10 mM DTT, 5 mM EDTA.
[e]ND: not determined.

Figure 7:
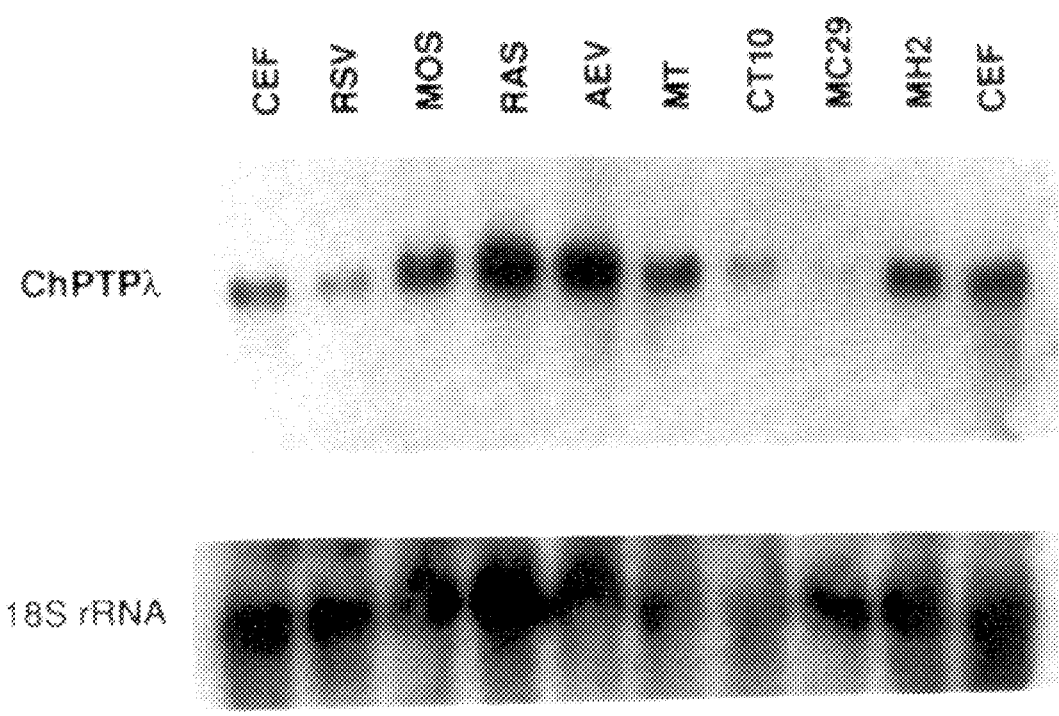
FIG. 7. Expression of ChPTPλ in transformed CEF. 10 μg of polyA⁺RNA was prepared from CEF infected by viruses bearing the following oncogenes: RSV-src, MOS-mos, RAS-ras, AEV-erbA/B, MT-SV40 middle T antigen, CT10-crk, MC29-myc, MH2-myc/mil. RNA was hybridized with ³²P-labeled fragment 6a (FIG. 1A). 18S rRNA was probed as a loading control (lower panel).

Expression of ChPTPλ in transformed CEF. Protein tyrosine phosphorylation is known to be an important step in oncogenesis of certain oncogenes, such as v-src and v-erbB (1, 50, 51). The role of PTPs in these processes is unknown. To evaluate ChPTPλ during tumorigenesis, the expression level of ChPTPλ was analyzed in CEF transformed by various oncogenes (FIG. 7). When CEF were transformed by oncogenic ras or erbA/B, ChPTPλ expression was elevated; when CEF were transformed by oncogenic src or myc, CLhPTPλ expression was decreased; when CEF were transformed by oncogenic mos, SV40 middle T antigen, crk or myc plus mil, ChPTPλ expression level was not affected significantly. These data suggest that ChPTPλ is regulated or functions differently during oncogenic processes controlled by different oncogenes.

Discussion

The present Example reports the first chicken PTP, ChPTPλ. Because it has many potential sites for O- and N-linked glycosylation and its apparent M, (170–210 kDa) is much larger than the predicted M, (14CI kDa), ChPTPλ is likely to be a transmembrane glycosylated cell surface protein. The intracellular domain of ChPTPλ shares 70% similarity with human CD45, 43% with HPTPα, 40% with HLAR, and 29% with HPTP1B. The extracellular portion of ChPTPλ consists of a Ser/Thr/Pro-rich region, one and a half spectrin-like repeats and one FN-III domain (FIG. 1B), making ChPTPλ unique and interesting among PTPs.

ChPTPλ is the first protein found to have spectrin-like repeats in the non-cytoplasmic compartment. Spectrin-like repeats were initially found in actin binding proteins, such as α- and β-spectrins, α-fodrin, α-actinin and dystrophin (40–43). The repeats consist of 106 to 120 amino acids per unit, with 4 to 17 units within each of these proteins. The function(s) of spectrin-like repeats are obscure, but they may serve as cables to connect functional domains at two ends (42). They may also bind to proteins directly, such as the repeat 15 of β-spectrin binding to ankyrin, which in turn links the β-spectrin to the membrane (43). ChPTPλ, however, contains only one-and-a-half spectrin-like repeats (FIG. 3). Although one of the two most conserved tryptophan residues is missing in ChPTPλ it is not clear what role this tryptophan residue plays in a spectrin-like repeat.

In addition to ChPTPλ, we found several other proteins containing spectrin-like repeats in the non-cytoplasmic compartments, including CD45, PHO3 and PHO5.

Interestingly, the four proteins share several properties. They are all phosphatases —ChPTPλ and CD45 (5) are PTPs; PHO5 and PHO3 are acid phosphatases from Saccharomyces cerevisiae (44). They all contain spectrin-like repeats in the non-cytoplasmic compartments—the two PTPs are transmembrane proteins with spectrin-like repeats in their extracellular portions; the two yeast phosphatases are secretory proteins in the periplasmic space. Their corresponding sequences are similar in length and all align as one and a half spectrin-like repeats (FIG. 3). Yeast acid phosphatases are known to scavenge phosphorus necessary for cell growth, and are associated with cell cycle regulation and bud emergence (45). Our findings suggest more general functions of spectrin-like repeats, which may play a role in interacting with phosphatase ligands or substrates.

The FN-III domain has been reported in the extracellular domains of several PTPs (4). These PTPs usually have at least two tandem repeats, and some appear in combination with Ig-like loops, characteristic of cell adhesion molecules such as N-CAM (4). Differing from other PTPs, ChPTPλ and CD45 have only one FN-III domain (FIG. 4A and 4B). The three-dimensional structure of a single FN-III domain (90–100 amino acids) of fibronectin is very similar to that of human growth hormone receptor (hGHR) (46). One hGH molecule can bind to a hGHR receptor dimer (47). By analogy, it is possible that FN-III domains from more than one PTP molecule may participate in ligand interaction.

ChPTPλ and CD45 have striking similarities. Both have multiple isoforms differing near their N-termini (39). ChPTPλ has at least five isoforms (FIG. 1) and CD45 has at least eight isoforms, resulting from alternative splicing of a single gene (39). Isoforms and glycosylation of CD45 appear on the cell surface in a cell type-specific manner. The extracellular portions of both PTPs contain a Ser/Thr/Pro-rich region, one and a half spectrin-like repeats and one FN-III homologous domain, and both have been detected in hematopoietic tissues and cells.

However, the overall sequence similarity between ChPTPλ and CD45 is only 20% in the extracellular domain and 70% in the intracellular domain. This is much less than other known chicken-human homologs such as N-CAM and epidermal growth factor receptor, where there are at least 75% in the extracellular domains and 90% in the intracellular domains (48, 49). CD45 is expressed exclusively in hematopoietic cells except erythrocyte lineages (39); whereas ChPTPλ transcript has also been detected at low levels in lung and brain (FIG. 5), and the ChPTPλ protein has been found in CEF and erythroblasts (FIG. 6C). Moreover, the up- and down-regulations of ChPTPλ expression by different oncogenes in fibroblasts (FIG. 7) have not been reported in the study of CD45. Although the possibility that ChPTPλ is the chicken homologue of CD45 cannot be excluded completely, we propose that ChPTPλ and CD45 belong to the same gene family.

The following references have been cited by number throughout the specification:

1. Bishop, J. M. (1991) *Cell* 64, 235–248.
2. Rosen, O. M. (1987) *Science* 237, 1452–1458.
3. Fischer, E. H., Charbonneau, H., and Tonks, N. K. (1991) *Science* 253, 401–406.
4. Charbonneau, H., and Tonks, N. K. (1992) *Ann. Rev. Cell Biol.* 8, 463–493.
5. Krueger, N. X., Streuli, M., and Saito, H. (1990) *EMBO J.* 9, 3241–3252.
6. Brown-Shimer, S., Johnson, K. A., Lawrence, J. B., Johnson, C., Bruskin, A., Green, N. R., and Hill, D. E. (1990) *Proc. Natl. Acad. Sci. USA* 87, 5148–5152.
7. Chernoff, J., Schievella, A. R., Jost, C. A., Erikson, R. L., and Neel, B. G. (1990) *Proc. Natl. Acad. Sci. USA* 87, 2735–2739.
8. Cool, D. E., Tonks, N. K., Charbonneau, H., Walsh, K. A., Fischer, E. H., and Krebs, E. G. (1989) *Proc. Natl. Acad. Sci. USA* 86, 5257–5261.
9. Mosinger, J., B., Tillmann, U., Westphal, H., and Tremblay, M. (1992) *Proc. Natl. Acad. Sci. USA* 89, 499–503.
10. Woodford-Thomas, T. A., Rhodes, J. D., and Dixon, J. E. (1992) *J. Cell Biol.* 117, 401–414.
11. Freeman, R. M., Plutzky, J., and Neel, B. G. (1992) *Proc. Natl. Acad. Sci. USA* 89, 11239–11243.
12. Gu, M., York, J. D., Warshawsky, I., and Majerus, P. W. (1991) *Proc. Natl. Acad. Sci. USA* 88, 5867–5871.
13. Plutzky, J., Neel, B. G., and Rosenberg, R. D. (1992) *Proc. Natl. Acad. Sci.* 89, 1123–1127.
14. Shen, S.-H., Bastien, L., Posner, B. I., and Chretien, P. (1991) *Nature* 352, 736–739.
15. Yi, T., Cleveland, J. L., and Ihle, J. N. (1992) *Mol. Cell. Biol.* 12, 836–846.
16. Yang, Q., and Tonks, N. K. (1991) *Proc. Natl. Acad. Sci. USA* 88, 5949–5953.
17. Krueger, N. X., and Saito, H. (1992) *Proc. Natl. Acad. Sci. USA* 89, 7417–7421.
18. Levy, J. B., Canoll, P. D., Silvennoinen, O., Barnea, B., Morse, B., Honegger, A. M., Huang, J. T., Cannizzaro, L. A., Park, S. H., Druck, T., Huebner, K., Sap, J., Ehrlich, M., Nusacchio, J. M., and Schlessinger, J. (1993) *J. Biol. Chem.* 268, 10573–10581.
19. Bradykalnay, S. M., J., F. A., and Tonks, N. K. (1993) *J. Cell Biol.* 122, 961–972.
20. Streuli, M., Krueger, N. X., Tsai, A. Y., and Saito, H. (1989) *Proc. Natl. Acad. Sci. USA* 86, 8698–8702.
21. Chen, E. Y., and Seeburg, P. H. (1985) *DNA* 4, 165–170.
22. Sanger, F., Nicklen, S., and Coulson, A. R. (1977) *Proc. Natl. Acad. Sci. USA* 74, 5463–5467.

23. Pearson, W. R. and Lipman, D. J. (1988) *Proc. Natl. Acad. Sci. USA* 85, 2444–2448.
24. Rosenberg, A. H., Lade, B. N., Chui, D., Lin, S.-W., Dunn, J. J., and Studier, F. W. (1987) *Gene* 56, 125–135.
25. Harlow, E., and Lane, D. (1988) in *Antibodies, A laboratory manual* Cold Spring Harbor Laboratory Press.
26. Hanafusa, H. (1969) Proc. Natl. Acad. Sci. USA 63, 318–325.
27. Baba, T. W., Giroir, B. P., and Humphries, E. H. (1985) *Virology* 144, 139–151.
28. Introna, M., Golay, J., Frampton, J., Nakano, T., Ness, S. A., and Graf, T. (1990) *Cell* 63, 1287–1297.
29. Komfeld, S., Deug, G., Doederlein, G., and Graf, T. (1983) *Exp. cell Res.* 143, 383–394.
30. Beug, H., Doederlein, G., Freudenstein, C., and Graf, T. (1982) *J. Cell. Physiol.* 1, 195–207.
31. Metz, T., and Graf, T. (1991) *Genes & Dev.* 5, 369–380.
32. Beug, H., Muller, H., Grieser, S., Doederlein, G., and Graf, T. (1981) *Viology* 115, 295–309.
33. Horne, W. C., Neff, L., Chatterjee, D., Lomri, L., Levy, J. B., and Baron, R. (1992) *J. Cell Biol.* 119, 1003–1013.
34. Laemmli, U. K. (1970) *Nature* 227, 680–685.
35. Boyd, D., Manoil, C., and Beckwith, J. (1987) *Proc. Natl. Acad. Sci. USA* 84, 8525–8529.
35a. Fukui, Y., Saltiel, A. R., and Hanafusa, H. (1991) *Oncogene* 6, 407–411.
36. Chomczynski, P., and Sacchi, N. (1987) *Anal. Biochem.* 162, 156–159.
37. Sambrook, J., Fritsch, E. F., and Maniatis, T. (1989) in *Molecular cloning, A laboratory Mannual.* Cold Spring Harbor Laboratory Press.
38. Darnell, J. E., Lodish, H., and Baltimore, D. (1986) in *Molecular Cell Biology*. Scientific American Books, Inc, New York.
39. Thomas, M. L. (1989) *Ann. Rev. Immunol.* 7, 336–369.
40. Baron, M. D., Davison, M. D., Jones, P., and Crichley, D. R. (1987) *J. Biol. Chem.* 262, 17623–17629.
41. Davison, M. D., and Critchley, D. R. (1988) *Cell* 52, 159–160.
42. Marchesi, V. T. (1985) *Ann. Rev. Cell. Biol.* 1, 531–561.
43. Winkelmann, J. C., Chang, J. G., Tse, W. T., and Scarpa, A. L. (1990) *J. Biol. Chem.* 266, 11827–11832.
44. Bajwa, W., Meyhack, B., Rudolph, H., Schweingruber, A. M., and Hinnen, A. (1984) *Nucleic Acid Res.* 12, 7721–7739.
45. Tait-Kamradt, A. G., Turner, K. J., Kramer, R. A., Elliott, Q. D., Bostian, S. J., Thill, G. P., Rogers, D. T., and Bostain, K. A. (1986) *Mol. Cell. Biol.* 6, 1855–1865.
46. Main, A. L., Harvey, T. S., Baron, M., Boyd, J., and Campbell, I. D. (1992) *Cell* 71, 671–678.
47. de Vos, A.M., Ultsch, M., and Kossiakoff, A. A. (1992) *Science* 255, 306–312.
48. Barthels, D., Santoni, M., Wille, W., Ruppert, C., Chaix, J., Hirsch, M., Fontecilla, J. C., and Goridis, C. (1987) *EMBO J.* 6, 907–914.
49. Lax, I., Johnson, A., Howk, R., Sap, J., Bellot, F., Winkler, M., Ullrich, A., Vennstrom, B., Schlessinger, J., and Givol, D. (1988) *Mol. Cell. Biol.* 8, 1970–1978.
50. Cooper, J. A. (1990) in *The Src-family of protein-tyrosine kinases*. CRC Press, Boca Raton, Fla.
51. Flickinger, T. W., Maihle, N. J., and Kung, H. J. (1992) *Mol. Cell. Biol.* 12, 883–893.

The present invention is not to be limited in scope by the specific embodiments described herein, since such embodiments are intended as but single illustrations of one aspect of the invention and any functionally equivalent embodiments are within the scope of this invention. Indeed, various modifications of the invention in addition to those shown and described herein will become apparent to those skilled in the art from the foregoing description and accompanying drawings. Such modifications are intended to fall within the scope of the appended claims.

It is also to be understood that all base pair sizes given for nucleotides are approximate and are used for the purpose of description.

Various references are cited herein, the disclosures of which are incorporated by reference herein in their entirety.

---

What is claimed is:

1. An isolated protein that has an amino acid sequence consisting of amino acid 1 to 1237 of SEQ ID NO:2, or an amino acid sequence that differs from amino acid 1 to 1237 of SEQ ID NO:2 by only having conservative substitutions.

2. An isolated protein that has an amino acid sequence consisting of amino acid 22 to 1237 of SEQ ID NO:2, or an amino acid sequence that differs from amino acid 22 to 1237 of SEQ ID NO:2 by only having conservative substitutions.

3. An isolated protein having the amino acid sequence consisting of amino acid 22 to 509 of SEQ ID NO:2, or an amino acid sequence that differs from amino acid 22 to 509 of SEQ ID NO:2 by only having conservative substitutions.

4. An isolated peptide having the amino acid sequence consisting of amino acid 510 to 531 of SEQ ID NO:2, or an amino acid sequence that differs from amino acid 510 to 531 of SEQ ID NO:2 by only having conservative substitutions.

5. An isolated protein comprising the amino acid sequence consisting of amino acid 532 to 1237 of SEQ ID NO:2, or an amino acid sequence that differs from amino acid 532 to 1237 of SEQ ID NO:2 by only having conservative substitutions.

* * * * *